(12) United States Patent
Taylor et al.

(10) Patent No.: US 8,088,572 B2
(45) Date of Patent: Jan. 3, 2012

(54) **POLYNUCLEOTIDES FOR THE DETECTION OF *ESCHERICHIA COLI* O157:H7 AND *ESCHERICHIA COLI* O157:NM VEROTOXIN PRODUCERS**

(75) Inventors: Gregory Taylor, Ste-Therese (CA); Yvan Cote, Mirabel (CA); Alexandre Hébert, Laval (CA)

(73) Assignee: AES Chemunex S.A., Combourg (FR)

( * ) Notice: Subject to any disclaimer, the term of this patent is extended or adjusted under 35 U.S.C. 154(b) by 701 days.

(21) Appl. No.: 11/597,163

(22) PCT Filed: May 20, 2005

(86) PCT No.: PCT/CA2005/000748
§ 371 (c)(1),
(2), (4) Date: Aug. 27, 2007

(87) PCT Pub. No.: WO2005/113773
PCT Pub. Date: Dec. 1, 2005

(65) Prior Publication Data
US 2009/0170076 A1 Jul. 2, 2009

Related U.S. Application Data

(60) Provisional application No. 60/573,723, filed on May 20, 2004.

(51) Int. Cl.
*C12Q 1/68* (2006.01)
*C12P 19/34* (2006.01)
*C07H 21/02* (2006.01)
*C07H 21/04* (2006.01)

(52) U.S. Cl. ......... 435/6; 435/91.1; 435/91.2; 536/23.1; 536/24.3; 536/24.33

(58) Field of Classification Search .................. None
See application file for complete search history.

(56) References Cited

U.S. PATENT DOCUMENTS

| | | | |
|---|---|---|---|
| 5,474,796 A | 12/1995 | Brennan | |
| 5,580,703 A | 12/1996 | Kotin et al. | |
| 5,654,417 A | 8/1997 | Tarr et al. | |
| 5,691,146 A | 11/1997 | Mayrand | |
| 5,693,469 A | 12/1997 | Hogan | |
| 5,738,995 A | 4/1998 | Wu et al. | |
| 5,747,257 A | 5/1998 | Jensen | |
| 5,756,293 A | 5/1998 | Hall et al. | |
| 5,792,833 A | 8/1998 | Androphy et al. | |
| 5,855,885 A | 1/1999 | Smith et al. | |
| 5,876,930 A | 3/1999 | Livak et al. | |
| 5,925,517 A * | 7/1999 | Tyagi et al. ......... | 435/6 |
| 6,103,476 A | 8/2000 | Tyagi et al. | |
| 6,150,097 A | 11/2000 | Tyagi et al. | |
| 6,268,143 B1 | 7/2001 | Oberst | |
| 6,291,168 B1 | 9/2001 | Musso | |
| 6,365,723 B1 | 4/2002 | Blattner et al. | |
| 6,551,776 B1 | 4/2003 | Grimont et al. | |
| 6,610,836 B1 * | 8/2003 | Breton et al. ......... | 536/23.1 |
| 6,664,080 B1 | 12/2003 | Pfeffer | |

| | | |
|---|---|---|
| 2002/0150902 A1 | 10/2002 | Tarr |

FOREIGN PATENT DOCUMENTS

| | | | |
|---|---|---|---|
| EP | 0 587 279 | * | 3/1994 |
| WO | WO-89/06279 | * | 7/1989 |
| WO | WO-94/10325 | * | 5/1994 |
| WO | WO-94/28017 | * | 5/1994 |
| WO | WO 00/34484 | | 6/2000 |
| WO | WO 00/77247 A1 | | 12/2000 |
| WO | WO 03/000935 A1 | | 1/2003 |
| WO | WO-03/062464 | * | 7/2003 |
| WO | WO 2004048511 A2 | * | 6/2004 |
| WO | WO-2005/087930 | * | 9/2005 |

OTHER PUBLICATIONS

Buck et al., "Design Strategies and Performance of Custom DNA Sequencing Primers," BioTechniques, Sep. 1999, vol. 27, pp. 528-536.*
Perna, Nicole T., et al.; Genome sequence of enterohaemorrhagic *Escherichia coli* O157 :H7; Nature, vol. 409, Jan. 25, 2001, pp. 529-533 and Errata, Nature, vol. 10, Mar. 8, 2001, p. 240; ©2001 Macmillan Magazines Ltd.
Tarr, Phillip I., et al.; Acquisition of the rfb-gnd Cluster in Evolution of *Escherichia coli* O55 and O157; Journal of Bacteriology, Nov. 2001, p. 6183-6191, © 2000 American Society for Microbiology.
Shimizu, Takeshi, et al.; Analysis of the genes responsible for the O-antigen synthesis in enterohaemorrhagic *Escherichia coli* O157; Microbial Pathogenesis 1999; 26:235-247, Article No. mpat.1998.0253; © 1999 Academic Press.
International Search Report (PCT/CA2005/000748); Date of Mailing: Sep. 23, 2005; 2 pages.
Alignment for Accession No. AAQ65501 (WO 94/10325); 1994.*
Barcak et al., 'Comparative Nucleotide Sequence Analysis of Growth-Rate-Regulated gnd Alleles from Natural Isolates of *Escherichia coli* and from *Salmonella typhimurium* LT-2' Journal of Bacteriology 170(1) : 372-379, 1988.*
Basta et al., 'Sensitive Receptor-Specified Enzyme-Linked Immunosorbent Assay for *Escherichia coli* Verocytotoxin' Journal of Clinical Microbiology 27(7) : 1617-1622, 1989.*
Bastin, D. A., et al. (1995) Sequence and analysis of the O antigen gene (rfb) cluster of *Escherichia coli* O111. Gene 164 :17-23.*
Bennett et al., 'Evaluation of methods for the isolation and detection of *Escherichia coli* O157 in minced beef' Letters in Applied Microbiology 20 : 375-379, 1995.*
Bennett et al., 'The isolation and detection of *Escherichia coli* O157 by use of immunomagnetic separation and immunoassay procedures' Letters in Applied Microbiology 22 : 237-243, 1996.*
Bielaszewska et al., 'Isolation and Characterization of Sorbitol-Fermenting Shiga Toxin (Verocytotoxin)-Producing *Escherichia coli* O157 :H-Strains in the Czech Republic' Journal of Clinical Microbiology 36(7) : 2135-2137, 1998.*

(Continued)

*Primary Examiner* — Young J Kim
(74) *Attorney, Agent, or Firm* — Foley & Lardner LLP; Michel Morency

(57) ABSTRACT

Polynucleotide primers and probes for the specific detection of *E. coli* O157:H7 and/or *E. coli* O157:NM which produces verotoxin in samples are provided. The primers and probes can be used in real time diagnostic assays for rapid detection of *E. coli* O157:H7 and/or *E. coli* O157:NM which produces verotoxin. The primers and probes can be used in real-time diagnostic assays for rapid detection of *E. coli* O157:H7 and/or *E. coli* O157:NM which produces verotoxin in a variety of situations and are capable of distinguishing *E. coli* O157:H7 and/or *E. coli* O157:NM which produces verotoxin from other *E. coli* strains. Kits comprising the primers and probes are also provided.

47 Claims, 13 Drawing Sheets

OTHER PUBLICATIONS

Bilge, S.S., et al. (1996) Role of the *Escherichia coli* O157 :H7 O side chain in adherence and analysis of an rfb locus. Infect. Immun. 64:4795-4801.

Bisercic, M., et al., (1991) Nucleotide sequences of the gnd genes from nine natural isolates of *Escherichia coli*: evidence of the intragenic recombination as a contributing factor in the evolution of the polymorphic gnd locus. J. Bacteriol. 173:3894-3900.

Blanco et al., 'Detection of enterohaemorrhagic *Escherichia coli* O157 :H7 in minced beef using immunomagnetic separation' Microbiologia 12(3) : 385-394, 1996. (Abstract).

Database EMBL 'Online!; EMBL; Feb. 18, 1995; Nelson, K.: "*Escherichia coli* E3406 6-phosphogluconate dehydrogenase (gnd) gene, partially cds"; Database accession No. U14443; XP002208387.

Database EMBL 'Online!; EMBL; Jul. 21, 1991; Dykhuizen, D.E. et al.; "*E. coli* (strain ECOR4) 6-phosphogluconate dehydrogenase (gnd) gene, complete cds"; Database accession No. M64324; XP001098200; sequence.

Database EMBL 'Online!; EMBL; Sep. 21, 1994; Nelson, K.: "*Escherichia coli* E811819 6-phosphogluconate dehydrogenase (gnd) gene, partially cds"; Database accession No. U14433; XP002208386;.

Database EMBL 'Online!; EMBL; Sep. 21, 1994; Nelson, K.; "*Escherichia coli* A8190 6-phosphogluconate dehydrogenase (gnd) gene, partially cds"; Database accession No. U14423; XP002208385; sequence.

Database EMBL 'Online!; EMBL; Dykhuizen, D.E. et al.; "*E. coli* (strain ECOR4) 6-phosphogluconate dehydrogenase (gnd) gene, complete cds"; Database accession No. M64328; XP002208389; (1993).

Desmarchelier et al. (J. Clin. Microbial (1998) 36:1801-1804.

Doyle et al., 'Isolation of *Escherichia coli* O157:H7 from Retail Fresh Meats and Poultry' Applied and Environmental Microbiology 53(10): 2394-2396, 1987.

Feldsine et al., 'Assurance Enzyme Immunoassay for Detection of Enterohemorrhagic *Escherichia coli* O157:H7 in Selected Foods: Collaborative Study Journal of AOAC International 80(3): 530-543, 1997.

Feldsine et al., 'Assurance *Escherichia coli* O157:H7: A Comparative Validation Study' Journal of AOAC International 80(1): 37-42, 1997.

Feldsine et al., '*Escherichia coli* 0157:H7 Visual Immunoprecipitate Assay: A Comparative Validation Study' Journal of AOAC International 80(1): 43-48, 1997.

Feldsine et al., 'Visual Immunoprecipitate Assay (VIP) for Detection of Enterohemorrhagic *Escherichia coli* (EHEC) O157:H7 in Selected Foods: Collaborative Study' Journal of AOAC International 80(3): 517-529, 1997.

Feng et al., 'Identification of a Rough Strain of *Escherichia coli* O157:H7 That Produces No. Detectable O157 Antigen' Journal of Clinical Microbiology 36(8): 2339-2341, 1998.

Feng, P., et al. (1998) Genotypic and phenotypic changes in the emergence of *Escherichia coli* O157:H7. J. Infect. Dis. 177:1750-1753.

Fortin et al. Analytical Biochem (2001) 289:281-288.

GenBank Accession No. A74817, 1994.

GenBank Accession No. AA285441, Apr. 1997.

GenBank Accession No. AB008676, 13 pages (1999).

GenBank Accession No. AF061251, 6 pages (1998).

GenBank Accession No. U14423; 1996.

Grif, Katharina, et al., "Comparative study of five different techniques for epidemiological typing of *Escherichia coli* O157"; Diagnostic Microbiology and Infectious Disease, vol. 32, No. 3, Nov. 1998, pp. 165-176, XP002209346; ISSN: 0732-8893.

Gunzer et al., "Molecular Detection of Sorbitol-Fermenting *Escherichia coli* O157 in Patients with Hemolytic-Uremic Syndrome" Journal of Clinical Microbiology 30(7): 1807-1810, 1992.

Hayashi, Tetsuya, DNA Research 8, Nov. 22, 2001.

Jinneman et al., "Comparison of Template Preparation Methods from Foods for Amplification of *Escherichia coli* O157 Shiga-Like Toxins Type I and II DNA by Multiplex Polymerase Chain Reaction" Journal of Food Protection 58(7): 722-726, 1995.

Johnson et al., "Detection of *Escherichia coli* O157:H7 in Meat by an Enzyme-Linked Immunosorbent Assay, EHEC-Tek" Applied and Environmental Microbiology 61(1): 386-388, 1995.

Karch et al., "Isolation of Enterohemorrhagic *Escherichia coli* O157 Strains from Patients with Hemolytic-Uremic Syndrome by Using Immunomagnetic Separation, DNA-Based Methods, and Direct Culture" Journal of Clinical Microbiology 34(3): 516-519, 1996.

Kehl et al., "Evaluation of the Premier EHEC Assay for Detection of Shiga Toxin-Producing *Escherichia coli*" Journal of Clinical Microbiology 35(8): 2051-2054, 1997.

Kim et al., "Dipstick Immunoassay To Detect Enterohemorrhagic *Escherichia coli* O157:H7 in Retail Ground Beef" Applied and Environmental Microbiology 58(5): 1764-1767, 1992.

LeClerc et al., "High Mutation Frequencies Among *Escherichia coli* and Salmonella Pathogens" Science 274: 1208-1211, 1996.

March et al., "Sorbitol-MacConkey Medium for Detection of *Escherichia coli* O157:H7 Associated with Hemorrhagic Colitis" Journal of Clinical Microbiology 23(5): 869-872, 1986.

Marras et al, Genet. Anal.: Biomolec. Eng., (1999)14:151-156.

Maurer et al. Appl. Environ Microbiol. (1999) 65:2954-2960.

Nelson K, Selander RK Proc. Natl. Acad. Sci U.S.A. (1994) 91:10227-10231.

Notermans et al., "DNA hybridization and latex agglutination for detection of heat-labile- and shiga-like toxin-producing *Escherichia coli* in meat" International Journal of Food Microbiology 13: 31-40, 1991.

Notice of Abandonment for U.S. Appl. No. 09/875,573 dated May 31, 2007.

Office Action for U.S. Appl. No. 09/875,573 dated Jan. 22, 2004.

Office Action for U.S. Appl. No. 09/875,573 dated May 24, 2005.

Office Action for U.S. Appl. No. 09/875,573 mailed Oct. 12, 2006.

Office Action in U.S. Appl. No. 11/787,195 dated Apr. 27, 2006.

Office Action in U.S. Appl. No. 11/787,195 dated Sep. 30, 2009.

Okrend et al., "An Improved Screening Method for the Detection and Isolation of *Escherichia coli* O157:H7 From Meat, Incorporating the 3M Petrifilm122 Test Kit 013 HEC 013 for Hemorrhagic *Escherichia coli* O157:H7" J. Food Protect 53: 936-940, 1990.

Padhye et al., "Rapid Procedure for Detecting Enterohemorrhagic *Escherichia coli* O157:H7 in Food" Applied and Environmental Microbiology 57(9): 2693-2698, 1991.

Paton et al., "Detection and Characterization of Shiga Toxigenic *Escherichia coli* by Using Multiplex PCR Assays for stx1, stx2, eaeA, Enterohemorrhagic *E. coli* hlyA, rfbO111, and rfbO157" Journal of Clinical Microbiology 36(2): 598-602, 1998.

Pawelzik, "Pathogenic *Escherichia coli* O157:H7 and their detection" Acta Microbiol. Hung. 38(3-4): 315-320, 1991. (Abstract).

Pfaffl, MW (2001) Nucleic Acids Research 29(9):2002-2007.

Pupo et al.; Infection and Immunity, vol. 65, pp. 2685-2692, Jul. 1997.

Ratnam et al., "Characterization of *Escherichia coli* Serotype O157:H7" Journal of Clinical Microbiology 26(10): 2006-2012, 1988.

Strockbine et al., "Overview of detection and subtyping methods" *Escherichia coli* O157:H7 and other Shiga toxin-producing *E. coli* strains Chapter 33, Kaper and O'Brien, Eds., Washington, D.C.: ASM Press, 1998, 331-356.

Tarr et al., "*Escherichia coli* O157:H7 and the Hemolytic Uremic Syndrome: Importance of Early Cultures in Establishing the Etiology" J. Infect. Dis. 162: 553-556, 1990.

Tarr, P. I. (1995) *Escherichia coli* O157:H7: clinical, diagnostic, and epidemiological aspects of human infection. Clin Infect. Dis. 20:1-8.

Tarr, P. I. et al. (1989) Genotypic variation in pathogenic *Eschericha coli* O157:H7 isolated from patients in Washington 1984-1987. J. Infect. Dis. 159:344-347.

Tarr, P.I., et al. (1999) Acquisition of the rfb-gnd chromosomal region in the divergence of *Escherichia coli* O157:H7 from *E. coli* O55:H7 (Abstract and poster). Annual Meeting of the American Society for Microbiology.

Tortorello et al., "Antibody-Direct Epifluorescent Filter Technique for Rapid, Direct Enumeration of *Escherichia coli* O157:H7 in Beef" Applied and Environmental Microbiology 60(10): 3553-3559, 1994.

Vernozy-Rozand et al., "A shorter enrichment culture for the isolation of *Escherichia coli* O157:H7 from raw minced beef" Revue de Medecine Veterinaire 148(11): 879-882, 1997. (Abstract).

Vernozy-Rozand et al., "An improved procedure for the detection of *Escherichia coli* O157 in food using an automated screening method" Revue de Medecine Veterinaire 149(3): 239-244, 1998. (Abstract).

Vernozy-Rozand et al., "Detection of *Escherichia coli* O157 in French food samples using an immunomagnetic separation method and the VIDAS122 *E. coli* O157" Letters in Applied Microbiology 25: 442-446, 1997.

Wang, L., et al. (1998) Organization of *Escherichia coli* O157 O antigen gene cluster and identification of its specific genes. Infect. Immun. 66:3545-3551.

Whittam et al., "Genetic Polymorphisms and Recombination in Natural Populations of *Escherichia coli*" Mechanisms of Molecular Evolution, Takahata et al., eds. Sinauer Associates, Inc.: Sunderland, MA, 223-245, 1993.

Yu et al., Immunomagnetic-Electrochemiluminescent Detection of *Escherichia coli* O157 and *Salmonella typhimurium* in Foods and Environmental Water Samples Applied and Environmental Microbiology 62(2): 587-592, 1996.

Final Office Action for U.S. Appl. No. 11/787,195 dated May 24, 2011.

Frahm and Obst, "Application of the fluorogenic probe technique (TaqMan PCR) to the detection of *Enterococcus spp.* and *Escherichia coli* in water samples" J. Microbial Methods (2003) 52:123-131.

Marras et al. Genotyping SNPs with molecular beacons, Methods Mol. Biol. 212:111-28, 2003.

Tyagi et al., "Molecular beacons: Probes that fluoresce upon hybridization" Nature Biotechnol. (1996) 14:303-308.

Tyagi et al., "Multicolor molecular beacons for allele discrimination" Nature Biotechnol., (1998) 16:49-53.

Tyagi et al., "Wavelength-shifting molecular beacons" Nature Biotechnology (2000) 18:1191-1196.

Whitcombe et al., "Detection of PCR products using self-probing amplicons and fluorescence" Nature Biotechnol. (1999)17:804-807.

* cited by examiner

| | | |
|---|---|---|
| e-co-b71 | TGGCGCAGGTCACTATGTG | 516 |
| e-co-b73 | TGGCGCAGGTCACTATGTG | 517 |
| e-co-b74 | TGGCGCAGGTCACTATGTG | 515 |
| e-co-b75 | TGGCGCAGGT--------- | 509 |
| e-co-b76 | TGGCGCAGGT--------- | 509 |
| e-co-b81 | TGGCGCAGGTCACTATG-- | 517 |
| e-co-b82 | TGGCGCAGGT--------- | 510 |
| e-co-b84 | TGGCGCAGGTCACTATGTG | 518 |
| e-co-b85 | TGGCCCAGGT--------- | 506 |
| e-co-b86 | TGGCGCAGGTCACT----- | 508 |
| e-co-b168 | TGGCCCAGGTCACTA---- | 507 |
| e-co-b100 | TGGCCCAGGT--------- | 502 |
| e-co-b101 | TGGCCCAGGTCACTATGTG | 511 |
| e-co-b102 | TGGCGCAGGTCACT----- | 506 |
| e-co-b103 | TGTGCAGGTCATT------ | 508 |
| e-co-b104 | TGGTGCAGGTCATT----- | 508 |
| e-co-b110 | TGGTCCAGGTCATTAC--- | 513 |
| | TGGcCCAGGT | | dG = −3.9

```
e-co-b71  : TGCCCGCAGGTCACTATGTG : 516
e-co-b73  : TCGCCGCAGGTCACTATGTG : 517
e-co-b74  : TGCCCGCAGGTCACTATGTG : 515
e-co-b75  : TGGCCGCAGGT--------- : 509
e-co-b76  : TGCCCGCAGGT--------- : 509
e-co-b81  : TGCCCGCAGGTCACTATG-- : 517
e-co-b82  : TGGCCGCAGGT--------- : 510
e-co-b84  : TGCCCGCAGGTCACTATGTG : 518
e-co-b85  : TGCCCGCAGGT--------- : 506
e-co-b86  : TGCCCGCAGGTCACT----- : 508
e-co-b168 : TGGCCGCAGGTCACTA---- : 507
e-co-b100 : TGCCCGCAGGT--------- : 502
e-co-b101 : TGGCCGCAGGTCACTATGTG : 511
e-co-b102 : TGGCGCAGGTCACT------ : 506
e-co-b103 : TCGTCCAGGTCATT------ : 508
e-co-b104 : TGGTCCAGGTCATT------ : 508
e-co-b110 : TGGTGCAGGTCATTAC---- : 513
            TGGCCCAGGT
``` dG = −2.9

ATGTCAAAGCAACAGATCGGCGTAGTCGGTATGGCAGTGATGGGGCGCAA
CCTTGCGCTCAACATCGAAAGCCGTGGTTATACCGTCTCTATTTTCAACCG
TTCCCGTGAAAAGACGGAAGAAGTGATTGCCGAAAATCCAGGCAAGAAA
CTGGTTCCTTACTATACGGTGAAAGAATTTGTTGAATCTCTGGAAACGCCT
CGTCGCATCTTGTTAATGGTGAAAGCAGGTGCAGGCACGGATGCTGCTAT
TGATTCCCTTAAGCCATACCTCGATAAAGGTGACATCATCATTGATGGTGG
TAATACCTTCTTCCAGGACACCATTCGTCGTAACCGTGAGCTTTCTGCAGA
AGGCTTTAACTTCATCGGTACCGGTGTTTCCGGTGGTGAGGAGGGCGCAC
TAAAAGGTCCTTCCATTATGCCTGGTGGGCAGAAAGAAGCCTATGAACTA
GTTGCGCCGATCCTGACCAAAATCGCCGCAGTGGCTGAAGACGGTGAGCC
ATGCGTTACCTATATTGGTGCCGATGGCGCAGGTCACTATGTGAAGATGG
TTCACAACGGTATTGAATACGGCGATATGCAGCTGATTGCTGAAGCCTATT
CTCTGCTTAAAGGTGGTCTGAACCTCACCAACGAAGAACTGGCGCAGATC
TTTACCGAGTGGAATAACGGTGAACTGAGCAGCTACCTGATCGACATTAC
CAAAGACATCTTCACTAAAAAAGATGAAGACGGTAACTACCTGGTTGATG
TGATCCTGGATGAAGCGGCAAACAAAGGTACGGGCAAATGGACCAGCCA
GAGCGCACTGGATCTCGGCGAACCGCTGTCGCTGATTACCGAGTCTGTGTT
TGCACGATACATCTCTTCTCTGAAAGATCAGCGCGTTGCTGCGTCTAAAGT
TCTCTCTGGCCCACAAGCGCAGCCAGCTGGCGACAAGGCTGAGTTCATCG
AAAAAGTTCGCCGTGCACTGTATCTGGGCAAAATCGTTTCTTACGCTCAGG
GGTTCTCTCAACTGCGTGCGGCGTCTGAAGAGTACAACTGGGATCTGAAC
TACGGCGAAATCGCGAAGATTTTCCGTGCTGGCTGCATCATCCGTGCGCA
GTTCCTGCAGAAAATCACCGATGCTTATGCCGAAAATCCGCAGATCGCTA
ACCTGCTGCTGGCTCCTTACTTCAAGCAAATTGCCGATGACTACCAGCAGG
CGCTGCGCGATGTCGTCGCTTATGCGGTACAGAACGGTATCCCGGTTCCG
ACCTTCGCCGCTGCGGTTGCCTATTATGACAGCTACCGCGCCGCTGTTCTG
CCTGCGAACCTGATCCAGGCACAGCGTGACTATTTCGGTGCGCATACTTAT
AAGCGCATTGATAAAGAAGGTGTGTTCCATACCGAATGGCTGGATTAA

B.

AGGAGGGCGCACTAAAAGGTCCTTCCATTATGCCTGGTGGGCAGAAAGAA
GCCTATGAACTAGTTGCGCCGATCC

C.

CCTGGTGGGCAGAAAGAAGCC

ATGTCAAAGCAACAGATCGGCGTAGTCGGTATGGCAGTGATGGGGCGCAA
CCTTGCGCTCAACATCGAAAGCCGTGGTTATACCGTCTCTATTTTCAACCG
TTCCCGTGAAAAGACGGAAGAAGTGATTGCCGAAAATCCAGGCAAGAAA
CTGGTTCCTTACTATACGGTGAAAGAATTTGTTGAATCTCTGGAAACGCCT
CGTCGCATCTTGTTAATGGTGAAAGCAGGTGCAGGCACGGATGCTGCTAT
TGATTCCCTTAAGCCATACCTCGATAAAGGTGACATCATCATTGATGGTGG
TAATACCTTCTTCCAGGACACCATTCGTCGTAACCGTGAGCTTTCTGCAGA
AGGCTTTAACTTCATCGGTACCGGTGTTTCCGGTGGTGAGGAGGGCGCAC
TAAAAGGTCCTTCCATTATGCCTGGTGGGCAGAAAGAAGCCTATGAACTA
GTTGCGCCGATCCTGACCAAAATCGCCGCAGTGGCTGAAGACGGTGAGCC
ATGCGTTACCTATATTGGTGCCGATGGCGCAGGTCACTATGTGAAGATGG
TTCACAACGGTATTGAATACGGCGATATGCAGCTGATTGCTGAAGCCTATT
CTCTGCTTAAAGGTGGTCTGAACCTCACCAACGAAGAACTGGCGCAGATC
TTTACCGAGTGGAATAACGGTGAACTGAGCAGCTACCTGATCGACATTAC
CAAAGACATCTTCACTAAAAAGATGAAGACGGTAACTACCTGGTTGATG
TGATCCTGGATGAAGCGGCAAACAAAGGTACGGGCAAATGGACCAGCCA
GAGCGCACTGGATCTCGGCGAACCGCTGTCGCTGATTACCGAGTCTGTGTT
TGCACGATACATCTCTTCTCTGAAAGATCAGCGCGTTGCTGCGTCTAAAGT
TCTCTCTGGCCCACAAGCGCAGCCAGCTGGCGACAAGGCTGAGTTCATCG
AAAAAGTTCGCCGTGCACTGTATCTGGGCAAAATCGTTTCTTACGCTCAGG
GGTTCTCTCAACTGCGTGCGGCGTCTGAAGAGTACAACTGGGATCTGAAC
TACGGCGAAATCGCGAAGATTTTCCGTGCTGGCTGCATCATCCGTGCGCA
GTTCCTGCAGAAAATCACCGATGCTTATGCCGAAAATCCGCAGATCGCTA
ACCTGCTGCTGGCTCCTTACTTCAAGCAAATTGCCGATGACTACCAGCAGG
CGCTGCGCGATGTCGTCGCTTATGCGGTACAGAACGGTATCCCGGTTCCG
ACCTTCGCCGCTGCGGTTGCCTATTATGACAGCTACCGCGCCGCTGTTCTG
CCTGCGAACCTGATCCAGGCACAGCGTGACTATTTCGGTGCGCATACTTAT
AAGCGCATTGATAAAGAAGGTGTGTTCCATACCGAATGGCTGGATTAA

B.

GCCTCGTCGCATCTTGTTAATGGTGAAAGCAGGTGCAGGCACGGATGCTG
CTATTGATTCCCTTAAGCCATACCTCGATAAAGGTGACATCATCATTGATG
GTGGTAATACCTTCTTCCAGGACACCATTCGTCGTAACCGTGAGCTTTCTG
CAGAAGGCTTTAACTTCATCGGTACCGGTGTTTCCGGTGGTGAGGAGGGC
GCACTA

C.

CAGGCACGGATGCTGCTATTGATTCCCT

ATGTCAAAGCAACAGATCGGCGTAGTCGGTATGGCAGTGATGGGGCGCAA
CCTTGCGCTCAACATCGAAAGCCGTGGTTATACCGTCTCTATTTTCAACCG
TTCCCGTGAAAAGACGGAAGAAGTGATTGCCGAAAATCCAGGCAAGAAA
CTGGTTCCTTACTATACGGTGAAAGAATTTGTTGAATCTCTGGAAACGCCT
CGTCGCATCTTGTTAATGGTGAAAGCAGGTGCAGGCACGGATGCTGCTAT
TGATTCCCTTAAGCCATACCTCGATAAAGGTGACATCATCATTGATGGTGG
TAATACCTTCTTCCAGGACACCATTCGTCGTAACCGTGAGCTTTCTGCAGA
AGGCTTTAACTTCATCGGTACCGGTGTTTCCGGTGGTGAGGAGGGCGCAC
TAAAAGGTCCTTCCATTATGCCTGGTGGGCAGAAAGAAGCCTATGAACTA
GTTGCGCCGATCCTGACCAAAATCGCCGCAGTGGCTGAAGACGGTGAGCC
ATGCGTTACCTATATTGGTGCCGATGGCGCAGGTCACTATGTGAAGATGG
TTCACAACGGTATTGAATACGGCGATATGCAGCTGATTGCTGAAGCCTATT
CTCTGCTTAAAGGTGGTCTGAACCTCACCAACGAAGAACTGGCGCAGATC
TTTACCGAGTGGAATAACGGTGAACTGAGCAGCTACCTGATCGACATTAC
CAAAGACATCTTCACTAAAAAGATGAAGACGGTAACTACCTGGTTGATG
TGATCCTGGATGAAGCGGCAAACAAAGGTACGGGCAAATGGACCAGCCA
GAGCGCACTGGATCTCGGCGAACCGCTGTCGCTGATTACCGAGTCTGTGTT
TGCACGATACATCTCTTCTCTGAAAGATCAGCGCGTTGCTGCGTCTAAAGT
TCTCTCTGGCCCACAAGCGCAGCCAGCTGGCGACAAGGCTGAGTTCATCG
AAAAAGTTCGCCGTGCACTGTATCTGGGCAAAATCGTTTCTTACGCTCAGG
GGTTCTCTCAACTGCGTGCGGCGTCTGAAGAGTACAACTGGGATCTGAAC
TACGGCGAAATCGCGAAGATTTTCCGTGCTGGCTGCATCATCCGTGCGCA
GTTCCTGCAGAAAATCACCGATGCTTATGCCGAAAATCCGCAGATCGCTA
ACCTGCTGCTGGCTCCTTACTTCAAGCAAATTGCCGATGACTACCAGCAGG
CGCTGCGCGATGTCGTCGCTTATGCGGTACAGAACGGTATCCCGGTTCCG
ACCTTCGCCGCTGCGGTTGCCTATTATGACAGCTACCGCGCCGCTGTTCTG
CCTGCGAACCTGATCCAGGCACAGCGTGACTATTTCGGTGCGCATACTTAT
AAGCGCATTGATAAAGAAGGTGTGTTCCATACCGAATGGCTGGATTAA

B.

GCCTCGTCGCATCTTGTTAATGGTGAAAGCAGGTGCAGGCACGGATGCTG
CTATTGATTCCCTTAAGCCATACCTCGATAAAGGTGACATCATCATTGATG
GTGGTAATACCTTCTTCCAGGACACCATTCGTCGTAACCGTGAGCTTTCTG
CAGAAGGCTTTAACTTCATCGGTACCGGTGTTTCCGGTGGTGAGGAGGGC
GCACTAAAAGGTCCTTCCATTATGCCTGGTGGGCAGAAAGAAGCCTATGA
ACTAGTTGCGCCGATCC

```
                        SEQUENCE LISTING

<160> NUMBER OF SEQ ID NOS: 43

<210> SEQ ID NO 1
<211> LENGTH: 1407
<212> TYPE: DNA
<213> ORGANISM: Escherichia coli
<220> FEATURE:
<223> OTHER INFORMATION: O157:H7 gnd (AE005174)

<400> SEQUENCE: 1
atgtcaaagc aacagatcgg cgtagtcggt atggcagtga tggggcgcaa ccttgcgctc      60
aacatcgaaa gccgtggtta taccgtctct attttcaacc gttcccgtga aaagacggaa     120
gaagtgattg ccgaaaatcc aggcaagaaa ctggttcctt actatacggt gaaagaattt     180
gttgaatctc tggaaacgcc tcgtcgcatc ttgttaatgg tgaaagcagg tgcaggcacg     240
gatgctgcta ttgattccct taagccatac ctcgataaag gtgacatcat cattgatggt     300
ggtaatacct tcttccagga caccattcgt cgtaaccgtg agctttctgc agaaggcttt     360
aacttcatcg gtaccggtgt ttccggtggt gaggagggcg cactaaaagg tccttccatt     420
atgcctggtg ggcagaaaga agcctatgaa ctagttgcgc cgatcctgac caaaatcgcc     480
gcagtggctg aagacggtga gccatgcgtt acctatattg gtgccgatgg cgcaggtcac     540
tatgtgaaga tggttcacaa cggtattgaa tacggcgata tgcagctgat tgctgaagcc     600
tattctctgc ttaaaggtgg tctgaacctc accaacgaag aactggcgca gatctttacc     660
gagtggaata acggtgaact gagcagctac ctgatcgaca ttaccaaaga catcttcact     720
```

| | |
|---|---:|
| aaaaaagatg aagacggtaa ctacctggtt gatgtgatcc tggatgaagc ggcaaacaaa | 780 |
| ggtacgggca aatggaccag ccagagcgca ctggatctcg gcgaaccgct gtcgctgatt | 840 |
| accgagtctg tgtttgcacg atacatctct tctctgaaag atcagcgcgt tgctgcgtct | 900 |
| aaagttctct ctggcccaca agcgcagcca gctggcgaca aggctgagtt catcgaaaaa | 960 |
| gttcgccgtg cactgtatct gggcaaaatc gtttcttacg ctcaggggtt ctctcaactg | 1020 |
| cgtgcggcgt ctgaagagta caactgggat ctgaactacg cgaaatcgc gaagattttc | 1080 |
| cgtgctggct gcatcatccg tgcgcagttc ctgcagaaaa tcaccgatgc ttatgccgaa | 1140 |
| aatccgcaga tcgctaacct gctgctggct ccttacttca gcaaattgc cgatgactac | 1200 |
| cagcaggcgc tgcgcgatgt cgtcgcttat gcggtacaga acggtatccc ggttccgacc | 1260 |
| ttcgccgctg cggttgccta ttatgacagc taccgcgccg ctgttctgcc tgcgaacctg | 1320 |
| atccaggcac agcgtgacta tttcggtgcg catacttata agcgcattga taaagaaggt | 1380 |
| gtgttccata ccgaatggct ggattaa | 1407 |

<210> SEQ ID NO 2
<211> LENGTH: 516
<212> TYPE: DNA
<213> ORGANISM: Escherichia coli
<220> FEATURE:
<223> OTHER INFORMATION: O157:H7 e-co-b71

<400> SEQUENCE: 2

| | |
|---|---:|
| atggcagtga tggggcgcaa ccttgcgctc aacatcgaaa gccgtggtta taccgtctct | 60 |
| attttcaacc gttcccgtga aaagacggaa gaagtgattg ccgaaaatcc aggcaagaaa | 120 |
| ctggttcctt actatacggt gaaagaattt gttgaatctc tggaaacgcc tcgtcgcatc | 180 |
| ttgttaatgg tgaaagcagg tgcaggcacg gatgctgcta ttgattccct taagccatac | 240 |
| ctcgataaag gtgacatcat cattgatggt ggtaatacct tcttccagga caccattcgt | 300 |
| cgtaaccgtg agctttctgc agaaggcttt aacttcatcg gtaccggtgt ttccggtggt | 360 |
| gaggagggcg cactaaaagg tccttccatt atgcctggtg ggcagaaaga agcctatgaa | 420 |
| ctagttgcgc cgatcctgac caaaatcgcc gcagtggctg aagacggtga gccatgcgtt | 480 |
| acctatattg gtgccgatgg cgcaggtcac tatgtg | 516 |

<210> SEQ ID NO 3
<211> LENGTH: 517
<212> TYPE: DNA
<213> ORGANISM: Escherichia coli
<220> FEATURE:
<223> OTHER INFORMATION: O157:H7 e-co-b73

<400> SEQUENCE: 3

| | |
|---|---:|
| tatggcagtg atggggcgca accttgcgct caacatcgaa agccgtggtt ataccgtctc | 60 |
| tattttcaac cgttcccgtg aaaagacgga agaagtgatt gccgaaaatc caggcaagaa | 120 |
| actggttcct tactatacgg tgaaagaatt tgttgaatct ctggaaacgc ctcgtcgcat | 180 |
| cttgttaatg gtgaaagcag gtgcaggcac ggatgctgct attgattccc ttaagccata | 240 |
| cctcgataaa ggtgacatca tcattgatgg tggtaatacc ttcttccagg acaccattcg | 300 |
| tcgtaaccgt gagctttctg cagaaggctt taacttcatc ggtaccggtg tttccggtgg | 360 |
| tgaggagggc gcactaaaag gtccttccat tatgcctggt gggcagaaag aagcctatga | 420 |
| actagttgcg ccgatcctga ccaaaatcgc cgcagtggct gaagacggtg agccatgcgt | 480 |
| tacctatatt ggtgccgatg gcgcaggtca ctatgtg | 517 |

<210> SEQ ID NO 4
<211> LENGTH: 515
<212> TYPE: DNA
<213> ORGANISM: Escherichia coli
<220> FEATURE:
<223> OTHER INFORMATION: O157:H7 e-co-b74

<400> SEQUENCE: 4

| | | | | | |
|---|---|---|---|---|---|
| tggcagtgat | ggggcgcaac | cttgcgctca | acatcgaaag | ccgtggttat | accgtctcta | 60 |
| ttttcaaccg | ttcccgtgaa | agacggaag | aagtgattgc | cgaaaatcca | ggcaagaaac | 120 |
| tggttcctta | ctatacggtg | aaagaatttg | ttgaatctct | ggaaacgcct | cgtcgcatct | 180 |
| tgttaatggt | gaaagcaggt | gcaggcacgg | atgctgctat | tgattcccctt | aagccatacc | 240 |
| tcgataaagg | tgacatcatc | attgatggtg | gtaataccctt | cttccaggac | accattcgtc | 300 |
| gtaaccgtga | gctttctgca | gaaggcttta | acttcatcgg | taccggtgtt | ccggtggtg | 360 |
| aggagggcgc | actaaaaggt | ccttccatta | tgcctggtgg | gcagaaagaa | gcctatgaac | 420 |
| tagttgcgcc | gatcctgacc | aaaatcgccg | cagtggctga | agacggtgag | ccatgcgtta | 480 |
| cctatattgg | tgccgatggc | gcaggtcact | atgtg | | | 515 |

<210> SEQ ID NO 5
<211> LENGTH: 509
<212> TYPE: DNA
<213> ORGANISM: Escherichia coli
<220> FEATURE:
<223> OTHER INFORMATION: O157:H7 e-co-b75

<400> SEQUENCE: 5

| | | | | | |
|---|---|---|---|---|---|
| gtatggcagt | gatggggcgc | aaccttgcgc | tcaacatcga | aagccgtggt | tataccgtct | 60 |
| ctattttcaa | ccgttcccgt | gaaaagacgg | aagaagtgat | tgccgaaaat | ccaggcaaga | 120 |
| aactggttcc | ttactatacg | gtgaaagaat | ttgttgaatc | tctggaaacg | cctcgtcgca | 180 |
| tcttgttaat | ggtgaaagca | ggtgcaggca | cggatgctgc | tattgattcc | cttaagccat | 240 |
| acctcgataa | aggtgacatc | atcattgatg | gtggtaatac | cttcttccag | gacaccattc | 300 |
| gtcgtaaccg | tgagctttct | gcagaaggct | ttaacttcat | cggtaccggt | gtttccggtg | 360 |
| gtgaggaggg | cgcactaaaa | ggtccttcca | ttatgcctgg | tgggcagaaa | gaagcctatg | 420 |
| aactagttgc | gccgatcctg | accaaaatcg | ccgcagtggc | tgaagacggt | gagccatgcg | 480 |
| ttacctatat | tggtgccgat | ggcgcaggt | | | | 509 |

<210> SEQ ID NO 6
<211> LENGTH: 509
<212> TYPE: DNA
<213> ORGANISM: Escherichia coli
<220> FEATURE:
<223> OTHER INFORMATION: O157:H7 e-co-b76

<400> SEQUENCE: 6

| | | | | | |
|---|---|---|---|---|---|
| gtatggcagt | gatggggcgc | aaccttgcgc | tcaacatcga | aagccgtggt | tataccgtct | 60 |
| ctattttcaa | ccgttcccgt | gaaaagacgg | aagaagtgat | tgccgaaaat | ccaggcaaga | 120 |
| aactggttcc | ttactatacg | gtgaaagaat | ttgttgaatc | tctggaaacg | cctcgtcgca | 180 |
| tcttgttaat | ggtgaaagca | ggtgcaggca | cggatgctgc | tattgattcc | cttaagccat | 240 |
| acctcgataa | aggtgacatc | atcattgatg | gtggtaatac | cttcttccag | gacaccattc | 300 |
| gtcgtaaccg | tgagctttct | gcagaaggct | ttaacttcat | cggtaccggt | gtttccggtg | 360 |
| gtgaggaggg | cgcactaaaa | ggtccttcca | ttatgcctgg | tgggcagaaa | gaagcctatg | 420 |

```
aactagttgc gccgatcctg accaaaatcg ccgcagtggc tgaagacggt gagccatgcg    480
ttacctatat tggtgccgat ggcgcaggt                                       509
```

<210> SEQ ID NO 7
<211> LENGTH: 517
<212> TYPE: DNA
<213> ORGANISM: Escherichia coli
<220> FEATURE:
<223> OTHER INFORMATION: O157:H7 e-co-b81

<400> SEQUENCE: 7

```
ggtatggcag tgatggggcg caaccttgcg ctcaacatcg aaagccgtgg ttataccgtc     60
tctattttca accgttcccg tgaaaagacg gaagaagtga ttgccgaaaa tccaggcaag    120
aaactggttc cttactatac ggtgaaagaa tttgttgaat ctctggaaac gcctcgtcgc    180
atcttgttaa tggtgaaagc aggtgcaggc acggatgctg ctattgattc ccttaagcca    240
tacctcgata aggtgacat catcattgat ggtggtaata ccttcttcca ggacaccatt     300
cgtcgtaacc gtgagctttc tgcagaaggc tttaacttca tcggtaccgg tgtttccggt    360
ggtgaggagg gcgcactaaa aggtccttcc attatgcctg gtgggcagaa agaagcctat    420
gaactagttg cgccgatcct gaccaaaatc gccgcagtgg ctgaagacgg tgagccatgc    480
gttacctata ttggtgccga tggcgcaggt cactatg                             517
```

<210> SEQ ID NO 8
<211> LENGTH: 510
<212> TYPE: DNA
<213> ORGANISM: Escherichia coli
<220> FEATURE:
<223> OTHER INFORMATION: O157:H7 e-co-b82

<400> SEQUENCE: 8

```
ggtatggcag tgatggggcg caaccttgcg ctcaacatcg aaagccgtgg ttataccgtc     60
tctattttca accgttcccg tgaaaagacg gaagaagtga ttgccgaaaa tccaggcaag    120
aaactggttc cttactatac ggtgaaagaa tttgttgaat ctctggaaac gcctcgtcgc    180
atcttgttaa tggtgaaagc aggtgcaggc acggatgctg ctattgattc ccttaagcca    240
tacctcgata aggtgacat catcattgat ggtggtaata ccttcttcca ggacaccatt     300
cgtcgtaacc gtgagctttc tgcagaaggc tttaacttca tcggtaccgg tgtttccggt    360
ggtgaggagg gcgcactaaa aggtccttcc attatgcctg gtgggcagaa agaagcctat    420
gaactagttg cgccgatcct gaccaaaatc gccgcagtgg ctgaagacgg tgagccatgc    480
gttacctata ttggtgccga tggcgcaggt                                      510
```

<210> SEQ ID NO 9
<211> LENGTH: 518
<212> TYPE: DNA
<213> ORGANISM: Escherichia coli
<220> FEATURE:
<223> OTHER INFORMATION: O157:H7 e-co-b84

<400> SEQUENCE: 9

```
gtatggcagt gatggggcgc aaccttgcgc tcaacatcga aagccgtggt tataccgtct     60
ctattttcaa ccgttcccgt gaaaagacgg aagaagtgat tgccgaaaat ccaggcaaga    120
aactggttcc ttactatacg gtgaaagaat ttgttgaatc tctggaaacg cctcgtcgca    180
tcttgttaat ggtgaaagca ggtgcaggca cggatgctgc tattgattcc cttaagccat    240
acctcgataa aggtgacatc atcattgatg gtggtaatac cttcttccag gacaccattc    300
```

| | |
|---|---|
| gtcgtaaccg tgagctttct gcagaaggct ttaacttcat cggtaccggt gtttccggtg | 360 |
| gtgaggaggg cgcactaaaa ggtccttcca ttatgcctgg tgggcagaaa gaagcctatg | 420 |
| aactagttgc gccgatcctg accaaaatcg ccgcagtggc tgaagacggt gagccatgcg | 480 |
| ttacctatat tggtgccgat ggcgcaggtc actatgtg | 518 |

<210> SEQ ID NO 10
<211> LENGTH: 506
<212> TYPE: DNA
<213> ORGANISM: Escherichia coli
<220> FEATURE:
<223> OTHER INFORMATION: O517:H7 e-co-b85

<400> SEQUENCE: 10

| | |
|---|---|
| tggcagtgat ggggcgcaac cttgcgctca acatcgaaag ccgtggttat accgtctcta | 60 |
| ttttcaaccg ttcccgtgaa aagacggaag aagtgattgc cgaaaatcca ggcaagaaac | 120 |
| tggttcctta ctatacggtg aaagaatttg ttgaatctct ggaaacgcct cgtcgcatct | 180 |
| tgttaatggt gaaagcaggt gcaggcacgg atgctgctat tgattccctt aagccatacc | 240 |
| tcgataaagg tgacatcatc attgatggtg gtaataccct tcttccaggac accattcgtc | 300 |
| gtaaccgtga gctttctgca aaggctttta acttcatcgg taccggtgtt tccggtggtg | 360 |
| aggagggcgc actaaaaggt ccttccatta tgcctggtgg gcagaaagaa gcctatgaac | 420 |
| tagttgcgcc gatcctgacc aaaatcgccg cagtggctga agacggtgag ccatgcgtta | 480 |
| cctatattgg tgccgatggc gcaggt | 506 |

<210> SEQ ID NO 11
<211> LENGTH: 508
<212> TYPE: DNA
<213> ORGANISM: Escherichia coli
<220> FEATURE:
<223> OTHER INFORMATION: O157:H7 e-co-b86

<400> SEQUENCE: 11

| | |
|---|---|
| gcagtgatgg ggcgcaacct tgcgctcaac atcgaaagcc gtggttatac cgtctctatt | 60 |
| ttcaaccgtt cccgtgaaaa gacggaagaa gtgattgccg aaaatccagg caagaaactg | 120 |
| gttccttact atacggtgaa agaatttgtt gaatctctgg aaacgcctcg tcgcatcttg | 180 |
| ttaatggtga aagcaggtgc aggcacggat gctgctattg attcccttaa gccatacctc | 240 |
| gataaaggtg acatcatcat tgatggtggt aataccttct tccaggacac cattcgtcgt | 300 |
| aaccgtgagc tttctgcaga aggctttaac ttcatcggta ccggtgtttc cggtggtgag | 360 |
| gagggcgcac taaaaggtcc ttccattatg cctggtgggc agaaagaagc ctatgaacta | 420 |
| gttgcgccga tcctgaccaa aatcgccgca gtggctgaag acggtgagcc atgcgttacc | 480 |
| tatattggtg ccgatggcgc aggtcact | 508 |

<210> SEQ ID NO 12
<211> LENGTH: 507
<212> TYPE: DNA
<213> ORGANISM: Escherichia coli
<220> FEATURE:
<223> OTHER INFORMATION: O1:H30 e-co-b168

<400> SEQUENCE: 12

| | |
|---|---|
| agtgatgggg cgcaaccttg cgctcaacat cgaaagccgt ggttataccg tctctatttt | 60 |
| caaccgttcc cgtgaaaaga cggaagaagt gattgccgaa atccaggca agaaactggt | 120 |
| tccttactat acggtgaaag aatttgttga atctctggaa acgcctcgtc gcatcctgtt | 180 |

-continued

```
aatggtgaaa gcaggtgcag gcacggatgc tgctattgat tcccttaagc catacctcga        240
taaaggtgac atcatcattg atggtggtaa taccttcttc caggacacca ttcgtcgtaa        300
ccgtgagctt tctgcagaag gctttaactt catcggtacc ggtgtttccg gtggtgagga        360
gggcgcacta aaaggtcctt ccattatgcc tggtgggcag aaagaagcct atgaactggt        420
tgcgccgatc ctgaccaaaa tcgccgcagt ggctgaagac ggtgagccat gcgttaccta        480
tattggtgcc gatggcgcag gtcacta                                           507
```

<210> SEQ ID NO 13
<211> LENGTH: 502
<212> TYPE: DNA
<213> ORGANISM: Escherichia coli
<220> FEATURE:
<223> OTHER INFORMATION: O157:H43 e-co-b100

<400> SEQUENCE: 13

```
agtgatgggg cgcaacctag cgctcaacat cgaaagccgt ggttataccg tctctatttt        60
caaccgctcc cgtgagaaga cggaagaagt gattgccgaa atccaggca agaaactggt        120 tccttactat acggtgaaag agtttgttga atctctggaa acgcctcgtc gcatcctgtt        180
aatggtgaaa gcaggtgcag gcacggatgc tgctattgat tccctcaagc cgtacctcga        240
taaaggtgac atcatcattg atggtggtaa caccttcttc caggacacca ttcgtcgtaa        300
ccgtgagctt tctgccgaag gctttaactt catcggtacc ggtgtttccg gcggagaaga        360
aggcgcgctg aaaggtcctt ccattatgcc tggtgggcag aaagaagcct atgaactggt        420
tgcgccgatc ctgaccaaaa tcgccgcagt ggctgaagac ggtgagccat gcgttaccta        480
tattggtgcc gatggcgcag gt                                                502
```

<210> SEQ ID NO 14
<211> LENGTH: 511
<212> TYPE: DNA
<213> ORGANISM: Escherichia coli
<220> FEATURE:
<223> OTHER INFORMATION: O1:H- non-motile e-co-b101

<400> SEQUENCE: 14

```
agtgatgggg cgcaacctag cgctcaacat cgaaagccgt ggttataccg tctctatttt        60
caaccgctcc cgtgagaaga cggaagaagt gattgccgaa atccaggca agaaactggt        120 tccttactat acggtgaaag agtttgttga atctctggaa acgcctcgtc gcatcctgtt        180
aatggtgaaa gcaggtgcag gcacggatgc tgctattgat tccctcaagc cgtacctcga        240
taaaggtgac atcatcattg atggtggtaa caccttcttc caggacacca ttcgtcgtaa        300
ccgtgagctt tctgccgaag gctttaactt catcggtacc ggtgtttccg gcggagaaga        360
aggcgcgctg aaaggtcctt ccattatgcc tggtgggcag aaagaagcct atgaactggt        420
tgcgccgatc ctgaccaaaa tcgccgcagt ggctgaagac ggtgagccat gcgttaccta        480
tattggtgcc gatggcgcag gtcactatgt g                                      511
```

<210> SEQ ID NO 15
<211> LENGTH: 506
<212> TYPE: DNA
<213> ORGANISM: Escherichia coli
<220> FEATURE:
<223> OTHER INFORMATION: O1:H- non-motile e-co-b102

<400> SEQUENCE: 15

```
agtgatgggg cgcaacctag cgctcaacat cgaaagccgt ggttataccg tctctatttt        60
```

```
caaccgctcc cgtgagaaga cggaagaagt gattgccgaa atccaggca agaaactggt    120 tccttactat acggtgaaag agtttgttga atctctggaa acgccgtcgtc gcatcctgtt   180 aatggtgaaa gcaggtgcag gcacggatgc tgctattgat tccctcaagc cgtacctcga   240
taaaggtgac atcatcattg atggtggtaa caccttcttc caggacacca ttcgtcgtaa   300
ccgtgagctt tctgccgaag ctttaacttt catcggtacc ggtgtttccg gcggagaaga   360
aggcgcgctg aaaggtcctt ccattatgcc tggtgggcag aaagaagcct atgaactggt   420
tgcgccgatc ctgaccaaaa tcgccgcagt ggctgaagac ggtgagccat gcgttaccta   480
tattggtgcc gatggcgcag gtcact                                        506

<210> SEQ ID NO 16
<211> LENGTH: 508
<212> TYPE: DNA
<213> ORGANISM: Escherichia coli
<220> FEATURE:
<223> OTHER INFORMATION: O55:H6 e-co-b103

<400> SEQUENCE: 16
gctgtgatgg ggcgcaactt ggctctaaac atcgagagcc gtggttatac cgtatccgtc    60
tataatcgct cgcgtgaaaa aactgaagag gttgttgccg aaaacccagg taagaaactg   120
gtcccttatt acacggttaa agagttcgtc gagtctcttg aaactccacg ccgtatcctg   180
ttaatggtca agcgggtgc tggcactgat gctgcgatta attccctgaa gccctatcta   240
gataaaggcg acatcatcat tgatggcggt aataccttct ttcaggacac aattcgtcgt   300
aaccgtgaac tttccgcgga aggctttaac tttatcgggg ccggggtttc aggtggtgaa   360
gagggcgcgc tgaaaggccc atctatcatg cctggtggcc agaaagatgc gtatgaaatg   420
gttgtgccaa tcctgaccaa gattgccgcg atagctgaag atggtgaacc gtgcgtgacg   480
tatattggtg cggatggtgc aggtcatt                                      508

<210> SEQ ID NO 17
<211> LENGTH: 508
<212> TYPE: DNA
<213> ORGANISM: Escherichia coli
<220> FEATURE:
<223> OTHER INFORMATION: O55:H6 e-co-b104

<400> SEQUENCE: 17
gctgtgatgg ggcgcaactt ggctctaaac atcgagagcc gtggttatac cgtatccgtc    60
tataatcgct cgcgtgaaaa aactgaagag gttgttgccg aaaacccagg taagaaactg   120
gtcccttatt acacggttaa agagttcgtc gagtctcttg aaactccacg ccgtatcctg   180
ttaatggtca agcgggtgc tggcactgat gctgcgatta attccctgaa gccctatcta   240
gataaaggcg acatcatcat tgatggcggt aataccttct ttcaggacac aattcgtcgt   300
aaccgtgaac tttccgcgga aggctttaac tttatcgggg ccggggtttc aggtggtgaa   360
gagggcgcgc tgaaaggccc atctatcatg cctggtggcc agaaagatgc gtatgaaatg   420
gttgtgccaa tcctgaccaa gattgccgcg atagctgaag atggtgaacc gtgcgtgacg   480
tatattggtg cggatggtgc aggtcatt                                      508

<210> SEQ ID NO 18
<211> LENGTH: 513
<212> TYPE: DNA
<213> ORGANISM: Escherichia coli
<220> FEATURE:
<223> OTHER INFORMATION: O55:H6 e-co-b110
```

-continued

```
<400> SEQUENCE: 18
atggctgtga tggggcgcaa cttggctcta aacatcgaga gccgtggtta taccgtatcc    60
gtctataatc gctcgcgtga aaaaactgaa gaggttgttg ccgaaaaccc aggtaagaaa   120
ctggtccctt attacacggt taaagagttc gtcgagtctc ttgaaactcc acgccgtatc   180
ctgttaatgg tcaaagcggg tgctggcact gatgctgcga ttaattccct gaagccctat   240
ctagataaag cgacatcat cattgatggc ggtaatacct tctttcagga cacaattcgt    300
cgtaaccgtg aactttccgc ggaaggcttt aactttatcg gggccggggt ttcaggtggt   360
gaagagggcg cgctgaaagg cccatctatc atgcctggtg ccagaaaga tgcgtatgaa    420 atggttgtgc caatcctgac caagattgcc gcgatagctg aagatggtga accgtgcgtg   480
acgtatattg gtgcggatgg tgcaggtcat tac                                513

<210> SEQ ID NO 19
<211> LENGTH: 75
<212> TYPE: DNA
<213> ORGANISM: Escherichia coli
<220> FEATURE:
<223> OTHER INFORMATION: O157:H7 gnd conserved sequence #1

<400> SEQUENCE: 19
aggagggcgc actaaaaggt ccttccatta tgcctggtgg cagaaagaa gcctatgaac    60 tagttgcgcc gatcc                                                     75

<210> SEQ ID NO 20
<211> LENGTH: 21
<212> TYPE: DNA
<213> ORGANISM: Escherichia coli
<220> FEATURE:
<223> OTHER INFORMATION: O157:H7 highly conserved sequence

<400> SEQUENCE: 20
cctggtgggc agaaagaagc c                                              21

<210> SEQ ID NO 21
<211> LENGTH: 14
<212> TYPE: DNA
<213> ORGANISM: Artificial Sequence
<220> FEATURE:
<223> OTHER INFORMATION: Forward primer #1

<400> SEQUENCE: 21
aggagggcgc acta                                                      14

<210> SEQ ID NO 22
<211> LENGTH: 14
<212> TYPE: DNA
<213> ORGANISM: Artificial Sequence
<220> FEATURE:
<223> OTHER INFORMATION: Reverse primer #1

<400> SEQUENCE: 22
ggatcggcgc aact                                                      14

<210> SEQ ID NO 23
<211> LENGTH: 26
<212> TYPE: DNA
<213> ORGANISM: Artificial Sequence
<220> FEATURE:
<223> OTHER INFORMATION: Molecular Beacon #1 with stem

<400> SEQUENCE: 23
```

```
cctggtgggc agaaagaag ccaggg                                         26
```

<210> SEQ ID NO 24
<211> LENGTH: 21
<212> TYPE: DNA
<213> ORGANISM: Artificial Sequence
<220> FEATURE:
<223> OTHER INFORMATION: Molecular Beacon #1 loop sequence

<400> SEQUENCE: 24

```
cctggtgggc agaaagaagc c                                             21
```

<210> SEQ ID NO 25
<211> LENGTH: 26
<212> TYPE: DNA
<213> ORGANISM: Artificial Sequence
<220> FEATURE:
<223> OTHER INFORMATION: Reverse complement of Molecular
      Beacon sequence #1 with stem

<400> SEQUENCE: 25

```
ccctggcttc tttctgccca ccaggg                                        26
```

<210> SEQ ID NO 26
<211> LENGTH: 21
<212> TYPE: DNA
<213> ORGANISM: Artificial Sequence
<220> FEATURE:
<223> OTHER INFORMATION: Reverse complement of Molecular
      Beacon #1 loop sequence

<400> SEQUENCE: 26

```
ggcttctttc tgcccaccag g                                             21
```

<210> SEQ ID NO 27
<211> LENGTH: 19
<212> TYPE: DNA
<213> ORGANISM: Artificial Sequence
<220> FEATURE:
<223> OTHER INFORMATION: Forward primer #2

<400> SEQUENCE: 27

```
tggtgaggag ggcgcacta                                                19
```

<210> SEQ ID NO 28
<211> LENGTH: 21
<212> TYPE: DNA
<213> ORGANISM: Artificial Sequence
<220> FEATURE:
<223> OTHER INFORMATION: Reverse primer #2

<400> SEQUENCE: 28

```
gaataggctt cagcaatcag c                                             21
```

<210> SEQ ID NO 29
<211> LENGTH: 208
<212> TYPE: DNA
<213> ORGANISM: Escherichia coli
<220> FEATURE:
<223> OTHER INFORMATION: O157:H7 gnd conserved sequence #2

<400> SEQUENCE: 29

```
gcctcgtcgc atcttgttaa tggtgaaagc aggtgcaggc acggatgctg ctattgattc    60
ccttaagcca tacctcgata aaggtgacat catcattgat ggtggtaata ccttcttcca   120
ggacaccatt cgtcgtaacc gtgagctttc tgcagaaggc tttaacttca tcggtaccgg   180
```

```
tgtttccggt ggtgaggagg gcgcacta                                              208

<210> SEQ ID NO 30
<211> LENGTH: 28
<212> TYPE: DNA
<213> ORGANISM: Escherichia coli
<220> FEATURE:
<223> OTHER INFORMATION: O157:H7 highly conserved sequence

<400> SEQUENCE: 30
caggcacgga tgctgctatt gattccct                                              28

<210> SEQ ID NO 31
<211> LENGTH: 14
<212> TYPE: DNA
<213> ORGANISM: Artificial Sequence
<220> FEATURE:
<223> OTHER INFORMATION: Forward primer #3

<400> SEQUENCE: 31
gcctcgtcgc atct                                                             14

<210> SEQ ID NO 32
<211> LENGTH: 14
<212> TYPE: DNA
<213> ORGANISM: Artificial Sequence
<220> FEATURE:
<223> OTHER INFORMATION: Reverse primer #3

<400> SEQUENCE: 32
tagtgcgccc tcct                                                             14

<210> SEQ ID NO 33
<211> LENGTH: 33
<212> TYPE: DNA
<213> ORGANISM: Artificial Sequence
<220> FEATURE:
<223> OTHER INFORMATION: Molecular Beacon #2 sequence
      with stem

<400> SEQUENCE: 33
cccaggcacg gatgctgcta ttgattccct ggg                                        33

<210> SEQ ID NO 34
<211> LENGTH: 28
<212> TYPE: DNA
<213> ORGANISM: Artificial Sequence
<220> FEATURE:
<223> OTHER INFORMATION: Molecular Beacon #2 loop sequence

<400> SEQUENCE: 34
caggcacgga tgctgctatt gattccct                                              28

<210> SEQ ID NO 35
<211> LENGTH: 33
<212> TYPE: DNA
<213> ORGANISM: Artificial Sequence
<220> FEATURE:
<223> OTHER INFORMATION: Reverse complement of Molecular
      Beacon #2 sequence with stem

<400> SEQUENCE: 35
cccagggaat caatagcagc atccgtgcct ggg                                        33

<210> SEQ ID NO 36
<211> LENGTH: 28
<212> TYPE: DNA
```

```
<213> ORGANISM: Artificial Sequence
<220> FEATURE:
<223> OTHER INFORMATION: Reverse complement of Molecular Beacon #2 loop
      sequence

<400> SEQUENCE: 36
agggaatcaa tagcagcatc cgtgcctg                                          28

<210> SEQ ID NO 37
<211> LENGTH: 20
<212> TYPE: DNA
<213> ORGANISM: Artificial Sequence
<220> FEATURE:
<223> OTHER INFORMATION: Forward primer #4

<400> SEQUENCE: 37
ggaaacgcct cgtcgcatct                                                   20

<210> SEQ ID NO 38
<211> LENGTH: 19
<212> TYPE: DNA
<213> ORGANISM: Artificial Sequence
<220> FEATURE:
<223> OTHER INFORMATION: Reverse primer #4

<400> SEQUENCE: 38
tagtgcgccc tcctcacca                                                    19

<210> SEQ ID NO 39
<211> LENGTH: 29
<212> TYPE: DNA
<213> ORGANISM: Artificial Sequence
<220> FEATURE:
<223> OTHER INFORMATION: Molecular Beacon #3 sequence
      with stem

<400> SEQUENCE: 39
cgtccttaag ccatacctcg ataaggacg                                         29

<210> SEQ ID NO 40
<211> LENGTH: 21
<212> TYPE: DNA
<213> ORGANISM: Artificial Sequence
<220> FEATURE:
<223> OTHER INFORMATION: Molecular Beacon #3 loop sequence

<400> SEQUENCE: 40
ccttaagcca tacctcgata a                                                 21

<210> SEQ ID NO 41
<211> LENGTH: 29
<212> TYPE: DNA
<213> ORGANISM: Artficial Sequence
<220> FEATURE:
<223> OTHER INFORMATION: Reverse complement of Molecular
      Beacon #3 sequence with stem

<400> SEQUENCE: 41
cgtccttatc gaggtatggc ttaaggacg                                         29

<210> SEQ ID NO 42
<211> LENGTH: 21
<212> TYPE: DNA
<213> ORGANISM: Artificial Sequence
<220> FEATURE:
<223> OTHER INFORMATION: Reverse complement Molecular Beacon #3
      loop sequence
```

-continued

```
<400> SEQUENCE: 42
ttatcgaggt atggcttaag g                                              21

<210> SEQ ID NO 43
<211> LENGTH: 269
<212> TYPE: DNA
<213> ORGANISM: Escherichia coli
<220> FEATURE:
<223> OTHER INFORMATION: O157:H7 consensus sequence

<400> SEQUENCE: 43
gcctcgtcgc atcttgttaa tggtgaaagc aggtgcaggc acggatgctg ctattgattc      60
ccttaagcca tacctcgata aaggtgacat catcattgat ggtggtaata ccttcttcca     120
ggacaccatt cgtcgtaacc gtgagctttc tgcagaaggc tttaacttca tcggtaccgg     180
tgtttccggt ggtgaggagg gcgcactaaa aggtccttcc attatgcctg gtgggcagaa     240
agaagcctat gaactagttg cgccgatcc                                        269
```

US 8,088,572 B2

POLYNUCLEOTIDES FOR THE DETECTION OF *ESCHERICHIA COLI* O157:H7 AND *ESCHERICHIA COLI* O157:NM VEROTOXIN PRODUCERS

FIELD OF THE INVENTION

The present invention pertains to the field of detection of microbial contaminants and, in particular, the invention relates to the detection of contamination by *Escherichia coli* O157:H7 and/or *Escherichia coli* O157:NM which produce verotoxin.

BACKGROUND OF THE INVENTION

*Escherichia coli* O157:H7 (*E. coli* O157:H7) is one of hundreds of strains of the bacterium *Escherichia coli*. The combination of letters and numbers in the name of the bacterium refers to the specific markers found on its surface and distinguishes it from other types of *E. coli*. An estimated 73,000 cases of infection and 61 deaths occur in the United States each year. It accounts for about 2% of all cases of diarrhea in the western world, and at least one-third of all cases of hemorrhagic colitis. This bacterium is commonly associated with foods such as ground beef, unpasteurized milk and juice, sprouts, lettuce, salami, and game meat, and contact with cattle. Waterborne transmission occurs through swimming in contaminated lakes, pools, or drinking inadequately chlorinated water. The organism is easily transmitted from person to person and has been difficult to control in child day-care centers. *E. coli* O157:H7 produces large quantities of one or more related Shiga toxins that cause severe illness and damage in humans. The illness is characterized by severe cramping (abdominal pain) and diarrhea which is initially watery but becomes grossly bloody. Occasionally vomiting occurs. In severe cases, a complication called hemolytic uremic syndrome (HUS), in which the red blood cells are destroyed and the kidneys fail, may develop. (Doyle, P M et al. *Food Microbiology, Fundamentals and Frontiers*, ASM press, 1997, chapter 10, pp. 171 to 191).

*E. coli* O157 which are non-motile are designated *E. coli* O157:H- or O157:NM. *E. coli* O157:H- or O157:NM are missing the H antigen which is the flagellar or motility antigen. They usually produce verotoxin and cause a similar pattern of disease as *E. coli* O157:H7.

In order to prevent the occurrence of infections by *E. coli* O157:H7 and other toxin producing variants such as verotoxin producing *E. coli* O157:NM, methods of detection can be employed that identify the presence of the bacteria in food, prior to consumer availability and consumption. Many detection techniques, however, require long time periods and, therefore are not time and cost effective due to relatively quick rates of food spoilage. For example, a number of detection technologies require the culturing of bacterial samples for time periods of up to eight days. During that time, however, the product being tested must be placed in circulation for purchase and consumption. Therefore, a system that can rapidly identify the presence of *E. coli* O157:H7 and other toxin producing variants such as verotoxin producing *E. coli* O157:NM in food and other test samples is desirable.

A variety of methods are described in the prior art for the detection of bacterial contaminants. One of these methods is the amplification of specific nucleotide sequences using specific primers in a PCR assay. Upon completion of the amplification of a target sequence, the presence of an amplicon is detected using agarose gel electrophoresis. This method of detection, while being more rapid than traditional methods requiring culturing bacterial samples, is still relatively time consuming and subject to post-PCR contamination during the running of the agarose gel.

An additional technology utilized for detection of bacterial contamination, is nucleic acid hybridization. In such detection methodologies, the target sequence of interest is typically amplified and then hybridized to an oligonucleotide probe which possesses a complementary nucleic acid sequence to that of the target molecule. The probe can be modified so that detection of the hybridization product may occur, for example, the probe can be labelled with a radioisotope or fluorescent moiety.

The general use of *E. coli* nucleic acid sequences for the detection of this bacterium has been described. Many of the described detection methods are specific for certain strains of *E. coli*, such as O157. Others detect multiple strains of *E. coli*. For example, U.S. Pat. No. 5,654,417 describes DNA fragments useful for detecting *E. coli* strains and U.S. Pat. No. 6,365,723 describes genomic sequences, which can be used as diagnostic probes. These sequences are present in *E. coli* but absent from *E. coli* K 12. More general methods are provided in U.S. Pat. Nos. 5,693,469 and 6,551,776, which describe hybridization assay probes complementary to *E. coli* rRNA sequences. In addition to hybridizing to *E. coli* sequences, these probes hybridize to other genus members and *Shigella* species.

In addition, a number of PCR based methods of detecting *E. coli* have been described. For example, U.S. Pat. No. 6,268,143 describes a PCR-based 5' nuclease assay for presumptively detecting *E. coli* O157:H7 DNA. International application WO03/062464A3 describes a kit that has the potential for use directly on foods and environmental samples. The kit comprises three multiplex PCR assays that can detect in *E. coli* the presence of eight virulence genes: eaeA, EHEC-HlyA, Stx1 (VT1), Stx2 (VT2), Stx2c (VT2c), Stx2d (VT2d), Stx2e (VT2e) and Stx2f (VT2f). While, Desmarchelier et al. (*J. Clin. Microbiol.* (1998) 36:1801-1804) describe a PCR-based method for detecting *E. coli* 0157 that involves amplification of a region of the O-antigen synthesis genes followed by gel electrophoresis and Southern blot analysis to confirm the identify of the amplified fragment. The method was capable of identifying two serotypes of *E. coli* O157; the O157:H7 and 0157:H-serotypes. Another PCR-based protocol based on the amplification of the rfjB region of the O-antigen synthesis genes is described by Maurer et al. (*Appl. Environ. Microbiol.* (1999) 65:2954-2960).

A useful modification of the above technology provides for the concurrent amplification and detection of the target sequence (i.e. in "real time") through the use of specially adapted oligonucleotide probes. Examples of such probes include molecular beacon probes (Tyagi et al., (1996) *Nature Biotechnol.* 14:303-308), TaqMan® probes (U.S. Pat. Nos. 5,691,146 and 5,876,930) and Scorpion probes (Whitcombe et al., (1999) *Nature Biotechnol.* 17:804-807). The use of TaqMan® probes to detect *Escherichia coli* in water samples is described by Frahm and Obst in *J. Microbiol. Methods* (2003) 52:123-131. U.S. Pat. No. 6,664,080 discloses the detection of pathogenic *E. coli* strains using a Taqman (TM)-PCR based approach comprising the use of primers and fluorogenic probes specific for the genes encoding characteristic virulence factors or toxins.

Molecular beacons represent a powerful tool for the rapid detection of specific nucleotide sequences and are capable of detecting the presence of a complementary nucleotide sequence even in homogenous solutions. Molecular beacons can be described as hairpin stem-and-loop oligonucleotide sequences, in which the loop portion of the molecule represents a probe sequence, which is complementary to a predetermined sequence in a target nucleotide sequence. One arm of the beacon sequence is attached to a fluorescent moiety, while the other arm of the beacon is attached to a non-fluorescent quencher. The stem portion of the stem-and-loop sequence holds the two arms of the beacon in close proximity. Under these circumstances, the fluorescent moiety is quenched. When the beacon encounters a nucleic acid sequence complementary to its probe sequence, the probe hybridizes to the nucleic acid sequence, forming a stable complex and, as a result, the arms of the probe are separated and the fluorophore emits light. Thus, the emission of light is indicative of the presence of the specific nucleic acid sequence. Individual molecular beacons are highly specific for the nucleic acid sequences they are complementary to.

A molecular beacon probe designed to detect the *E. coli* O157:H7 serotype has been described (Fortin et al., (2001) *Analytical Biochem.* 289:281-288). The probe was designed to hybridise to an amplified target sequence from the rJbE O-antigen synthesis gene of *E. coli* O157:H7 that is either 496 base pair (bp) or 146 bp in length, depending on the primers used. The probe was also able to detect *E. coli* O157:NM and O157:H-serotypes, but was not intended to detect other strains of *E. coli*.

The gnd gene from several bacteria, including many *E. coli* strains and serotypes, *Shigella flexneri, Citrobacter freundii, Citrobacter koseri, Salmonella enterica* and *Salmonella typhimurium* has been characterized. The gnd gene codes for a decarboxylating gluconate-6-phosphate dehydrogenase (6-PGD) and is a part of the pentose phosphate pathway where it oxidises 6-Phosphogluconate into Ribulose-5-phosphate which is used for the synthesis of nucleic acids. In *E. coli* the gnd gene is locate in close proximity (200-2000 bp) to the rjb cluster that codes for the O antigen that is used for serotyping *Escherichia coli*. This advances the concept that new alleles of gnd, created either by point mutation or intragenic recombination, "hitchhike" to high frequency by diversifying selection favoring antigen variation at the adjacent rib locus. In addition, local recombination events involving the rjb region and extending though the gnd locus could result in specific combinations of gnd alleles and rjb genes being cotransferred in nature. The gnd allelle A that was targeted has been found only in *E. coli* 0157 from the DEC5 lineage [Tarr P I, Schoening L M et al., (2000) *Journal of Bacteriology* 182(21):6183-9191; Nelson K, Selander R K (1994) *Proc. Natl. Acad. Sci. USA.* 91:10227-10231].

International Patent Application WO/034484 and U.S. Patent Application 20020150902 disclose the gnd gene sequence of fourteen strains of *E. coli* (11 of which were *E. coli* O157:H7) and polymorphisms therein. These applications further disclose that these polymorphisms can be used to identify the presence of a particular strain of *E. coli* and/or differentiate one strain of *E. coli* from another, but do not provide a rational approach for the actual detection of specific strains and at the desired level of specificity.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide polynucleotides for the detection of *Escherichia coli* O157:H7 and *Escherichia coli* O157:NM verotoxin producers. In accordance with one aspect of the present invention, there is provided, a combination of polynucleotides for amplification and detection of nucleic acid sequences from *E. coli* O157:H7 and/or *E. coli* O157:NM which produces verotoxin, said combination selected from the group of:

(a) a combination comprising a first polynucleotide primer comprising at least 7 consecutive nucleotides of the sequence as set forth in SEQ ID NO:1; a second polynucleotide primer comprising at least consecutive 7 nucleotides of a sequence complementary to SEQ ID NOs:1 and a polynucleotide probe comprising at least 7 consecutive nucleotides of the sequence as set forth in SEQ ID NO:19, or the complement thereof;

(b) a combination comprising a first polynucleotide primer comprising at least 7 consecutive nucleotides of the sequence as set forth in SEQ ID NO:1; a second polynucleotide primer comprising at least 7 consecutive nucleotides of a sequence complementary to SEQ ID NO:1 and a polynucleotide probe comprising at least 7 consecutive nucleotides of the sequence as set forth in SEQ ID NO:29, or the complement thereof; and (c) a combination comprising a first polynucleotide primer comprising at least 7 consecutive nucleotides of the sequence as set forth in SEQ ID NO:1; a second polynucleotide primer comprising at least 7 consecutive nucleotides of a sequence complementary to SEQ ID NO:1 and a polynucleotide probe comprising at least 7 consecutive nucleotides of the sequence as set forth in SEQ ID NO:43, or the complement thereof.

In accordance with another aspect of the present invention, there is provided a method of detecting *E. coli* O157:H7 and/or *E. coli* O157:NM which produces verotoxin in a sample, said method comprising the steps of:

(i) contacting a sample suspected of containing, or known to contain, *E. coli* O157:H7 and/or *E. coli* O157:NM which produces verotoxin with a combination of polynucleotide primers capable of amplifying a *E. coli* target sequence within the gnd gene, under conditions that permit amplification of the target nucleotide sequence, said polynucleotide primers comprising:

(a) a first polynucleotide primer comprising at least 7 consecutive nucleotides of the sequence as set forth in SEQ ID NO:1

(b) a second polynucleotide primer comprising at least 7 consecutive nucleotides of a sequence complementary to SEQ ID NO:1; and (ii) detecting amplified target nucleotide sequence, wherein detection of amplified target nucleotide sequence indicates the presence of *E. coli* O157:H7 and/or *E. coli* O157:NM which produces verotoxin in the sample.

In accordance with another aspect of the present invention, there is provided a kit for the detection of *E. coli* O157:H7 and/or verotoxin producing *E. coli* O157:NM in a sample, said kit comprising a combination of polynucleotides selected from the group of:

(a) a combination comprising a first polynucleotide primer comprising at least 7 consecutive nucleotides of the sequence as set forth in SEQ ID NO:1; a second polynucleotide primer comprising at least 7 consecutive nucleotides of a sequence complementary to SEQ ID NO:1 and a polynucleotide probe comprising at least 7 consecutive nucleotides of the sequence as set forth in SEQ ID NO:19, or the complement thereof;

(b) a combination comprising a first polynucleotide primer comprising at least 7 consecutive nucleotides of the sequence as set forth in SEQ ID NO:1; a second polynucleotide primer comprising at least 7 consecutive nucleotides of a sequence complementary to SEQ ID NO:1 and a first polynucleotide probe comprising at least 7 consecutive nucleotides of the sequence as set forth in SEQ ID NO:29, or the complement thereof; and (c) a combination comprising a first polynucleotide primer comprising at least 7 consecutive nucleotides of the sequence as set forth in SEQ ID NO:1; a second polynucleotide primer comprising at least 7 consecutive nucleotides of a sequence complementary to SEQ ID NO:1 and a polynucleotide probe comprising at least 7 consecutive nucleotides of the sequence as set forth in SEQ ID NO:43, or the complement thereof.

In accordance with another aspect of the present invention, there is provided a pair of polynucleotide primers for amplification of a portion of a gnd gene from *E. coli* O157:H7 and/or *E. coli* O157:NM which produces verotoxin, said portion being less than about 500 nucleotides in length and comprising at least 50 consecutive nucleotides of the sequence set forth in SEQ ID NO:19, said pair of polynucleotide primers comprising:

(a) a first polynucleotide primer comprising at least 7 consecutive nucleotides of the sequence as set forth in SEQ ID NO:1; and (b) a second polynucleotide primer comprising at least 7 consecutive nucleotides of a sequence complementary to SEQ ID NO:1.

In accordance with another aspect of the present invention, there is provided a pair of polynucleotide primers for amplification of a portion of a gnd gene *E. coli* O157:H7 and/or *E. coli* O157:NM which produces verotoxin, said portion being less than about 500 nucleotides in length and comprising at least 160 consecutive nucleotides of the sequence set forth in SEQ ID NO:29, said pair of polynucleotide primers comprising:

(a) a first polynucleotide primer comprising at least 7 consecutive nucleotides of the sequence as set forth in SEQ ID NO:1; and (b) a second polynucleotide primer comprising at least 7 consecutive nucleotides of a sequence complementary to SEQ ID NO:1.

In accordance with another aspect of the present invention, there is provided a pair of polynucleotide primers for amplification of a portion of a gnd gene *E. coli* O157:H7 and/or *E. coli* O157:NM which produces verotoxin, said portion being less than about 500 nucleotides in length and comprising at least 50 consecutive nucleotides of the sequence set forth in SEQ ID NO:43, said pair of polynucleotide primers comprising:

(a) a first polynucleotide primer comprising at least 7 consecutive nucleotides of the sequence as set forth in SEQ ID NO:1; and (b) a second polynucleotide primer comprising at least 7 consecutive nucleotides of a sequence complementary to SEQ ID NO:1.

In accordance with another aspect of the present invention, there is provided an isolated polynucleotide consisting essentially of:

(a) the sequence as set forth in any one of SEQ ID NOs: 19, 29 or 43, or a fragment of said sequence; or (b) a sequence that is the complement of (a).

In accordance with another aspect of the present invention, there is provided a primer comprising at least 7 consecutive nucleotides of a sequence as set forth in SEQ ID NO: 2-11 or the complement thereof.

In accordance with another aspect of the present invention, there is provided an isolated polynucleotide having a sequence as set forth in any one of SEQ ID NOs: 19, 20, 23, 24, 25, 26, 29, 30, 33, 34, 35, 36 39, 40, 41, 42, or 43, or the complement thereof.

In accordance with another aspect of the present invention, there is provide a polynucleotide probe comprising at least 7 consecutive nucleotides of a sequence as set forth in any one of SEQ ID NO: 19, 20, 23, 24, 25, 26, 29, 30, 33, 34, 35, 36 39, 40, 41, 42, or 43, or the complement thereof.

In accordance with another aspect of the present invention, there is provide a combination of polynucleotides for amplification and detection of nucleic acid sequences from *E. coli* O157:H7, said combination selected from the group of:

(a) a combination comprising a first polynucleotide primer comprising at least 7 consecutive nucleotides of the sequence as set forth in SEQ ID NO:1; a second polynucleotide primer comprising at least consecutive 7 nucleotides of a sequence complementary to SEQ ID NOs:1 and a polynucleotide probe comprising at least 7 consecutive nucleotides of the sequence as set forth in SEQ ID NO:19, or the complement thereof;

(b) a combination comprising a first polynucleotide primer comprising at least 7 consecutive nucleotides of the sequence as set forth in SEQ ID NO:1; a second polynucleotide primer comprising at least 7 consecutive nucleotides of a sequence complementary to SEQ ID NO:1 and a polynucleotide probe comprising at least 7 consecutive nucleotides of the sequence as set forth in SEQ ID NO:29, or the complement thereof; and (c) a combination comprising a first polynucleotide primer comprising at least 7 consecutive nucleotides of the sequence as set forth in SEQ ID NO:1; a second polynucleotide primer comprising at least 7 consecutive nucleotides of a sequence complementary to SEQ ID NO:1 and a polynucleotide probe comprising at least 7 consecutive nucleotides of the sequence as set forth in SEQ ID NO:43, or the complement thereof.

In accordance with another aspect of the present invention, there is provided a combination of polynucleotides for amplification and detection of nucleic acid sequences from *E. coli* O157:NM which produces verotoxin, said combination selected from the group of:

(a) a combination comprising a first polynucleotide primer comprising at least 7 consecutive nucleotides of the sequence as set forth in SEQ ID NO:1; a second polynucleotide primer comprising at least consecutive 7 nucleotides of a sequence complementary to SEQ ID NOs:1 and a polynucleotide probe comprising at least 7 consecutive nucleotides of the sequence as set forth in SEQ ID NO:19, or the complement thereof;

(b) a combination comprising a first polynucleotide primer comprising at least 7 consecutive nucleotides of the sequence as set forth in SEQ ID NO:1; a second polynucleotide primer comprising at least 7 consecutive nucleotides of a sequence complementary to SEQ ID NO:1 and a polynucleotide probe comprising at least 7 consecutive nucleotides of the sequence as set forth in SEQ ID NO:29, or the complement thereof; and (c) a combination comprising a first polynucleotide primer comprising at least 7 consecutive nucleotides of the sequence as set forth in SEQ ID NO:1; a second polynucleotide primer comprising at least 7 consecutive nucleotides of a sequence complementary to SEQ ID NO:1 and a polynucleotide probe comprising at least 7 consecutive nucleotides of the sequence as set forth in SEQ ID NO:43, or the complement thereof.

In accordance with another aspect of the present invention, there is provide a method of detecting *E. coli* O157:H7 in a sample, said method comprising the steps of:
(i) contacting a sample suspected of containing, or known to contain, *E. coli* O157:H7 with a combination of polynucleotide primers capable of amplifying a *E. coli* target sequence within the gnd gene, under conditions that permit amplification of the target nucleotide sequence, said polynucleotide primers comprising:
   (a) a first polynucleotide primer comprising at least 7 consecutive nucleotides of the sequence as set forth in SEQ ID NO:1
   (b) a second polynucleotide primer comprising at least 7 consecutive nucleotides of a sequence complementary to SEQ ID NO:1; and
(ii) detecting amplified target nucleotide sequence,
wherein detection of amplified target nucleotide sequence indicates the presence of *E. coli* O157:H7 in the sample.

In accordance with another aspect of the present invention, there is provided a method of detecting *E. coli* O157:NM which produces verotoxin in a sample, said method comprising the steps of:
(i) contacting a sample suspected of containing, or known to contain verotoxin producing *E. coli* O157:NM with a combination of polynucleotide primers capable of amplifying a *E. coli* target sequence within the gnd gene, under conditions that permit amplification of the target nucleotide sequence, said polynucleotide primers comprising:
   (a) a first polynucleotide primer comprising at least 7 consecutive nucleotides of the sequence as set forth in SEQ ID NO:1
   (b) a second polynucleotide primer comprising at least 7 consecutive nucleotides of a sequence complementary to SEQ ID NO:1; and
(ii) detecting amplified target nucleotide sequence,
wherein detection of amplified target nucleotide sequence indicates the presence of *E. coli* O157:NM which produces verotoxin in the sample.

In accordance with another aspect of the present invention, there is provided a kit for the detection of *E. coli* O157:H7 in a sample, said kit comprising a combination of polynucleotides selected from the group of:
(a) a combination comprising a first polynucleotide primer comprising at least 7 consecutive nucleotides of the sequence as set forth in SEQ ID NO:1; a second polynucleotide primer comprising at least 7 consecutive nucleotides of a sequence complementary to SEQ ID NO:1 and a polynucleotide probe comprising at least 7 consecutive nucleotides of the sequence as set forth in SEQ ID NO:19, or the complement thereof;
(b) a combination comprising a first polynucleotide primer comprising at least 7 consecutive nucleotides of the sequence as set forth in SEQ ID NO:1; a second polynucleotide primer comprising at least 7 consecutive nucleotides of a sequence complementary to SEQ ID NO:1 and a first polynucleotide probe comprising at least 7 consecutive nucleotides of the sequence as set forth in SEQ ID NO:29, or the complement thereof; and
(c) a combination comprising a first polynucleotide primer comprising at least 7 consecutive nucleotides of the sequence as set forth in SEQ ID NO:1; a second polynucleotide primer comprising at least 7 consecutive nucleotides of a sequence complementary to SEQ ID NO:1 and a polynucleotide probe comprising at least 7 consecutive nucleotides of the sequence as set forth in SEQ ID NO:43, or the complement thereof.

In accordance with another aspect of the present invention, there is provided a kit for the detection of *E. coli* O157:NM which produces verotoxin in a sample, said kit comprising a combination of polynucleotides selected from the group of:
(a) a combination comprising a first polynucleotide primer comprising at least 7 consecutive nucleotides of the sequence as set forth in SEQ ID NO:1; a second polynucleotide primer comprising at least 7 consecutive nucleotides of a sequence complementary to SEQ ID NO:1 and a polynucleotide probe comprising at least 7 consecutive nucleotides of the sequence as set forth in SEQ ID NO:19, or the complement thereof;
(b) a combination comprising a first polynucleotide primer comprising at least 7 consecutive nucleotides of the sequence as set forth in SEQ ID NO:1; a second polynucleotide primer comprising at least 7 consecutive nucleotides of a sequence complementary to SEQ ID NO:1 and a first polynucleotide probe comprising at least 7 consecutive nucleotides of the sequence as set forth in SEQ ID NO:29, or the complement thereof; and
(c) a combination comprising a first polynucleotide primer comprising at least 7 consecutive nucleotides of the sequence as set forth in SEQ ID NO:1; a second polynucleotide primer comprising at least 7 consecutive nucleotides of a sequence complementary to SEQ ID NO:1 and a polynucleotide probe comprising at least 7 consecutive nucleotides of the sequence as set forth in SEQ ID NO:43, or the complement thereof.

In accordance with another aspect of the present invention, there is provided a pair of polynucleotide primers for amplification of a portion of a gnd gene from *E. coli* O157:H7, said portion being less than about 500 nucleotides in length and comprising at least 50 consecutive nucleotides of the sequence set forth in SEQ ID NO:19, said pair of polynucleotide primers comprising:
(a) a first polynucleotide primer comprising at least 7 consecutive nucleotides of the sequence as set forth in SEQ ID NO:1; and
(b) a second polynucleotide primer comprising at least 7 consecutive nucleotides of a sequence complementary to SEQ ID NO:1.

In accordance with another aspect of the present invention, there is provided a pair of polynucleotide primers for amplification of a portion of a gnd gene from *E. coli* O157:NM which produces verotoxin, said portion being less than about 500 nucleotides in length and comprising at least 50 consecutive nucleotides of the sequence set forth in SEQ ID NO:19, said pair of polynucleotide primers comprising:
(a) a first polynucleotide primer comprising at least 7 consecutive nucleotides of the sequence as set forth in SEQ ID NO:1; and
(b) a second polynucleotide primer comprising at least 7 consecutive nucleotides of a sequence complementary to SEQ ID NO:1.

In accordance with another aspect of the present invention, there is provided a pair of polynucleotide primers for amplification of a portion of a gnd gene from *E. coli* O157:H7, said portion being less than about 500 nucleotides in length and comprising at least 160 consecutive nucleotides of the sequence set forth in SEQ ID NO:29, said pair of polynucleotide primers comprising:
(a) a first polynucleotide primer comprising at least 7 consecutive nucleotides of the sequence as set forth in SEQ ID NO:1; and
(b) a second polynucleotide primer comprising at least 7 consecutive nucleotides of a sequence complementary to SEQ ID NO:1.

In accordance with another aspect of the present invention, there is provided a pair of polynucleotide primers for amplification of a portion of a gnd gene from E. coli O157:NM which produces verotoxin, said portion being less than about 500 nucleotides in length and comprising at least 160 consecutive nucleotides of the sequence set forth in SEQ ID NO:29, said pair of polynucleotide primers comprising:

(a) a first polynucleotide primer comprising at least 7 consecutive nucleotides of the sequence as set forth in SEQ ID NO:1; and
(b) a second polynucleotide primer comprising at least 7 consecutive nucleotides of a sequence complementary to SEQ ID NO:1.

In accordance with another aspect of the present invention, there is provided a pair of polynucleotide primers for amplification of a portion of a gnd gene from E. coli 01577:H7, said portion being less than about 500 nucleotides in length and comprising at least 50 consecutive nucleotides of the sequence set forth in SEQ ID NO:43, said pair of polynucleotide primers comprising:

(a) a first polynucleotide primer comprising at least 7 consecutive nucleotides of the sequence as set forth in SEQ ID NO:1; and
(b) a second polynucleotide primer comprising at least 7 consecutive nucleotides of a sequence complementary to SEQ ID NO:1.

In accordance with another aspect of the present invention, there is provided a pair of polynucleotide primers for amplification of a portion of a gnd gene from E. coli O157:NM which produces verotoxin, said portion being less than about 500 nucleotides in length and comprising at least 50 consecutive nucleotides of the sequence set forth in SEQ ID NO:43, said pair of polynucleotide primers comprising:

(a) a first polynucleotide primer comprising at least 7 consecutive nucleotides of the sequence as set forth in SEQ ID NO:1; and
(b) a second polynucleotide primer comprising at least 7 consecutive nucleotides of a sequence complementary to SEQ ID NO:1.

BRIEF DESCRIPTION OF THE DRAWINGS

These and other features of the invention will become more apparent in the following detailed description in which reference is made to the appended drawings wherein:

Figure 1:
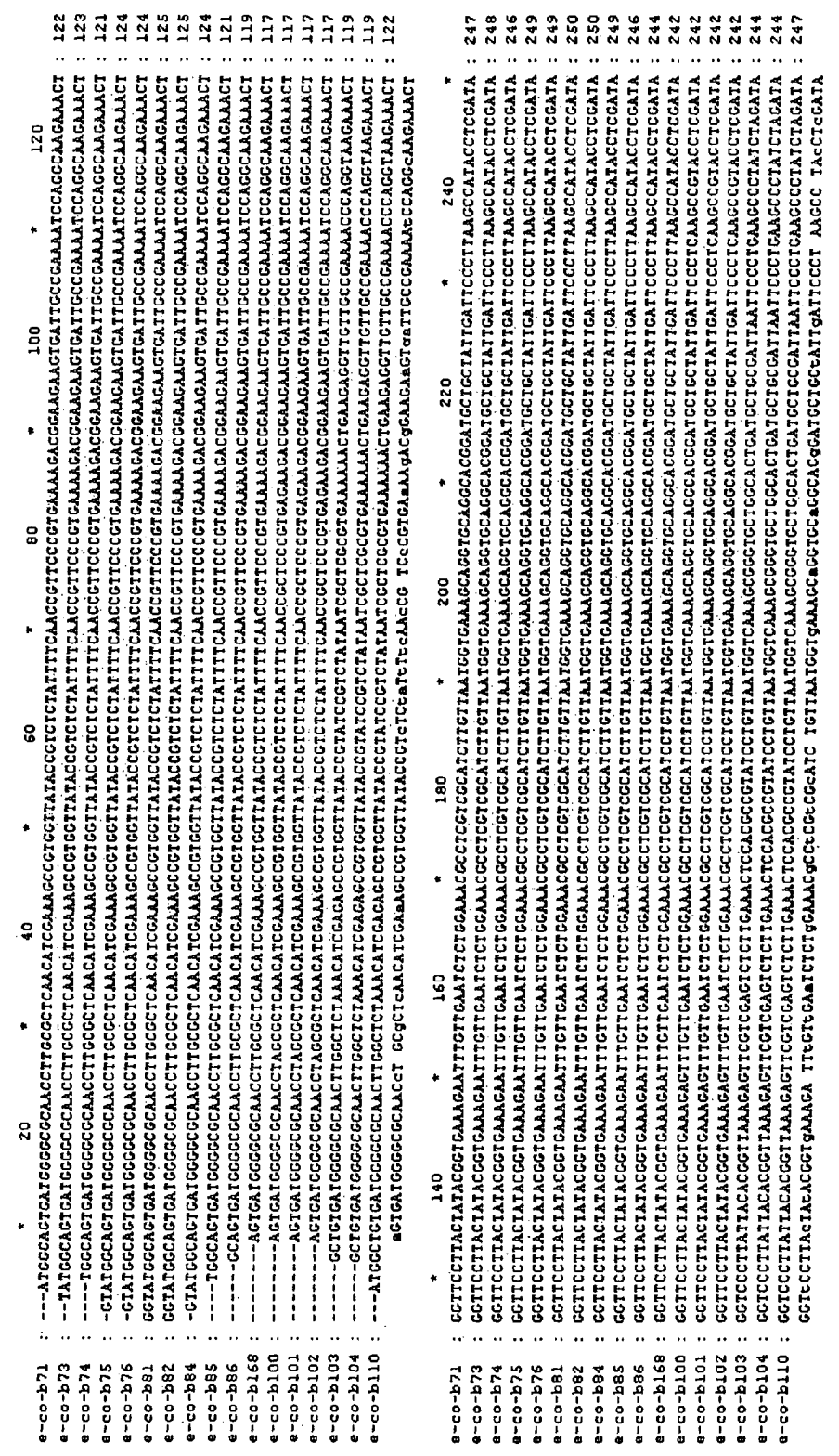
Figure 1:
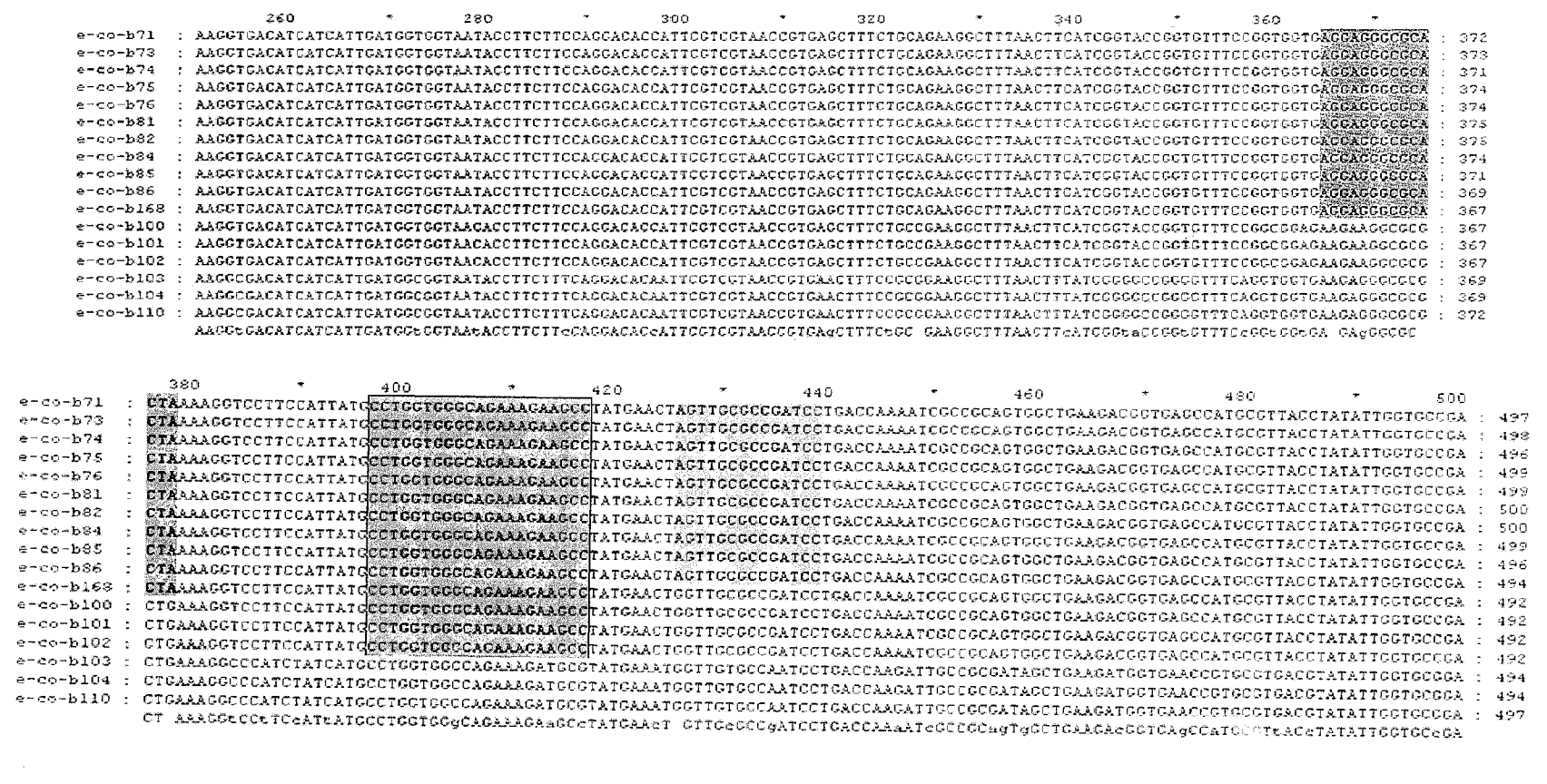

FIG. 1 presents a multiple sequence alignment showing conserved regions of a portion of the gnd gene from E. coli O157:H7 strains [SEQ ID NOs:2-11] and from various E. coli strains not O157:H7 [SEQ ID NOs:12-18] The sequences depicted represent the coding strand of the gene. Shaded blocks highlight the following regions: bases 365 to 378: forward primer #1 [SEQ ID NO:21]; bases 397 to 417: binding site for molecular beacon #1 [SEQ ID NO:24]; bases 426 to 439: reverse primer # 1 [SEQ ID NO:22];

FIG. 7 presents the sequence of (A) a E. coli O157:H7 gnd gene [SEQ ID NO: 1]; (B) a conserved region (conserved sequence #1) of the E. coli O157:H7 gnd gene, which is unique to E. coli O157:H7 isolates [SEQ ID NO:19], and (C) a 21 nucleotide sequence found within conserved sequence #1, which is exclusive to E. coli O157:H7 isolates [SEQ ID NO:20].

FIG. 8 presents the sequence of (A) a E. coli O157:H7 gnd gene [SEQ ID NO:1]; (B) a conserved region (conserved sequence #2) of the E. coli O157:H7 gnd gene, which is unique to E. coli O157:H7 isolates [SEQ ID NO:29], and (C) a 28 nucleotide sequence found within conserved sequence #2, which is exclusive to E. coli O157:H7 isolates [SEQ ID NO:30].

FIG. 9 presents the sequence of (A) a E. coli O157:H7 gnd gene [SEQ ID NO:1]; (B) a consensus sequence of the E. coli O157:H7 gnd gene, [SEQ ID NO:43.

DETAILED DESCRIPTION OF THE INVENTION

Figure 2:
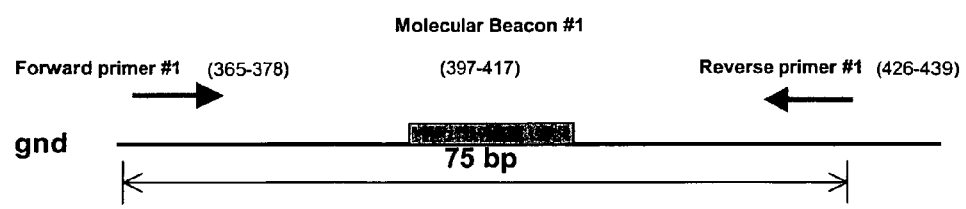
FIG. 2 presents the arrangement of PCR primers and a molecular beacon probe on a gnd conserved sequence # 1 (section 366-449 of the FIG. 1 alignment) in one embodiment of the invention. Numbers in parentheses indicate the positions of the first and last nucleotides of each feature on the PCR product generated with primers SEQ ID NOs:21 & 22.

The present invention is based on the identification of a highly conserved region (consensus sequence) within the E. coli O157:H7 genome that is common to known isolates of E. coli O157:H7 and is also present in verotoxin producing isolates of E. coli O157:NM, but absent from other bacteria including other E. coli serotypes and other species. The consensus sequence and conserved sequences therein constitute suitable target sequences for the design of primers and probes capable of specifically amplifying and detecting nucleic acids sequences from one or more E. coli O157:H7 isolates and/or verotoxin producing isolates of E. coli O157:NM in a test sample.

The present invention thus provides for primer and probe sequences capable of amplifying and/or detecting all or part of an E. coli O157:H7 consensus sequence that are suitable for use in detecting the presence of various E. coli O157:H7 isolates and/or verotoxin producing isolates of E. coli O157:NM in a sample, such as a clinical sample, microbiological culture, or a sample related to food, environmental or pharmaceutical quality control processes. The present invention contemplates methods of detecting E. coli O157:H7 isolates and/or verotoxin producing isolates of E. coli O157:NM in a sample using primers and/or probes targeting a consensus sequence, as well as methods using primers and/or probes that target one or more conserved regions within the consensus sequence. In one embodiment, the invention provides diagnostic assays that can be carried out in real time and addresses the need for rapid detection of E. coli O157:H7 and/or E. coli O157:NM which produce verotoxin in a variety of biological samples.

In one embodiment, the primers and probes sequences provided by the present invention are capable of distinguishing E. coli O157:H7 target sequences distinguishable from other *E. coli* sequences, i.e. specifically amplify and/or detect *E. coli* O157:H7 sequences but not *E. coli* sequences that are not O157:H7. In another embodiment, the primers and probe sequences are capable of distinguishing target sequences distinguishable from *E. coli* O157:H7 and verotoxin producing isolates of *E. coli* O157:NM from other *E. coli* sequences, i.e. specifically amplify and/or detect *E. coli* O157:H7 and verotoxin producing isolates of *E. coli* O157:NM sequences but not other *E. coli* sequences. In a further embodiment, the primers and probe sequences are capable of distinguishing target sequences distinguishable from verotoxin producing isolates of *E. coli* O157:NM from other *E. coli* sequences, i.e. specifically amplify and/or detect verotoxin producing isolates of *E. coli* O157:NM sequences but not other *E. coli* sequences.

In addition, the primers and probes of the invention demonstrate a specificity for *E. coli* O157:H7 and/or verotoxin producing isolates of *E. coli* O157:NM nucleic acid sequences of at least 90%, as defined herein. In one embodiment, the primers and probes of the invention demonstrate a specificity for *E. coli* O157:H7 and/or verotoxin producing isolates of *E. coli* O157:NM nucleic acid sequences of at least 95%. In another embodiment, the primers and probes of the invention demonstrate a specificity for *E. coli* O157:H7 and/or verotoxin producing isolates of *E. coli* O157:NM nucleic acid sequences of at least 97%. In further embodiments, the primers and probes demonstrate a specificity for *E. coli* O157:H7 and/or verotoxin producing isolates of *E. coli* O157:NM nucleic acid sequences of at least 98%, at least 99% and at least 99.5%.

In another embodiment, the primers and probes of the invention demonstrate a specificity for *E. coli* O157:H7 nucleic acid sequences of at least 90%, as defined herein. In a further embodiment, the primers and probes of the invention demonstrate a specificity for *E. coli* O157:H7 nucleic acid sequences of at least 95%. In yet a further embodiment, the primers and probes of the invention demonstrate a specificity for *E. coli* O157:H7 nucleic acid sequences of at least 97%. In still further embodiments, the primers and probes demonstrate a specificity for *E. coli* O157:H7 nucleic acid sequences of at least 98%, at least 99% and at least 99.5%.

In accordance with the present invention, the primers and probes demonstrate a sensitivity in detecting isolates of *E. coli* O157:H7 and/or verotoxin producing isolates of *E. coli* O157:NM of at least 90%. In another embodiment, the primers and probes demonstrate a sensitivity of at least 91%. In a further embodiment, the primers and probes demonstrate a sensitivity of at least 92%. In a further embodiment of the invention, the primers and probes demonstrate a sensitivity of at least 95%. In another embodiment, the primers and probes of the invention demonstrate a sensitivity for in detecting isolates of *E. coli* O157:H7 and/or verotoxin producing isolates of *E. coli* O157:NM of at least 97%. In another embodiment, the primers and probes of the invention demonstrate a sensitivity for isolates of *E. coli* O157:H7 and/or verotoxin producing isolates of *E. coli* O157:NM of at least 98%. In further embodiments, the primers and probes of the invention demonstrate a sensitivity for isolates of *E. coli* O157:H7 and/or verotoxin producing isolates of *E. coli* O157:NM of at least 99%, and at least 99.5%.

In accordance with another embodiment of the present invention, the primers and probes demonstrate a sensitivity in detecting *E. coli* O157:H7 isolates of at least 90%. In a further embodiment, the primers and probes demonstrate a sensitivity of at least 91%. In yet a further embodiment, the primers and probes demonstrate a sensitivity of at least 92%. In a still further embodiment of the invention, the primers and probes demonstrate a sensitivity of at least 95%. In another embodiment, the primers and probes of the invention demonstrate a sensitivity for *E. coli* O157:H7 isolates of at least 97%. In a further embodiment, the primers and probes of the invention demonstrate a sensitivity for *E. coli* O157:H7 isolates of at least 98%. In still further embodiments, the primers and probes of the invention demonstrate a sensitivity for *E. coli* O157:H7 isolates of at least 99%, and at least 99.5%.

In contrast to primers and probes described previously, which are often specific for a certain strain of *E. coli* O157:H7, the sensitivity of the primers and probes of the invention make them suitable for detecting a wide variety of *E. coli* O157:H7 strains and/or *E. coli* O157:NM which produce verotoxin, and are thus broadly applicable.

Definitions

Unless defined otherwise, all technical and scientific terms used herein have the same meaning as commonly understood by one of ordinary skill in the art to which this invention belongs.

The terms "oligonucleotide" and "polynucleotide" as used interchangeably in the present application refer to a polymer of greater than one nucleotide in length of ribonucleic acid (RNA), deoxyribonucleic acid (DNA), hybrid RNA/DNA, modified RNA or DNA, or RNA or DNA mimetics. The polynucleotides may be single- or double-stranded. The terms include polynucleotides composed of naturally-occurring nucleobases, sugars and covalent internucleoside (backbone) linkages as well as polynucleotides having non-naturally-occurring portions which function similarly. Such modified or substituted polynucleotides are well-known in the art and for the purposes of the present invention, are referred to as "analogues."

The terms "primer" and "polynucleotide primer," as used herein, refer to a short, single-stranded polynucleotide capable of hybridizing to a complementary sequence in a nucleic acid sample. A primer serves as an initiation point for template-dependent nucleic acid synthesis. Nucleotides are added to a primer by a nucleic acid polymerase in accordance with the sequence of the template nucleic acid strand. A "primer pair" or "primer set" refers to a set of primers including a 5' upstream primer that hybridizes with the 5' end of the sequence to be amplified and a 3' downstream primer that hybridizes with the complementary 3' end of the sequence to be amplified. The term "forward primer" as used herein, refers to a primer which anneals to the 5' end of the sequence to be amplified. The term "reverse primer", as used herein, refers to a primer which anneals to the complementary 3' end of the sequence to be amplified.

The terms "probe" and "polynucleotide probe," as used herein, refer to a polynucleotide used for detecting the presence of a specific nucleotide sequence in a sample. Probes specifically hybridize to a target nucleotide sequence, or the complementary sequence thereof, and can be single- or double-stranded.

The term "specifically hybridize," as used herein, refers to the ability of a polynucleotide to bind detectably and specifically to a target nucleotide sequence. Polynucleotides specifically hybridize to target nucleotide sequences under hybridization and wash conditions that minimize appreciable amounts of detectable binding to non-specific nucleic acids. High stringency conditions can be used to achieve specific hybridization conditions as is known in the art. Typically, hybridization and washing are performed at high stringency according to conventional hybridization procedures and employing one or more washing step in a solution comprising 1-3×SSC, 0.1-1% SDS at 50-70° C. for 5-30 minutes.

The term "specificity," as used herein, refers to the ability of a primer or primer pair to amplify, or a probe to detect, nucleic acid sequences from specific target bacterial species or serotypes but not other bacterial species or serotypes. "% specificity" is defined by a negative validation test wherein the primers and/or probe are tested against a panel of at least 100 bacterial species or serotypes other than the target species or serotype. Thus, for example, a pair of primers that does not amplify any nucleic acid sequences from a panel of bacterial species and/or serotypes other than E. coli O157:H7 would be defined as demonstrating 100% specificity and a pair of primers that amplified a nucleic acid sequence from one bacterial species in a panel of 100 species and/or serotypes other than E. coli O157:H7 would be defined as demonstrating 99% specificity to E. coli O157:H7. Specificity may relate to more than one target species or serotype. For example, a pair of primers that does not amplify any nucleic acid sequences from a panel of bacterial species or serotypes other than isolates of E. coli O157:H7 and verotoxin producing isolates of E. coli O157:NM would be defined as demonstrating 100% specificity to E. coli O157:H7 and verotoxin producing isolates of E. coli O157:NM and a pair of primers that amplified a nucleic acid sequence from one bacterial species in a panel of 100 species and/or serotypes other than E. coli O157:H7 and verotoxin producing isolates of E. coli O157:NM would be defined as demonstrating 99% specificity to E. coli O157: H7 and verotoxin producing isolates of E. coli O157:NM. Similarly, a probe that does not detect any nucleic acid sequences from a panel of bacterial species and/or serotypes other than E. coli O157:H7 would be defined as demonstrating 100% specificity to E. coli O157:H7 and a probe that detects a nucleic acid sequence from one bacterial species and/or serotype in a panel of 100 species other than E. coli O157:H7 would be defined as demonstrating 99% specificity to E. coli O157:H7. Similarly, a probe that does not detect any nucleic acid sequences from a panel of bacterial species or serotypes other than isolates of E. coli O157:H7 and verotoxin producing isolates of E. coli O157:NM would be defined as demonstrating 100% specificity to E. coli O157:H7 and verotoxin producing isolates of E. coli O157:NM and a probe that detects a nucleic acid sequence from one bacterial species in a panel of 100 species and/or serotypes other than E. coli O157:H7 and verotoxin producing isolates of E. coli O157:NM would be defined as demonstrating 99% specificity to E. coli O157:H7 and verotoxin producing isolates of E. coli O157:NM.

The term "sensitivity," as used herein, refers to the ability of a primer or primer pair to amplify, or a probe to detect, nucleic acid sequences from a range of isolates from a target bacterial species or serotype "% sensitivity" is defined by a positive validation test wherein the primers and/or probe are tested against a panel of at least 50 isolates of a target serotype. Thus, for example, a pair of primers that amplifies nucleic acid sequences from all E. coli O157:H7 isolates in the panel would be defined as demonstrating 100% sensitivity to E. coli O157:H7 and a pair of primers that amplified nucleic acid-sequences from 45 E. coli O157:H7 isolates in a panel of 50 isolates would be defined as demonstrating 90% sensitivity to E. coli O157:H7. Similarly, a probe that detects nucleic acid sequences from all E. coli O157:H7 isolates in the panel would be defined as demonstrating 100% sensitivity to E. coli O157:H7 and a probe that detects nucleic acid sequences from 45 E. coli O157:H7 isolates in a panel of 50 isolates would be defined as demonstrating 90% sensitivity to E. coli O157:H7. Sensitivity may relate to more than one target bacterial species or serotype. For example, a pair of primers that amplifies nucleic acid sequences from all isolates of E. coli O157:H7 and verotoxin producing isolates of E. coli O157:NM in the panel would be defined as demonstrating 100% sensitivity to E. coli O157:H7 and verotoxin producing isolates of E. coli O157:NM and a pair of primers that amplified nucleic acid sequences from 45 E. coli O157:H7 isolates and verotoxin producing isolates of E. coli O157:NM in a panel of 50 isolates would be defined as demonstrating 90% sensitivity to E. coli O157:H7 and verotoxin producing isolates of E. coli O157:NM. Similarly, a probe that detects nucleic acid sequences from all E. coli O157:H7 isolates and verotoxin producing isolates of E. coli O157:NM in the panel would be defined as demonstrating 100% sensitivity to E. coli O157:H7 and verotoxin producing isolates of E. coli O157: NM and a probe that detects nucleic acid sequences from 45 E. coli O157:H7 isolates and verotoxin producing isolates of E. coli O157:NM in a panel of 50 isolates would be defined as demonstrating 90% sensitivity to E. coli O157:H7 and verotoxin producing isolates of E. coli O157:NM.

The term "corresponding to" refers to a polynucleotide sequence that is identical to all or a portion of a reference polynucleotide sequence. In contradistinction, the term "complementary to" is used herein to indicate that a polynucleotide sequence is identical to all or a portion of the complementary strand of a reference polynucleotide sequence. For illustration, the nucleotide sequence "TATAC" corresponds to a reference sequence "TATAC" and is complementary to a reference sequence "GTATA".

The terms "hairpin" or "hairpin loop" refer to a single strand of DNA or RNA, the ends of which comprise complementary sequences, whereby the ends anneal together to form a "stem" and the region between the ends is not annealed and forms a "loop". Some probes, such as molecular beacons, have such "hairpin" structure when not hybridized to a target sequence. The loop is a single-stranded structure containing sequences complementary to the target sequence, whereas the stem self-hybridises to form a double-stranded region and is typically unrelated to the target sequence, however, nucleotides that are both complementary to the target sequence and that can self-hybridise can also be included in the stem region.

The terms "target sequence", "target nucleotide sequence," or "target nucleic acid sequence" as used herein, refer to a particular nucleic acid and/or its sequence in a test sample to which a primer and/or probe is intended to specifically hybridize. A "target sequence" is typically longer than the primer or probe sequence and thus can contain multiple "primer target sequences" and "probe target sequences". A target sequence may be single- or double-stranded. The term "primer target sequence" as used herein refers to a nucleic acid sequence that may or may not be in a test sample and to which a primer is designed to specifically hybridize. The term "probe target sequence" refers to a nucleic acid sequence that may or may not be in a test sample and to which a probe is designed to specifically hybridize.

As used herein, the term "about" refers to a +/−10% variation from the nominal value. It is to be understood that such a variation is always included in any given value provided herein, whether or not it is specifically referred to.

Target Sequences

A single nucleotide region of the gnd gene sequence, having a sequence corresponding to SEQ ID NO:43 was identified as being generally conserved in various isolates of E. coli O157:H7 and, therefore, a potential target sequence for probes. This sequence is identified or referred to herein as a consensus sequence. This sequence has also been identified in verotoxin producing isolates of E. coli O157:NM.

Multiple sequence alignment analysis of a portion of E. coli O157:H7 gnd gene sequences identified a 75 nucleotide region within the consensus sequence, having a sequence corresponding to SEQ ID NO:19 (shown in FIG. 7), as being generally conserved in the various isolates of *E. coli* O157:H7 and, therefore a potential target sequence for probes. This sequence is referred to herein as the gnd conserved sequence #1. This sequence has also been identified in verotoxin producing isolates of *E. coli* O157:NM. An exemplary multiple sequence alignment of portions of the coding strand of the gnd gene is shown in FIG. 1. One skilled in the art will appreciate that similar alignments can be conducted using longer sequences and/or the non coding strand of the gene, such as the region shown in FIG. 7A [SEQ ID NO:1].

Similarly, multiple sequence alignment analysis of a portion of *E. coli* O157:H7 gnd gene sequences identified a 208 nucleotide region within the consensus sequence, having a sequence corresponding to SEQ ID NO:29 (shown in FIG. 8), as being generally conserved in the various isolates of *E. coli* O157:H7 and, therefore a target sequence for probes. This sequence is referred to herein as conserved sequence #2. This sequence has also been identified in verotoxin producing isolates of *E. coli* O157:NM.

One skilled in the art will appreciate that similar alignments can be conducted to identify other conserved sequences using the coding and/or the non coding strands of the gene.

Accordingly in one embodiment, the present invention provides polynucleotides consisting of the consensus sequence as set forth in SEQ ID NO:43, or the complement of this sequence, that can be used as a target sequence for the design of primers and/or probes for the specific detection of *E. coli* O157:H7. In another embodiment, the present invention provides isolated polynucleotides consisting of conserved sequence #1 as set forth in SEQ ID NO:19 (shown in FIG. 7), or the complement of this sequence, that can be used as a target sequence for the design of primers and/or probes for the specific detection of *E. coli* O157:H7. In a further embodiment, the present invention provides isolated polynucleotides consisting of conserved sequence #2 as set forth in SEQ ID NO:29 (shown in FIG. 8), or the complement of this sequence, that can be used as a target sequence for the design of primers and/or probes for the specific detection of *E. coli* O157:H7.

In a further embodiment, the present invention provides polynucleotides consisting of the consensus sequence as set forth in SEQ ID NO:43, or the complement of this sequence, that can be used as a target sequence for the design of primers and/or probes for the detection of *E. coli* O157:H7 and verotoxin producing isolates of *E. coli* O157:NM. In another embodiment, the present invention provides isolated polynucleotides consisting of conserved sequence #1 as set forth in SEQ ID NO:19 (shown in FIG. 7), or the complement of this sequence, that can be used as a target sequence for the design of primers and/or probes for the detection of *E. coli* O157:H7 and verotoxin producing isolates of *E. coli* O157:NM. In a further embodiment, the present invention provides isolated polynucleotides consisting of conserved sequence #2 as set forth in SEQ ID NO:29 (shown in FIG. 8), or the complement of this sequence, that can be used as a target sequence for the design of primers and/or probes for the detection of *E. coli* O157:H7 and verotoxin producing isolates of *E. coli* O157:NM.

It will be recognised by those skilled in the art that all, or a portion or fragment, of the consensus sequence set forth in SEQ ID NO:43 or complement thereof can be used as target sequences to design primers and/or probes for the specific detection of *E. coli* O157:H7 and/or *E. coli* O157:NM which produces verotoxin. In one embodiment of the invention, target sequences are provided comprising at least 15% of the sequence set forth in SEQ ID NO:43. In a further embodiment, the target sequences comprise 20% of the sequence set forth in SEQ ID NO:43, or the complement thereof. In a further embodiment, the target sequences comprise at least 25% of the sequence set forth in SEQ ID NO:43, or the complement thereof. Target sequences comprising at least 30%, 35%, 40%, 45%, 50%, 55%, 60%, 70%, 75%, 85%, 90%, 95% and 98% of the sequence set forth in SEQ ID NO:43, or the complement thereof, are also contemplated.

It will be further recognised by those skilled in the art that all, or a portion or fragment, of conserved sequences within the consensus sequence can be used as target sequences for the specific detection of *E. coli* O157:H7 and/or *E. coli* O157:NM which produces verotoxin. Accordingly it will be recognised by those skilled in the art that all, or a portion of conserved sequence #1 set forth in SEQ ID NO: 19 or complement thereof, or all, or a portion of conserved sequence #2 set forth in SEQ ID NO:29 or complement thereof, can be used as target sequences.

In one embodiment of the invention, target sequences are provided comprising at least 65% of the sequence set forth in SEQ ID NO:19, or the complement thereof. In another embodiment, the target sequences comprise at least 70% of the sequence set forth in SEQ ID NO:19, or the complement thereof. In another embodiment, the target sequences comprise at least 75% of the sequence set forth in SEQ ID NO:19, or the complement thereof. In a further embodiment, the target sequences comprise at least 80% of the sequence set forth in SEQ ID NO:19, or the complement thereof. Target sequences comprising at least 85%, 90%, 95% and 98% of the sequence set forth in SEQ ID NO:19, or the complement thereof, are also contemplated.

In one embodiment of the invention, target sequences are provided comprising at least 75% of the sequence set forth in SEQ ID NO:29, or the complement thereof. In a further embodiment, the target sequences comprise at least 80% of the sequence set forth in SEQ ID NO:29, or the complement thereof. Target sequences comprising at least 85%, 90%, 95% and 98% of the sequence set forth in SEQ ID NO:29, or the complement thereof, are also contemplated.

Alternatively, such portions or fragments of the consensus sequence can be expressed in terms of consecutive nucleotides of the sequence set forth in SEQ ID NO:43. Accordingly, target sequences comprising portions of the consensus sequence that include at least 50, at least 55, at least 60, at least 65, at least 70, at least 75, at least 80, at least 85, at least 90, at least 95, at least 100, at least 105, at least 110, at least 120, at least 125, at least 130, at least 135, at least 140, at least 145, at least 150, at least 155, at least 160, at least 165, at least 170, at least 175, at least 180, at least 185, at least 190, at least 195, at least 200, at least 205, at least 210, at least 215, at least 220, at least 225, at least 230, at least 235, at least 240, at least 245, at least 250, at least 255, at least 260, and at least 265 consecutive nucleotides of the sequence set forth in SEQ ID NO:43, or the complement thereof, are contemplated. By way of illustration, a target sequence comprising a portion of a consensus sequence of "at least 50 consecutive nucleotides" means that the target sequence may comprise any series of consecutive nucleotides between 50 nucleotides and the full length of the sequence set forth in SEQ ID NO:43 (which is 269 nucleotides in length); thus this range includes portions of the consensus sequence that comprise at least 50, at least 51, at least 52, at least 53, etc, consecutive nucleotides of the sequence set forth in SEQ ID NO:43.

Such portions or fragments of conserved sequence #1 can also be expressed in terms of consecutive nucleotides of the sequence set forth in SEQ ID NO: 19. Accordingly, target sequences comprising portions of the consensus sequences that include at least 50, at least 55, at least 58, at least 60, at least 62, at least 64, at least 66, at least 68, at least 70, at least 72 and at least 74 consecutive nucleotides of the sequence set forth in SEQ ID NO: 19, or the complement thereof, are contemplated. By way of illustration, a target sequence comprising a portion of a conserved sequence of "at least 50 consecutive nucleotides" means that the target sequence may comprise any series of consecutive nucleotides between 50 nucleotides and the full length of the sequence set forth in SEQ ID NO:19 (which is 75 nucleotides in length); thus this range includes portions of the conserved sequence that comprise at least 51, at least 52, at least 53, at least 54, etc, consecutive nucleotides of the sequence set forth in SEQ ID NO:19.

Such portions or fragments of conserved sequence #2 can also be expressed in terms of consecutive nucleotides of the sequence set forth in SEQ ID NO:29. Accordingly, target sequences comprising portions of the consensus sequences that include at least 160, at least 165, at least 170, at least 175, at least 180, at least 185, at least 190, at least 195, at least 200 and at least 205 consecutive nucleotides of the sequence set forth in SEQ ID NO:29, or the complement thereof, are contemplated. By way of illustration a target sequence comprising a portion of a conserved sequence of "at least 160 consecutive nucleotides" means that the target sequence may comprise any series of consecutive nucleotides between 160 nucleotides and the full length of the sequence set forth in SEQ ID NO:29 (which is 208 nucleotides in length); thus this range includes portions of the conserved sequence that comprise at least 161, at least 162, at least 68, at least 69, etc, consecutive nucleotides of the sequence set forth in SEQ ID NO:29.

Within the identified conserved sequence # 1, an additional highly conserved region was identified. This highly conserved region of conserved sequence #1 is 21 nucleotides in length and has a sequence corresponding to SEQ ID NO:20 (as shown in FIG. 7C). Within the identified conserved sequence #2, an additional highly conserved region was also identified. This highly conserved region of conserved sequence #2 is 28 nucleotides in length and has a sequence corresponding to SEQ ID NO:30 (as shown in FIG. 8C). Accordingly, one embodiment of the present invention provides for target sequences that comprise all or a portion of a sequence corresponding to SEQ ID NO:20, or the complement thereof. In another embodiment of the present invention provides for target sequences that comprise all or a portion of a sequence corresponding to SEQ ID NO:30, or the complement thereof.

It will also be appreciated that the target sequences may include additional nucleotide sequences that are found upstream and/or downstream of the consensus sequence. As the assays provided by the present invention typically include an amplification step, it may be desirable to select an overall length for the target sequence such that the assay can be conducted fairly rapidly. Thus, the target sequence typically has an overall length of less than about 500 nucleotides. In one embodiment, the target sequence has an overall length of less than about 400 nucleotides. In another embodiment, the target sequence has an overall length of less than about 350 nucleotides. In other embodiments, the target sequence has an overall length of less than or equal to about 300, about 250, about 200, and about 150 nucleotides.

The present invention provides for polynucleotides for the amplification and/or detection of nucleic acids from E. coli O157:H7 and/or nucleic acids from E. coli O157:NM which produces verotoxin in a sample. The polynucleotide primers and probes of the invention comprise a sequence that corresponds to, or is complementary to, the portion of the E. coli O157:H7 gnd gene shown in SEQ ID NO:1 and are capable of specifically hybridizing to target sequence. In one embodiment, the polynucleotides of the invention comprise a sequence that corresponds to, or is complementary to, a portion of the E. coli 01577:H7 gnd gene sequence as set forth in any one of SEQ ID NOs:2-11 and are capable of specifically hybridizing to target sequence.

The polynucleotides of the present invention are generally between about 7 and about 100 nucleotides in length. One skilled in the art will understand that the optimal length for a selected polynucleotide will vary depending on its intended application (i.e. primer, probe or combined primer/probe) and on whether any additional features, such as tags, self-complementary "stems" and labels (as described below), are to be incorporated. In one embodiment of the present invention, the polynucleotides are between about 10 and about 100 nucleotides in length. In another embodiment, the polynucleotides are between about 12 and about 100 nucleotides in length. In other embodiments, the polynucleotides are between about 12 and about 50 nucleotides and between 12 and 40 nucleotides in length.

One skilled in the art will also understand that the entire length of the polynucleotide primers or probes of the invention does not need to correspond to or be complementary to its target sequence within the E. coli O157:H7 gnd gene in order to specifically hybridize thereto. Thus, the polynucleotide primers and probes may comprise nucleotides at the 5' and/or 3' termini that are not complementary to the target sequence. Such non-complementary nucleotides may provide additional functionality to the primer/probe, for example, they may provide a restriction enzyme recognition sequence or a "tag" that facilitates detection, isolation or purification. Alternatively, the additional nucleotides may provide a self-complementary sequence that allows the primer/probe to adopt a hairpin configuration. Such configurations are necessary for certain probes, for example, molecular beacon and Scorpion probes. In a further alternative, the primers and probes may comprise one or more regions of nucleotides which are complementary to the target sequence, separated by non-complementary nucleotides.

The present invention also contemplates that one or more positions within the polynucleotide can be degenerate, i.e. can be filled by one of two or more alternate nucleotides. As is known in the art, certain positions in a gene can vary in the nucleotide that is present at that position depending on the strain of bacteria that the gene originated from. Degenerate primers or probes are typically prepared by synthesising a "pool" of polynucleotide primers or probes that contains approximately equal amounts of polynucleotides containing the appropriate nucleotide at the degenerate position. By way of example, a polynucleotide having a degenerate position that could be filled by either an "A" or a "G" would be prepared by synthesizing a pool of polynucleotides containing approximately equal amounts of a polynucleotide having an A at the degenerate position and a polynucleotide containing a G at the degenerate position.

The polynucleotide primers and probes of the invention comprise a sequence of at least 7 consecutive nucleotides that correspond to or are complementary to a portion of the E. coli O157:H7 sequence shown in SEQ ID NO:1. In one embodiment, the polynucleotide primers and probes of the invention comprise a sequence of at least 7 consecutive nucleotides that correspond to or are complementary to a portion of the E. coli O157:H7 sequences shown in any one of SEQ ID NOs: 2-11.

As is known in the art, the optimal length of the sequence corresponding or complementary to the defined *E. coli* O157:H7 sequences will be dependent on the specific application for the polynucleotide, for example, whether it is to be used as a primer or a probe and, if the latter, the type of probe. Optimal lengths can be readily determined by the skilled artisan.

In one embodiment, the polynucleotides comprise at least 10 consecutive nucleotides corresponding or complementary to a portion of the *E. coli* O157:H7 sequence shown in SEQ ID NO:1. In another embodiment, the polynucleotides comprise at least 12 consecutive nucleotides corresponding or complementary to a portion of the *E. coli* O157:H7 sequence shown in SEQ ID NO:1. In a further embodiment, the polynucleotides comprise at least 15 consecutive nucleotides corresponding or complementary to a portion of the *E. coli* O157:H7 sequence shown in SEQ ID NO:1. Polynucleotides comprising at least 18, at least 20, at least 22, at least 24, at least 26, at least 27 and at least 28 consecutive nucleotides corresponding or complementary to a portion of the *E. coli* O157:H7 sequences shown in SEQ ID NO:1 are also contemplated.

In another embodiment, the polynucleotides comprise at least 10 consecutive nucleotides corresponding or complementary to a portion of the *E. coli* O157:H7 sequences shown in any one of SEQ ID NOs:2-11. In another embodiment, the polynucleotides comprise at least 12 consecutive nucleotides corresponding or complementary to a portion of the *E. coli* sequences shown in any one of SEQ ID NOs:2-11. In a further embodiment, the polynucleotides comprise at least 15 consecutive nucleotides corresponding or complementary to a portion of the *E. coli* O157:H7 sequences shown in any one of SEQ ID NOs:2-11. Polynucleotides comprising at least 18, at least 20, at least 22, at least 24, at least 26, at least 27 and at least 28 consecutive nucleotides corresponding or complementary to a portion of the *E. coli* O157:H7 sequences shown in any one of SEQ ID NOs:2-11 are also contemplated.

In another embodiment, the polynucleotides comprise at least 7 consecutive nucleotides corresponding or complementary to a portion of the sequence shown in SEQ ID NO: 43. In another embodiment, the polynucleotides comprise at least 10 consecutive nucleotides corresponding or complementary to a portion of the sequence shown in SEQ ID NO: 43. In another embodiment, the polynucleotides comprise at least 12 consecutive nucleotides corresponding or complementary to a portion of the sequence shown in SEQ ID NO:43. In a further embodiment, the polynucleotides comprise at least 15 consecutive nucleotides corresponding or complementary to a portion of the sequence shown in SEQ ID NO:43. Polynucleotides comprising at least 18, at least 20, at least 22, at least 24, at least 26, at least 27 and at least 28 consecutive nucleotides corresponding or complementary to a portion of the sequence shown in SEQ ID NO:43 are also contemplated.

In another embodiment, the polynucleotides comprise at least 7 consecutive nucleotides corresponding or complementary to a portion of the sequence shown in SEQ ID NO: 19. In another embodiment, the polynucleotides comprise at least 10 consecutive nucleotides corresponding or complementary to a portion of the sequence shown in SEQ ID NO: 19. In another embodiment, the polynucleotides comprise at least 12 consecutive nucleotides corresponding or complementary to a portion of the shown in SEQ ID NO:19. In a further embodiment, the polynucleotides comprise at least 15 consecutive nucleotides corresponding or complementary to a portion of the sequence shown in SEQ ID NO:19. Polynucleotides comprising at least 18, at least 20, at least 22, at least 24, at least 26, at least 27 and at least 28 consecutive nucleotides corresponding or complementary to a portion of the sequence shown in SEQ ID NO:19 are also contemplated.

In another embodiment, the polynucleotides comprise at least 7 consecutive nucleotides corresponding or complementary to a portion of the sequence shown in SEQ ID NO: 29. In another embodiment, the polynucleotides comprise at least 10 consecutive nucleotides corresponding or complementary to a portion of the sequence shown in SEQ ID NO: 29. In another embodiment, the polynucleotides comprise at least 12 consecutive nucleotides corresponding or complementary to a portion of the sequence shown in SEQ ID NO:29. In a further embodiment, the polynucleotides comprise at least 15 consecutive nucleotides corresponding or complementary to a portion of the sequence shown in SEQ ID NO:29. Polynucleotides comprising at least 18, at least 20, at least 22, at least 24, at least 26, at least 27 and at least 28 consecutive nucleotides corresponding or complementary to a portion of the sequence shown in SEQ ID NO:29 are also contemplated.

Sequences of exemplary polynucleotides of the invention are set forth in Table 1. Further non-limiting examples for the polynucleotides of the invention include polynucleotides that comprise at least 7 consecutive nucleotides of any one of SEQ ID NOs:21, 22, 24, 26, 27, 28, 31, 32, 34, 36, 37, 38, 40 and 42.

TABLE 1

Exemplary polynucleotides of the invention

| Nucleotide sequence | SEQ ID NO |
|---|---|
| 5'- AGGAGGGCGCACTA -3' | 21 |
| 5'- GGATCGGCGCAACT -3' | 22 |
| 5'- CCTGGTGGGCAGAAAGAAGCC -3' | 24 |
| 5'- GGCTTCTTTCTGCCCACCAGG -3' | 26 |
| 5'- TGGTGAGGAGGGCGCACTA -3' | 27 |
| 5'- GAATAGGCTTCAGCAATCAGC -3' | 28 |
| 5'- GCCTCGTCGCATCT -3' | 31 |
| 5'- TAGTGCGCCCTCCT -3' | 32 |
| 5'- CAGGCACGGATGCTGCTATTGATTCCCT -3' | 34 |
| 5'- AGGGAATCAATAGCAGCATCCGTGCCTG -3' | 36 |
| 5'- GGAAACGCCTCGTCGCATCT -3' | 37 |
| 5'- TAGTGCGCCCTCCTCACCA -3' | 38 |
| 5'- CCTTAAGCCATACCTCGATAA -3' | 40 |
| 5'- TTATCGAGGTATGGCTTAAGG -3' | 42 |

Primers

As indicated above, the polynucleotide primers of the present invention comprise a sequence that corresponds to or is complementary to a portion of the sequences shown in any one of SEQ ID NOs:1-11. In accordance with one aspect of the invention, the primers are capable of amplifying a target nucleotide sequence comprising all or a portion of the consensus sequence as shown in SEQ ID NO:43. In accordance with another aspect of the invention, the primers are capable of amplifying a target nucleotide sequence comprising all or a portion of the 75 nucleotide conserved sequence # 1 as shown in SEQ ID NO:19. In accordance with another aspect of the invention, the primers are capable of amplifying a target nucleotide sequence comprising all or a portion of the 208 nucleotide conserved sequence #2 as shown in SEQ ID NO:29. Accordingly in one embodiment, the present invention provides for primer pairs capable of amplifying a target nucleotide sequence, wherein the target sequence is less than about 500 nucleotides in length and comprises at least 160 consecutive nucleotides of SEQ ID NO:43, or the complement thereof. In another embodiment, the present invention provides for primer pairs capable of amplifying a target nucleotide sequence, wherein the target sequence is less than about 500 nucleotides in length and comprises at least 50 consecutive nucleotides of SEQ ID NO:19, or the complement thereof. In a further embodiment, the present invention provides for primer pairs capable of amplifying a target nucleotide sequence, wherein the target sequence is less than about 500 nucleotides in length and comprises at least 160 consecutive nucleotides of SEQ ID NO:29, or the complement thereof.

Thus, pairs of primers can be selected to comprise a forward primer corresponding to a portion of the gnd gene sequence upstream of, or within the region of the gene corresponding to SEQ ID NO:43 and a reverse primer that it is complementary to a portion of the gnd gene sequence downstream of, or within the region of the gene corresponding to SEQ ID NO:43. Pairs of primers can also be selected to comprise a forward primer corresponding to a portion of the gnd gene sequence upstream of, or within the region of the gene corresponding to SEQ ID NO:19 and a reverse primer that it is complementary to a portion of the gnd gene sequence downstream of or within the region of the gene corresponding to SEQ ID NO:19. In addition, pairs of primers can be selected to comprise a forward primer corresponding to a portion of the gnd gene sequence upstream of, or within the region of the gene corresponding to SEQ ID NO:29 and a reverse primer that it is complementary to a portion of the gnd gene sequence downstream of, or within the region of the gene corresponding to SEQ ID NO:29. In accordance with one embodiment of the present invention, the primers comprise at least 7 consecutive nucleotides of the sequence set forth in SEQ ID NO:1. In another embodiment, the primers comprise at least 7 consecutive nucleotides of the sequence as set forth in any one of SEQ ID NOs:2-11.

Appropriate primer pairs can be readily determined by a worker skilled in the art. In general, primers are selected that specifically hybridize to the appropriate region of the genome of *E. coli* O157:H7 and/or the genome of *E. coli* O157:NM which produce verotoxin. In addition, primers are selected that contain minimal sequence repeats and that demonstrate a low potential of forming dimers, cross dimers, or hairpin structures and of cross priming. Such properties can be determined by methods known in the art, for example, using the computer modelling program OLIGO® Primer Analysis Software (distributed by National Biosciences, Inc., Plymouth, Minn.).

Non-limiting examples of suitable primer sequences include SEQ ID NOs: 21, 22, 27, 28, 31; 32; 37 and 38 shown in Table 1, as well as primers comprising at least 7 consecutive nucleotides of any one of SEQ ID NOs:19, 21, 22, 24, 26, 27, 28, 29, 31, 32, 34, 36, 37, 38, 40, 42 and 43.

Probes

In order to specifically detect *E. coli* O157:H7 and/or *E. coli* O157:NM which produces verotoxin, the probe polynucleotides of the invention are designed to correspond to, or be complementary to a portion of the consensus sequence shown in SEQ ID NO:43. In one embodiment of the present invention, the probe polynucleotides of the invention are designed to correspond to, or be complementary to a portion of the conserved sequence #1 shown in SEQ ID NO:19. In a further embodiment, the probe polynucleotides of the invention are designed to correspond to, or be complementary to a portion of the conserved sequence #2 shown in SEQ ID NO:29. Accordingly, the probe polynucleotides comprise at least 7 consecutive nucleotides of the sequence set forth in SEQ ID NO:43, SEQ ID NO:19 or SEQ ID NO:29, or the complement thereof. As indicated above, highly conserved regions were identified within the conserved sequences #1 and #2. In one embodiment, therefore, the present invention provides for probe polynucleotides comprising at least 7 consecutive nucleotides of the sequence set forth in SEQ ID NO:20, or the complement thereof. In another embodiment the present invention provides for probe polynucleotides comprising at least 7 consecutive nucleotides of the sequence set forth in SEQ ID NO:30, or the complement thereof.

Non-limiting examples of suitable probe sequences include sequences that comprise SEQ ID NO:24, 26, 34, 36, 40 or 42 shown in Table 1, as well as probes comprising at least 7 consecutive nucleotides of any one of SEQ ID NOs: 19, 20, 21, 22, 24, 26, 27, 28, 29, 30, 31, 32, 34, 36, 37, 38, 40, 42 and 43. Various types of probes known in the art are contemplated by the present invention. For example, the probe may be a hybridization probe, the binding of which to a target nucleotide sequence can be detected using a general DNA binding dye such as ethidium bromide, SYBR® Green, SYBR® Gold and the like. Alternatively, the probe can incorporate one or more detectable labels. Detectable labels are molecules or moieties a property or characteristic of which can be detected directly or indirectly and are chosen such that the ability of the probe to hybridize with its target sequence is not affected. Methods of labelling nucleic acid sequences are well-known in the art (see, for example, Ausubel et al., (1997 & updates) *Current Protocols in Molecular Biology*, Wiley & Sons, New York).

Labels suitable for use with the probes of the present invention include those that can be directly detected, such as radioisotopes, fluorophores, chemiluminophores, enzymes, colloidal particles, fluorescent microparticles, and the like. One skilled in the art will understand that directly detectable labels may require additional components, such as substrates, triggering reagents, light, and the like to enable detection of the label. The present invention also contemplates the use of labels that are detected indirectly. Indirectly detectable labels are typically specific binding members used in conjunction with a "conjugate" that is attached or coupled to a directly detectable label. Coupling chemistries for synthesising such conjugates are well-known in the art and are designed such that the specific binding property of the specific binding member and the detectable property of the label remain intact. As used herein, "specific binding member" and "conjugate" refer to the two members of a binding pair, i.e. two different molecules, where the specific binding member binds specifically to the probe, and the "conjugate" specifically binds to the specific binding member. Binding between the two members of the pair is typically chemical or physical in nature. Examples of such binding pairs include, but are not limited to, antigens and antibodies; avidin/streptavidin and biotin; haptens and antibodies specific for haptens; complementary nucleotide sequences; enzyme cofactors/substrates and enzymes; and the like.

In one embodiment of the present invention, the probe is labelled with a fluorophore. The probe may additionally incorporate a quencher for the fluorophore. Fluorescently labelled probes can be particularly useful for the real-time detection of target nucleotide sequences in a test sample. Examples of probes that are labelled with both a fluorophore and a quencher that are contemplated by the present invention include, but are not limited to, molecular beacon probes and TaqMan® probes. Such probes are well known in the art (see for example, U.S. Pat. Nos. 6,150,097; 5,925,517 and 6,103,476; Marras et al., "*Genotyping single nucleotide polymorphisms with molecular beacons*". In Kwok, P.Y. (ed.), "Single nucleotide polymorphisms: methods and protocols,". Vol. 212, pp. 111-128, Humana Press, Totowa, N.J.)

Figure 3:
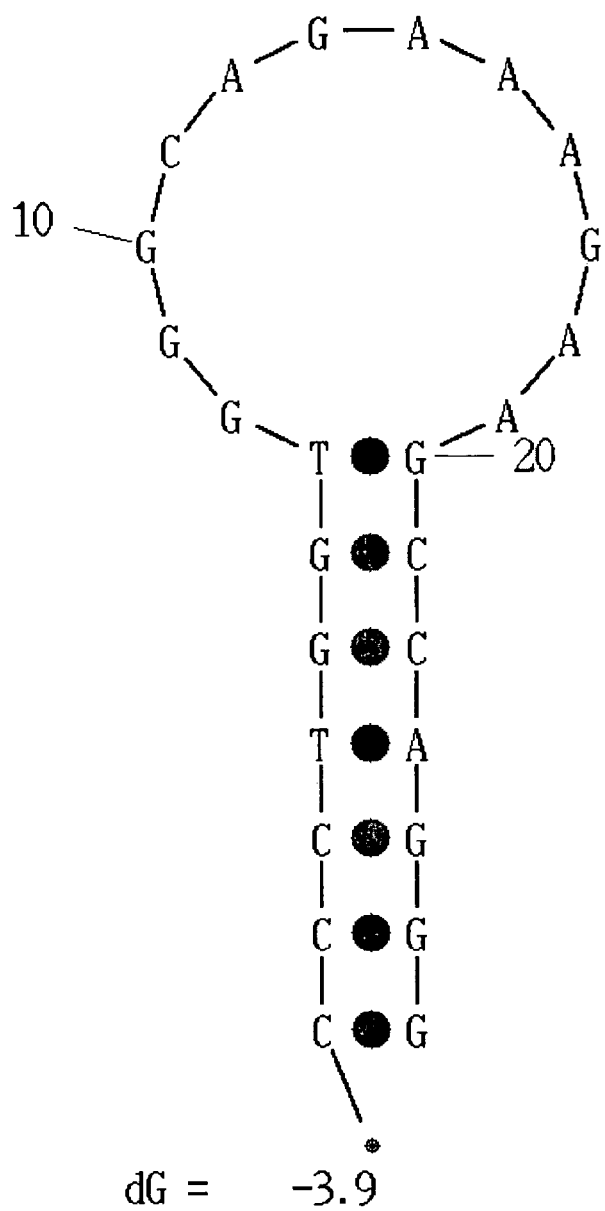
FIG. 3 presents the secondary structure of the molecular beacon probe #1 in accordance with one embodiment of the invention [SEQ ID NO:23]
Figure 6:
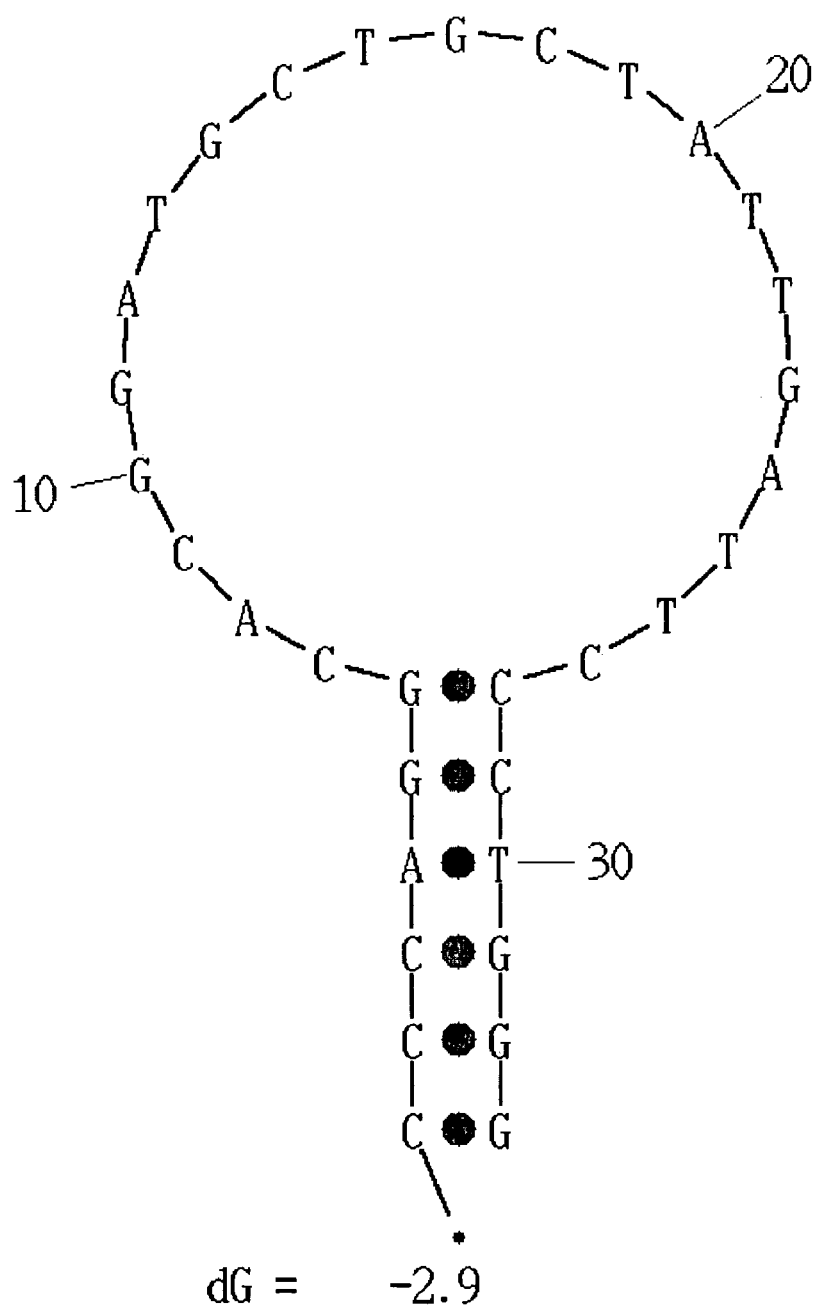
FIG. 6 presents the secondary structure of the molecular beacon probe #2 in accordance with one embodiment of the invention [SEQ ID NO:33]

A molecular beacon probe is a hairpin shaped oligonucleotide sequence, which undergoes a conformational change when it hybridizes to a perfectly complementary target sequence. The secondary structure of a typical molecular beacon probe includes a loop sequence, which is capable of hybridizing to a target sequence and a pair of arm (or "stem") sequences. One arm is attached to a fluorophore, while the other arm is attached to a quencher. The arm sequences are complementary to each other so as to enable the arms to hybridize together to form a molecular duplex and the beacon adopts a hairpin conformation in which the fluorophore and quencher are in close proximity and interact such that emission of fluorescence is prevented. Hybridization between the loop sequence and the target sequence forces the molecular beacon probe to undergo a conformational change in which arm sequences are forced apart and the fluorophore is physically separated from the quencher. As a result, the fluorescence of the fluorophore is restored. The fluorescence generated can be monitored and related to the presence of the target nucleotide sequence. If no target sequence is present in the sample, no fluorescence will be observed. This methodology, as described further below, can also be used to quantify the amount of target nucleotide in a sample. By way of example, FIGS. 3 and 6 depict the secondary structure of exemplary hairpin loop molecular beacons having sequences corresponding to SEQ ID NO:23 and 33, respectively.

Wavelength-shifting molecular beacon probes which incorporate two fluorophores, a "harvester fluorophore and an "emitter" fluorophore (see, Kramer, et al., (2000) *Nature Biotechnology*, 18:1191-1196) are also contemplated. When a wavelength-shifting molecular beacon binds to its target sequence and the hairpin opens, the energy absorbed by the harvester fluorophore is transferred by fluorescence resonance energy transfer (FRET) to the emitter, which then fluoresces. Wavelength-shifting molecular beacons are particularly suited to multiplex assays.

TaqMan® probes are dual-labelled fluorogenic nucleic acid probes that function on the same principles as molecular beacons. TaqMan® probes are composed of a polynucleotide that is complementary to a target sequence and is labelled at the 5' terminus with a fluorophore and at the 3' terminus with a quencher. TaqMan® probes, like molecular beacons, are typically used as real-time probes in amplification reactions. In the free probe, the close proximity of the fluorophore and the quencher ensures that the fluorophore is internally quenched. During the extension phase of the amplification reaction, the probe is cleaved by the 5' nuclease activity of the polymerase and the fluorophore is released. The released fluorophore can then fluoresce and produce a detectable signal.

Linear probes comprising a fluorophore and a high efficiency dark quencher, such as the Black Hole Quenchers (BHQ™; Biosearch Technologies, Inc., Novato, Calif.) are also contemplated. As is known in the art, the high quenching efficiency and lack of native fluorescence of the BHQ™ dyes allows "random-coil" quenching to occur in linear probes labelled at one terminus with a fluorophore and at the other with a BHQ™ dye thus ensuring that the fluorophore does not fluoresce when the probe is in solution. Upon binding its target sequence, the probe stretches out spatially separating the fluorophore and quencher and allowing the fluorophore to fluoresce. One skilled in the art will appreciate that the BHQ™ dyes can also be used as the quencher moiety in molecular beacon or TaqMan® probes.

As an alternative to including a fluorophore and a quencher in a single molecule, two fluorescently labelled probes that anneal to adjacent regions of the target sequence can be used. One of these probes, a donor probe, is labelled at the 3' end with a donor fluorophore, such as fluorescein, and the other probe, the acceptor probe, is labelled at the 5' end with an acceptor fluorophore, such as LC Red 640 or LC Red 705. When the donor fluorophore is stimulated by the excitation source, energy is transferred to the acceptor fluorophore by FRET resulting in the emission of a fluorescent signal.

In addition to providing primers and probes as separate molecules, the present invention also contemplates polynucleotides that are capable of functioning as both primer and probe in an amplification reaction. Such combined primer/probe polynucleotides are known in the art and include, but are not limited to, Scorpion probes, duplex Scorpion probes, Lux™ primers and Amplifluor™ primers.

Scorpion probes consist of, from the 5' to 3' end, (i) a fluorophore, (ii) a specific probe sequence that is complementary to a portion of the target sequence and is held in a hairpin configuration by complementary stem loop sequences, (iii) a quencher, (iv) a PCR blocker (such as, hexethylene glycol) and (v) a primer sequence. After extension of the primer sequence in an amplification reaction, the probe folds back on itself so that the specific probe sequence can bind to its complement within the same DNA strand.

This opens up the hairpin and the fluorophore can fluoresce. Duplex Scorpion probes are a modification of Scorpion probes in which the fluorophore-coupled probe/primer containing the PCR blocker and the quencher-coupled sequence are provided as separate complementary polynucleotides. When the two polynucleotides are hybridized as a duplex molecule, the fluorophore is quenched. Upon dissociation of the duplex when the primer/probe binds the target sequence, the fluorophore and quencher become spatially separated and the fluorophore fluoresces.

The Amplifluor Universal Detection System also employs fluorophore/quencher combinations and is commercially available from Chemicon International (Temecula, Calif.).

In contrast, Lux™ primers incorporate only a fluorophore and adopt a hairpin structure in solution that allows them to self-quench. Opening of the hairpin upon binding to a target sequence allows the fluorophore to fluoresce.

Suitable fluorophores and/or quenchers for use with the polynucleotides of the present invention are known in the art (see for example, Tyagi et al., *Nature Biotechnol.*, 16:49-53 (1998); Marras et al., *Genet. Anal.: Biomolec. Eng.*, 14:151-156 (1999)). Many fluorophores and quenchers are available commercially, for example from Molecular Probes (Eugene, Oreg.) or Biosearch Technologies, Inc. (Novato, Calif.). Examples of fluorophores that can be used in the present invention include, but are not limited to, fluorescein and fluorescein derivatives, such as 6-carboxyfluoroscein (FAM), 5'-tetrachlorofluorescein phosphoroamidite (TET), tetrachloro-6-carboxyfluoroscein, VIC and JOE, 5-(2'-aminoethyl)aminonaphthalene-1-sulphonic acid (EDANS), coumarin and coumarin derivatives, Lucifer yellow, Texas red, tetramethylrhodamine, 5-carboxyrhodamine, cyanine dyes (such as Cy5) and the like. Pairs of fluorophores suitable for use as FRET pairs include, but are not limited to, fluorescein/rhodamine, fluorescein/Cy5, fluorescein/Cy5.5, fluorescein/LC Red 640, fluorescein/LC Red 750, and phycoerythrin/

Cy7. Quenchers include, but are not limited to, 4'-(4-dimethylaminophenylazo)benzoic acid (DABCYL), 4-dimethylaminophenylazophenyl-4'-maleimide (DABMI), tetramethylrhodamine, carboxytetramethylrhodamine (TAMRA), BHQ™ dyes and the like.

Methods of selecting appropriate sequences for and preparing the various primers and probes are known in the art. For example, the polynucleotides can be prepared using conventional solid-phase synthesis using commercially available equipment, such as that available from Applied Biosystems USA Inc. (Foster City, Calif.), DuPont, (Wilmington, Del.), or Milligen (Bedford, Mass.). Methods of coupling fluorophores and quenchers to nucleic acids are also in the art.

In one embodiment of the present invention, the probe polynucleotide is a molecular beacon. In general, in order to form a hairpin structure effectively, molecular beacons are at least 17 nucleotides in length. In accordance with this aspect of the invention, therefore, the molecular beacon probe is typically between about 17 and about 40 nucleotides in length. Non-limiting examples of molecular beacon probes of the present invention include SEQ ID NOs: 23, 25, 33, 35, 39 and 41. Within the probe, the loop sequence that corresponds to or is complementary to the target sequence typically is about 7 to about 32 nucleotides in length, while the stem (or arm) sequences are each between about 4 and about 9 nucleotides in length. As indicated above, part of the stem sequences of a molecular beacon may also be complementary to the target sequence. In one embodiment of the present invention, the loop sequence of the molecular beacon is between about 10 and about 32 nucleotides in length. In other embodiments, the loop sequence of the molecular beacon is between about 15 and about 30 nucleotides in length.

In accordance with one embodiment of the present invention, the loop region of the molecular beacon probe comprises at least 7 consecutive nucleotides of the sequence as set forth in SEQ ID NO:43, or the complement thereof. In accordance with another embodiment of the present invention, the loop region of the molecular beacon probe comprises at least 7 consecutive nucleotides of the sequence as set forth in SEQ ID NO:19, or the complement thereof. In another embodiment, the loop region of the molecular beacon probe comprises at least 7 consecutive nucleotides of the sequence as set forth in SEQ ID NO:24, 26, or the complement thereof. In another embodiment, the loop region of the molecular beacon probe comprises at least 7 consecutive nucleotides of the sequence as set forth in SEQ ID NO: 29, or the complement thereof. In a further embodiment, the loop region of the molecular beacon probe comprises at least 7 consecutive nucleotides of the sequence as set forth in SEQ ID NO: 34, 36, 40, 42, or the complement thereof.

Amplification and Detection

In accordance with one embodiment of the present invention, detection of *E. coli* O157:H7 and/or *E. coli* O157:NM which produces verotoxin involves subjecting a test sample to an amplification reaction in order to obtain an amplification product, or amplicon comprising the target sequence.

As used herein, an "amplification reaction" refers to a process that increases the number of copies of a particular nucleic acid sequence by enzymatic means. Amplification procedures are well-known in the art and include, but are not limited to, polymerase chain reaction (PCR), TMA, rolling circle amplification, nucleic acid sequence based amplification (NASBA), strand displacement amplification (SDA) and Q-beta replicase amplification. One skilled in the art will understand that for use in certain amplification techniques the primers described above may need to be modified, for example, SDA primers comprise additional nucleotides near the 5' end that constitute a recognition site for a restriction endonuclease. Similarly, NASBA primers comprise additional nucleotides near the 5' end that are not complementary to the target sequence but which constitute an RNA polymerase promoter. Polynucleotides thus modified are considered to be within the scope of the present invention.

In one embodiment of the present invention, the target sequence is amplified by PCR. PCR is a method known in the art for amplifying a nucleotide sequence using a heat stable polymerase and a pair of primers, one primer (the forward primer) complementary to the (+)-strand at one end of the sequence to be amplified and the other primer (the reverse primer) complementary to the (−)-strand at the other end of the sequence to be amplified. Newly synthesized DNA strands can subsequently serve as templates for the same primer sequences and successive rounds of strand denaturation, primer annealing, and strand elongation, produce rapid and highly specific amplification of the target sequence. PCR can thus be used to detect the existence of a defined sequence in a DNA sample. The term "PCR" as used herein refers to the various forms of PCR known in the art including, but not limited to, quantitative PCR, reverse-transcriptase PCR, real-time PCR, hot start PCR, long PCR, LAPCR, multiplex PCR, touchdown PCR, and the like. "Real-time PCR" refers to a PCR reaction in which the amplification of a target sequence is monitored in real time by, for example, the detection of fluorescence emitted by the binding of a labelled probe to the amplified target sequence.

In one embodiment, the present invention provides for amplification of a portion of a gnd gene of *E. coli* O157:H7 and/or a gnd gene of *E. coli* O157:NM which produces verotoxin of less than about 500 nucleotides in length and comprising at least 50 consecutive nucleotides of the sequence set forth in SEQ ID NO:43 using pairs of polynucleotide primers, each member of the primer pair comprising at least 7 nucleotides of the sequence as set forth in SEQ ID NO:1, or the complement thereof. In another embodiment, the present invention provides for amplification of a portion of a gnd gene of *E. coli* O157:H7 and/or a gnd of *E. coli* O157:NM which produces verotoxin of less than about 500 nucleotides in length and comprising at least 50 consecutive nucleotides of the sequence set forth in SEQ ID NO:43 using pairs of polynucleotide primers, each member of the primer pair comprising at least 7 nucleotides of the sequence as set forth in any one of SEQ ID NOs:2-11, or the complement thereof. In another embodiment, the present invention provides for amplification of a portion of a gnd gene of *E. coli* O157:H7 and/or a gnd gene of *E. coli* O157:NM which produces verotoxin of less than about 500 nucleotides in length and comprising at least 50 consecutive nucleotides of the sequence set forth in SEQ ID NO:19 using pairs of polynucleotide primers, each member of the primer pair comprising at least 7 nucleotides of the sequence as set forth in SEQ ID NO:1, or the complement thereof. In another embodiment, the present invention provides for amplification of a portion of a gnd gene of *E. coli* O157:H7 and/or a gnd gene of *E. coli* O157:NM which produces verotoxin of less than about 500 nucleotides in length and comprising at least 50 consecutive nucleotides of the sequence set forth in SEQ ID NO:19 using pairs of polynucleotide primers, each member of the primer pair comprising at least 7 nucleotides of the sequence as set forth in any one of SEQ ID NOs:2-11, or the complement thereof. In another embodiment, the present invention provides for amplification of a portion of a gnd gene of *E. coli* O157:H7 and/or a gnd gene of *E. coli* O157:NM which produces verotoxin of less than about 500 nucleotides in length and comprising at least 160 consecutive nucleotides of the sequence set forth in SEQ ID NO:29 using pairs of polynucleotide primers, each member of the primer pair comprising at least 7 nucleotides of the sequence as set forth in SEQ ID NO:1, or the complement thereof. In another embodiment, the present invention provides for amplification of a portion of a gnd gene of *E. coli* O157:H7 and/or a gnd gene of *E. coli* O157:NM which produces verotoxin of less than about 500 nucleotides in length and comprising at least 160 consecutive nucleotides of the sequence set forth in SEQ ID NO:29 using pairs of polynucleotide primers, each member of the primer pair comprising at least 7 nucleotides of the sequence as set forth in any one of SEQ ID NOs:2-11, or the complement thereof.

The product of the amplification reaction can be detected by a number of means known to individuals skilled in the art. Examples of such detection means include, for example, gel electrophoresis and/or the use of polynucleotide probes. In one embodiment of the invention, the amplification products are detected through the use of polynucleotide probes. Such polynucleotide probes are described in detail above.

One embodiment of the invention, therefore, provides for amplification and detection of a portion of a gnd gene of *E. coli* O157:H7 and/or a gnd gene of *E. coli* O157:NM which produces verotoxin of less than about 500 nucleotides in length and comprising at least 50 consecutive nucleotides of the sequence set forth in SEQ ID NO:43 using a combination of polynucleotides, the combination comprising one or more polynucleotide primers comprising at least 7 nucleotides of the sequence as set forth in SEQ ID NO:1, or the complement thereof, and a polynucleotide probe comprising at least 7 consecutive nucleotides of the sequence as set forth in SEQ ID NO:43, or the complement thereof.

Another embodiment of the invention, therefore, provides for amplification and detection of a portion of a gnd gene of *E. coli* O157:H7 and/or a gnd gene of *E. coli* O157:NM which produces verotoxin of less than about 500 nucleotides in length and comprising at least 50 consecutive nucleotides of the sequence set forth in SEQ ID NO:43 using a combination of polynucleotides, the combination comprising one or more polynucleotide primers comprising at least 7 nucleotides of the sequence as set forth in any one of SEQ ID NOs:2-11, or the complement thereof, and a polynucleotide probe comprising at least 7 consecutive nucleotides of the sequence as set forth in SEQ ID NO:43, or the complement thereof.

Another embodiment of the invention, therefore, provides for amplification and detection of a portion of a gnd gene of *E. coli* O157:H7 and/or a gnd gene of *E. coli* O157:NM which produces verotoxin of less than about 500 nucleotides in length and comprising at least 50 consecutive nucleotides of the sequence set forth in SEQ ID NO:19 using a combination of polynucleotides, the combination comprising one or more polynucleotide primers comprising at least 7 nucleotides of the sequence as set forth in SEQ ID NO:1, or the complement thereof, and a polynucleotide probe comprising at least 7 consecutive nucleotides of the sequence as set forth in SEQ ID NO:19, or the complement thereof.

Another embodiment of the invention, therefore, provides for amplification and detection of a portion of a gnd gene of *E. coli* O157:H7 and/or a gnd gene of *E. coli* O157:NM which produces verotoxin of less than about 500 nucleotides in length and comprising at least 50 consecutive nucleotides of the sequence set forth in SEQ ID NO:19 using a combination of polynucleotides, the combination comprising one or more polynucleotide primers comprising at least 7 nucleotides of the sequence as set forth in any one of SEQ ID NOs:2-11, or the complement thereof, and a polynucleotide probe comprising at least 7 consecutive nucleotides of the sequence as set forth in SEQ ID NO:19, or the complement thereof.

A further embodiment of the invention, therefore, provides for amplification and detection of a portion of a gnd gene of *E. coli* O157:H7 and/or a gnd gene of *E. coli* O157:NM which produces verotoxin of less than about 500 nucleotides in length and comprising at least 160 consecutive nucleotides of the sequence set forth in SEQ ID NO:29 using a combination of polynucleotides, the combination comprising one or more polynucleotide primers comprising at least 7 nucleotides of the sequence as set forth in SEQ ID NO:1, or the complement thereof, and a polynucleotide probe comprising at least 7 consecutive nucleotides of the sequence as set forth in SEQ ID NO:29, or the complement thereof.

A still further embodiment of the invention, therefore, provides for amplification and detection of a portion of a gnd gene of *E. coli* O157:H7 and/or a gnd gene of *E. coli* O157:NM which produces verotoxin of less than about 500 nucleotides in length and comprising at least 160 consecutive nucleotides of the sequence set forth in SEQ ID NO:29 using a combination of polynucleotides, the combination comprising one or more polynucleotide primers comprising at least 7 nucleotides of the sequence as set forth in any one of SEQ ID NOs:2-11, or the complement thereof, and a polynucleotide probe comprising at least 7 consecutive nucleotides of the sequence as set forth in SEQ ID NO:29, or the complement thereof.

It will be readily appreciated that a procedure that allows both amplification and detection of target nucleic acid sequences to take place in a single reaction vessel would be advantageous. This single reaction vessel may be sealed following addition of the test samples and/or necessary reagents. Such a procedure would avoid the risk of "carry-over" contamination in the post-amplification processing steps, and would also facilitate high-throughput screening or assays and the adaptation of the procedure to automation. Furthermore, this type of procedure allows "real time" monitoring of the amplification reaction, as discussed above, as well as more conventional "end-point" monitoring. In one embodiment, the detection is accomplished in real time in order to facilitate rapid detection. In a specific embodiment, detection is accomplished in real time through the use of molecular beacon probes.

The present invention thus provides for methods to specifically amplify and detect target nucleic acid sequences in a test sample in a single tube format using the polynucleotide primers, and optionally one or more probes, described herein. Such methods may employ dyes, such as SYBR® Green or SYBR® Gold that bind to the amplified target sequence, or an antibody that specifically detects the amplified target sequence. The dye or antibody is included in the reaction vessel and detects the amplified sequences as it is formed. Alternatively, a labelled polynucleotide probe (such as a molecular beacon or TaqMan® probe) distinct from the primer sequences, which is complementary to a region of the amplified sequence, may be included in the reaction, or one of the primers may act as a combined primer/probe, such as a Scorpion probe. Such options are discussed in detail above.

Thus, a general method of detecting *E. coli* O157:H7 and/or *E. coli* O157:NM which produces verotoxin in a sample is provided that comprises contacting a test sample with a combination of polynucleotides comprising at least one polynucleotide primer and at least one polynucleotide probe or primer/probe, as described above, under conditions that permit amplification of one or more target sequence(s), and detecting any amplified target sequence(s) as an indication of the presence of *E. coli* O157:H7 and/or the presence of *E. coli* O157:NM which produces verotoxinin the sample. A "test sample" as used herein is a biological sample suspected of containing, or known to contain, one or more *E. coli* O157:H7 target nucleotide sequences and/or one or more *E. coli* O157:NM which produces verotoxin.

In one embodiment of the present invention, a method using the polynucleotide primers and probes or primer/probes is provided to specifically amplify and detect a target nucleotide from *E. coli* O157:H7 and/or *E. coli* O157:NM which produces verotoxin sequence in a test sample, the method generally comprising the steps of:

(a) forming a reaction mixture comprising a test sample, amplification reagents, one or more polynucleotide probes capable of specifically hybridising to a portion of the target nucleotide sequence and one or more polynucleotide primers corresponding to or complementary to a portion of a gnd gene from *E. coli* O157:H7 and/or a gnd gene from *E. coli* O157:NM which produces verotoxin comprising said target nucleotide sequence;

(b) subjecting the mixture to amplification conditions to generate at least one copy of the target nucleotide sequence, or a nucleic acid sequence complementary to the target nucleotide sequence;

(c) hybridizing the probe to the target nucleotide sequence or the nucleic acid sequence complementary to the target sequence, so as to form a probe:target hybrid; and (d) detecting the probe:target hybrid as an indication of the presence of the target nucleotide sequence in the test sample.

In one embodiment of the present invention, the method employs one or more labelled probes in step(a).

The term "amplification reagents" includes conventional reagents employed in amplification reactions and includes, but is not limited to, one or more enzymes having nucleic acid polymerase activity, enzyme cofactors (such as magnesium or nicotinamide adenine dinucleotide (NAD)), salts, buffers, nucleotides such as deoxynucleotide triphosphates (dNTPs; for example, deoxyadenosine triphosphate, deoxyguanosine triphosphate, deoxycytidine triphosphate and deoxythymidine triphosphate) and other reagents that modulate the activity of the polymerase enzyme or the specificity of the primers.

It will be readily understood by one skilled in the art that step (b) of the above method can be repeated several times prior to step (c) by thermal cycling the reaction mixture by techniques known in the art and that steps (b), (c) and (d) may take place concurrently such that the detection of the amplified sequence takes place in real time. In addition, variations of the above method can be made depending on the intended application of the method, for example, the polynucleotide probe may be a combined primer/probe, or it may be a separate polynucleotide probe, in which case two different polynucleotide primers are used. Additional steps may be incorporated before, between or after those listed above as necessary, for example, the test sample may undergo enrichment, extraction and/or purification steps to isolate nucleic acids therefrom prior to the amplification reaction, and/or the amplified product may be submitted to purification/isolation steps or further amplification prior to detection, and/or the results from the detection step (d) may be analysed in order to quantify the amount of target present in the sample or to compare the results with those from other samples. These and other variations will be apparent to one skilled in the art and are considered to be within the scope of the present invention.

Diagnostic Assays to Detect *E. coli* O157:H7 and/or *E. coli* O157:NM Verotoxin Producers The present invention provides for diagnostic assays using the polynucleotide primers and/or probes that can be used for highly specific and sensitive detection of one or more isolates of *E. coli* O157:H7 and/or one or more *E. coli* O157:NM which produces verotoxin in a test sample. The diagnostic assays comprise amplification and detection of nucleic acids from *E. coli* O157:H7 and/or *E. coli* O157:NM which produces verotoxin as described above. The diagnostic assays can be qualitative or quantitative and can involve real time monitoring of the amplification reaction or conventional end-point monitoring.

In one embodiment, the invention provides for diagnostic assays that do not require post-amplification manipulations and minimise the amount of time required to conduct the assay. For example, in a specific embodiment, there is provided a diagnostic assay, utilising the primers and probes described herein, that can be completed using real time PCR technology in about 54 hours and generally in 24 hours or less.

Such diagnostic assays are particularly useful in the detection of contamination of various foodstuffs by *E. coli* O157:H7 and/or by *E. coli* O157:NM which produces verotoxin. Thus, in one embodiment, the present invention provides a rapid and sensitive diagnostic assay for the detection of contamination of a food sample by *E. coli* O157:H7 and/or by *E. coli* O157:NM which produces verotoxin. Foods that can be analysed using the diagnostic assays include, but are not limited to, dairy products such as milk, including raw milk, cheese, yoghurt, ice cream and cream; raw, cooked and cured meats and meat products, such as beef, pork, lamb, mutton, poultry (including turkey, chicken), game (including rabbit, grouse, pheasant, duck), minced and ground meat (including ground beef, ground turkey, ground chicken, ground pork); eggs; fruits and vegetables; nuts and nut products, such as nut butters; seafood products including fish and shellfish; and fruit or vegetable juices. The diagnostic assays may also be used to detect contamination of drinking water by *E. coli* O157:H7 and/or by *E. coli* O157:NM which produces verotoxin.

While the primary focus of detection is food products, the present invention also contemplates the use of the primers and probes in diagnostic assays for the detection of *E. coli* contamination of other biological samples, such as patient specimens in a clinical setting, for example, faeces, blood, saliva, throat swabs, urine, mucous, and the like, as well as *E. coli* contamination of surfaces and instruments, such as surgical or dental instruments. The diagnostic assays are also useful in the assessment of microbiologically pure cultures, and in environmental and pharmaceutical quality control processes.

The test sample can be used in the assay either directly (i.e. as obtained from the source) or following one or more pre-treatment steps to modify the character of the sample. Thus, the test sample can be pre-treated prior to use, for example, by disrupting cells or tissue, extracting the microbial content from the sample (such as a swab or wipe test sample), enhancing/enriching the microbial content of the sample by culturing in a suitable medium, preparing liquids from solid materials, diluting viscous fluids, filtering liquids, distilling liquids, concentrating liquids, inactivating interfering components, adding reagents, purifying nucleic acids, and the like. In one embodiment of the present invention, the test sample is subjected to one or more steps to isolate, or partially isolate, nucleic acids therefrom. In another embodiment of the invention, the test sample is subjected to an enrichment procedure to enhance the microbial content of the sample prior to use in the assay.

As indicated above, the polynucleotide primers and probes of the invention can be used in assays to quantitate the amount of a target nucleotide sequence in a test sample. Thus, the present invention provides for method to specifically amplify, detect and quantitate a target nucleotide sequence in a test sample, the methods generally comprising the steps of:

(a) forming a reaction mixture comprising a test sample, amplification reagents, one or more polynucleotide probes capable of specifically hybridising to a portion of a target nucleotide sequence and one or more polynucleotide primers corresponding to or complementary to a portion of a gnd gene from *E. coli* O157:H7 and/or *E. coli* O157:NM comprising said target nucleotide sequence;

(b) subjecting the mixture to amplification conditions to generate at least one copy of the target nucleotide sequence, or a nucleic acid sequence complementary to the target nucleotide sequence;

(c) hybridizing the probe to the target nucleotide sequence or the nucleic acid sequence complementary to the target sequence, so as to form a probe:target hybrid;

(d) detecting the probe:target hybrid; and (e) analysing the amount of probe:target hybrid present as an indication of the amount of target nucleotide sequence present in the test sample.

The steps of this method may also be varied and may employ combinations of primers and probes for different target sequences as described above for the amplification/detection method.

In one embodiment, the method employs one or more labelled polynucleotide probes in step (a) and steps (d) and (e) are as follows:

(d) detecting the probe:target hybrid by detecting the signal produced by the hybridized labelled probe; and (e) analysing the amount of signal produced as an indication of the amount of target nucleotide sequence present in the test sample.

Step (e) can be conducted, for example, by comparing the amount of signal produced to a standard or utilising one of a number of statistical methods known in the art that do not require a standard.

Various types of standards for quantitative assays are known in the art. For example, the standard can consist of a standard curve compiled by amplification and detection of known quantities of the target nucleotide sequence under the assay conditions. Alternatively, relative quantitation can be performed without the need for a standard curve (see, for example, Pfaffl, M W. (2001) *Nucleic Acids Research* 29(9): 2002-2007). In this method, a reference gene is selected against which the expression of the target gene can be compared and an additional pair of primers and an appropriate probe are included in the reaction in order to amplify and detect a portion of the selected reference gene. The reference gene is usually a gene that is expressed constitutively, for example, a house-keeping gene.

Another similar method of quantification is based on the inclusion of an internal standard in the reaction. Such internal standards generally comprise a control target nucleotide sequence and a control polynucleotide probe. The internal standard can further include an additional pair of primers that specifically amplify the control target nucleotide sequence and are unrelated to the polynucleotides of the present invention. Alternatively, the control target sequence can contain primer target sequences that allow specific binding of the assay primers but a different probe target sequence. This allows both the target sequence(s) and the control sequence to be amplified with the same primers, but the amplicons are detected with separate probe polynucleotides. Typically, when a reference gene or an internal standard is employed, the reference/control probe incorporates a detectable label that is distinct from the label incorporated into the target sequence specific probe(s). The signals generated by these labels when they bind their respective target sequences can thus be distinguished.

In the context of the present invention, a control target nucleotide sequence is a nucleic acid sequence that (i) can be amplified either by the target sequence specific primers or by control primers, (ii) specifically hybridizes to the control probe under the assay conditions and (iii) does not exhibit significant hybridization to the target sequence specific probe(s) under the same conditions. One skilled in the art will recognise that the actual nucleic acid sequences of the control target nucleotide and the control probe are not important provided that they both meet the criteria outlined above.

The diagnostic assays can be readily adapted for high-throughput. High-throughput assays provide the advantage of processing many samples simultaneously and significantly decrease the time required to screen a large number of samples. The present invention, therefore, contemplates the use of the polynucleotides of the present invention in high-throughput screening or assays to detect and/or quantitate target nucleotide sequences in a plurality of test samples.

For high-throughput assays, reaction components are usually housed in a multi-container carrier or platform, such as a multi-well microtitre plate, which allows a plurality of assays each containing a different test sample to be monitored simultaneously. Control samples can also be included in the plates to provide internal controls for each plate. Many automated systems are now available commercially for high-throughput assays, as are automation capabilities for procedures such as sample and reagent pipetting, liquid dispensing, timed incubations, formatting samples into microarrays, microplate thermocycling and microplate readings in an appropriate detector, resulting in much faster throughput times.

Kits and Packages for the Detection of *E. coli* O157:H7 and/or Detection of *E. coli* O157:NM which Produces Verotoxin The present invention further provides for kits for detecting *E. coli* O157: H7 and/or *E. coli* O157:NM verotoxin producers in a variety of samples. In general, the kits comprise one or more pairs of primers and one or more probe capable of amplifying and detecting target sequence(s) as described above. If desired, one of the primers and the probe may be provided in the form of a single polynucleotide, such as a Scorpion probe, as described above. The probe provided in the kit can be unlabelled, or can incorporate a detectable label, such as a fluorophore or a fluorophore and a quencher, or the kit may include reagents for labelling the probe. The primers/probes can be provided in separate containers or in an array format, for example, pre-dispensed into microtitre plates.

One embodiment of the present invention provides for kits comprising a combination of primers and probes that are capable of amplifying and detecting target sequences from *E. coli* O157: H7 target sequences and/or *E. coli* O157:NM which produces verotoxin associated with different genes.

The kits can optionally include amplification reagents, such as buffers, salts, enzymes, enzyme co-factors, nucleotides and the like. Other components, such as buffers and solutions for the enrichment, isolation and/or lysis of bacteria in a test sample, extraction of nucleic acids, purification of nucleic acids and the like may also be included in the kit. One or more of the components of the kit may be lyophilised and the kit may further comprise reagents suitable for the reconstitution of the lyophilised components.

The various components of the kit are provided in suitable containers. As indicated above, one or more of the containers may be a microtitre plate. Where appropriate, the kit may also optionally contain reaction vessels, mixing vessels and other components that facilitate the preparation of reagents or nucleic acids from the test sample.

The kit may additionally include one or more controls. For example, control polynucleotides (primers, probes, target sequences or a combination thereof) may be provided that allow for quality control of the amplification reaction and/or sample preparation, or that allow for the quantitation of the target nucleotide sequences.

The kit can additionally contain instructions for use, which may be provided in paper form or in computer-readable form, such as a disc, CD, DVD or the like.

The present invention further contemplates that the kits described above may be provided as part of a package that includes computer software to analyse data generated from the use of the kit.

The invention will now be described with reference to specific examples. It will be understood that the following examples are intended to describe preferred embodiments of the invention and are not intended to limit the invention in any way.

EXAMPLES

Example 1

Determination of a Unique, Conserved DNA Region in *E. coli* O157: H7 gnd Gene Sequences (#1)

The gnd gene coding regions from 17 different *E. coli* isolates were sequenced and aligned using the multiple alignment program Clustal W™. The resulting alignment was used to identify short DNA regions that were conserved within the *E. coli* O157: H7 group, yet which are excluded from other bacteria. FIG. 1 depicts a sample of such an alignment in which a portion of the gnd gene of 17 different *E. coli* strains have been aligned.

A 75 nucleotide conserved sequence (conserved sequence #1) was identified as described above (SEQ ID NO:19). This unique and conserved element of *E. coli* O157. H7 gnd-gene sequences was used to design highly specific primers for the PCR amplification of the conserved region of the gnd gene.

Example 2

Generation of PCR Primers for Amplification of the end Conserved Sequence #1

Within the conserved 75 nucleotide sequence identified as described in Example 1, regions that could serve as primer target sequences were identified. These primer target sequences were used to design primers to allow efficient PCR amplification. The primer sequences are shown below:

```
Forward primer #1:
5'- AGGAGGGCGCACTA -3'          [SEQ ID NO: 21]

Reverse primer #1:
5'- GGATCGGCGCAACT -3'          [SEQ ID NO: 22]

Forward primer #2:
5'- TGGTGAGGAGGGCGCACTA -3'     [SEQ ID NO: 27]

Reverse primer #2:
5'- GAATAGGCTTCAGCAATCAGC-3'    [SEQ ID NO: 28]
```

In the alignment presented in FIG. 1, the positions of forward primer #1 and the reverse primer #1 are represented by shaded boxes. Forward primer #1 starts at position 365 and ends at position 378 of the alignment. Reverse primer #1 represents the reverse complement of the region starting at position 426 and ending at position 439.

Example 3

Generation of Molecular Beacon Probes Specific for the *E. coli* O157:H7,end Conserved Sequence #1

In order to design molecular beacon probes specific for *E. coli* O157:H7, a region within the conserved sequence described above was identified which not only was highly conserved in all *E. coli*O157:H7 isolates but was also exclusive to *E. coli* O157:H7 isolates. This sequence consisted of a 21 nucleotide region that would be suitable for use as a molecular beacon target sequence. The sequence is provided below:

```
5'- CCTGGTGGGCAGAAAGAAGCC -3'   [SEQ ID NO: 20]
```

The complement of this sequence [SEQ ID NO:26] is also suitable for use as a molecular beacon target sequence.

A molecular beacon probe having the sequence shown below was synthesized by Integrated DNA Technologies Inc. molecular Beacon Probe #1:

```
5'- cCCTGGTGGGCAGAAAGAAGCCaggg -3'   [SEQ ID NO: 23]
```

The complement of this sequence (SEQ ID NO:25, shown below) can also be used as a molecular beacon probe for detecting *E. coli* O157:H7.

```
5'- ccctGGCTTCTTTCTGCCCACCAGGg-3'    [SEQ ID NO: 25]
```

The starting material for the synthesis of the molecular beacons was an oligonucleotide that contains a sulfhydryl group at its 5' end and a primary amino group at its 3' end. DABCYL was coupled to the primary amino group utilizing an amine-reactive derivative of DABCYL. The oligonucleotides that were coupled to DABCYL were then purified. The protective trityl moiety was then removed from the 5'-sulfhydryl group and a fluorophore was introduced in its place using an iodoacetamide derivative.

An individual skilled in the art would recognize that a variety of methodologies could be used for synthesis of the molecular beacons. For example, a controlled-pore glass column that introduces a DABCYL moiety at the 3' end of an oligonucleotide has recently become available, which enables the synthesis of a molecular beacon completely on a DNA synthesizer.

Table 2 provides a general overview of the characteristics of molecular beacon probe #1. The beacon sequence shown in Table 2 indicates the stem region in lower case and the loop region in upper case.

TABLE 2

| Description of gnd molecular beacon probe #1 |
|---|
| Beacon sequence (5'→ 3'):<br>cCCTGGTGGGCAGAAAGAAGCCaggg |
| Fluorophore (5'):<br>FAM |
| Quencher (3'):<br>DABCYL |

Table 3 provides an overview of the thermodynamics of the folding of molecular beacon probe #1. Calculations were made using MFOLD™ software, or the Oligo Analyzer software package available on Integrated DNA Technologies Inc. web site. FIG. 2 shows the arrangement of PCR primers and the molecular beacon probe in the gnd consensus sequence #1. Numbers in parentheses indicate the positions of the first and last nucleotides of each feature on the PCR product generated with the forward primer #1 and reverse primer #1.

TABLE 3

Thermodynamics of molecular beacon probe #1.

| | |
|---|---|
| Tm loop (thermodynamics algorithm) | 58.9° C. |
| Tm stem (mFOLD calculation) | 68.3° C. |
| $\Delta G_{37}$ (mFOLD calculation) | −4.0 kCal/mol |
| $\Delta H$ (mFOLD calculation) | −44.7 kCal/mol |

Example 4

Isolation of DNA from Test Samples

The following protocol was utilized in order to isolate DNA from test samples.
Material needed for DNA Extraction:
  Tungsten carbide beads: Qiagen
  Reagent DX: Qiagen
  DNeasy Plant Mini Kit: Qiagen
  Tissue Disruption equipment: Mixer Mill™ 300 (Qiagen)
The following method was followed:
1) Add to a 2 ml screw top tube: 1 tungsten carbide bead and 0.1 g glass beads 212 to 300 μm in width+sample to be analysed+500 μL of API buffer+1 μL of Reagent DX+1 μL of RNase A (100 mg/mL). Extraction control done without adding sample to be analysed.
2) Heat in Dry-Bath at 80° C. for 10 min.
3) Mix in a Mixer Mill 300 (MM300) at frequency of 30 Hz [1/s], 2 min.
4) Rotate tubes and let stand for 10 min at room temperature.
5) Mix in a Mixer Mill 300, frequency 30 Hz, 2 min.
6) Place tubes in boiling water for 5 min.
7) Centrifuge with a quick spin.
8) Add 150 μL of AP2 buffer.
9) Mix at frequency of 30 Hz for 30 sec. Rotate tubes and repeat.
10) Centrifuge at 13,000 rpm for 1 min.
11) Place tubes at −20° C. for 10 min.
12) Centrifuge at 13,000 rpm for 1 min.
13) Transfer supernatant in to a 2 mL screw top tube containing 850 μL of AP3/E buffer.
14) Mix by inverting, centrifuge with a quick spin.
15) Add 700 μL of mixture from step 13 to a DNeasy binding column and centrifuge at 800 rpm for 1 minute. Discard eluted buffer. Repeat process with leftover mixture from step 13.
16) Add 500 μL of wash buffer (AW buffer) to binding columns and centrifuge for 1 minute at 800 rpm. Discard eluted buffer.
17) Add 500 μL of wash buffer (AW buffer) to binding columns and centrifuge for 1 minute at 800 rpm. Discard eluted buffer.
18) Centrifuge column again at 8000 rpm for 1 min.
19) Place column in a sterile 2 mL tube and add 50 μL of AE elution buffer preheated at 80° C.
20) Incubate for 1 min. Centrifuge at max speed for 2 min. Elute twice with 50 μL; final volume should be 100 μL.
21) Keep elution for PCR amplification.
Time of manipulation: 3 hours. Proceed to prepare PCR reaction for real-time detection.

Example 5

Amplification of the and Target Sequence and Hybridization of Molecular Beacon Probe #1, in Real Time PCR amplification was undertaken using the conditions described in Tables 4 and 5 below. The intensity of fluorescence emitted by the fluorophore component of the molecular beacon was detected at the annealing stage of each amplification cycle. In Table 4, note that the PCR buffer contains 2.25 mM magnesium chloride (final concentration). Inclusion of additional magnesium chloride brings the final concentration to 4 mM in the reaction mixture.

TABLE 4

PCR mix used for validation.

| Reagent | Final concentration in reconstituted reaction |
|---|---|
| Qiagen PCR buffer, 10× | 1.5X |
| Forward primer #1, 25 μM | 0.5 μM |
| Reverse primer #1, 25 μM | 0.5 μM |
| dNTPs, 10 mM | 0.2 mM |
| $MgCl_2$, 25 mM | 1.75 mM |
| Molecular beacon #1, 10 μM | 0.3 μM |
| HotStarTaq, 5 U/μL | 1 U/25 μL reaction |

Table 5 presents an overview of the cycles used for each step of the PCR amplification.

TABLE 5

PCR program used throughout diagnostic test validation.

| Step | Temperature | Duration | Repeats |
|---|---|---|---|
| Initial polymerase activation | 95° C. | 15 min | 1 |
| Denaturation | 94° C. | 15 sec | 40 |
| Annealing | 55° C. | 15 sec | |
| Elongation | 72° C. | 15 sec | |

Fluorescence was detected in real-time using a fluorescence monitoring real-time PCR instrument, for example, a BioRad iCycler IQ™ or MJ Research Opticon™. Other instruments with similar fluorescent reading abilities can also be used.

Example 6

Positive Validation of end Primers and Molecular Beacon Probe #1

The effectiveness of gnd forward primer #1, reverse primer #1 and molecular beacon probe #1 for amplifying and detecting *E. coli* O157:H7 isolates was demonstrated as described generally below.
Genomic DNA from 62 strains of *E. coli* O157:H7 was isolated and amplified as described in the preceding Examples (4 and 5). The molecular beacon probe #1 was capable of detecting all *E. coli* O157:H7 isolated tested under these conditions. (i.e. sensitivity of 100%).

TABLE 6

Positive validation of gnd molecular beacon probe #1, forward primer #1 and reverse primer #1.

| Genus | Species | ID | Serovar | Results |
|---|---|---|---|---|
| Escherichia | coli | B71 | O157:H7 | + |
| Escherichia | coli | B73 | O157:H7 | + |
| Escherichia | coli | B74 | O157:H7 | + |
| Escherichia | coli | B75 | O157:H7 | + |
| Escherichia | coli | B76 | O157:H7 | + |
| Escherichia | coli | B81 | O157:H7 | + |
| Escherichia | coli | B82 | O157:H7 | + |
| Escherichia | coli | B83 | O157:H7 | + |
| Escherichia | coli | B84 | O157:H7 | + |
| Escherichia | coli | B85 | O157:H7 | + |
| Escherichia | coli | B86 | O157:H7 | + |
| Escherichia | coli | B87 | O157:H7 | + |
| Escherichia | coli | B88 | O157:H7 | + |
| Escherichia | coli | B89 | O157:H7 | + |
| Escherichia | coli | B90 | O157:H7 | + |
| Escherichia | coli | B91 | O157:H7 | + |
| Escherichia | coli | B92 | O157:H7 | + |
| Escherichia | coli | B93 | O157:H7 | + |
| Escherichia | coli | B94 | O157:H7 | + |
| Escherichia | coli | B95 | O157:H7 | + |
| Escherichia | coli | B96 | O157:H7 | + |
| Escherichia | coli | B97 | O157:H7 | + |
| Escherichia | coli | B163 | O157:H7 | + |
| Escherichia | coli | B164 | O157:NM | + |
| Escherichia | coli | B245 | O157:H7 | + |
| Escherichia | coli | B246 | O157:H7 | + |
| Escherichia | coli | B247 | O157:H7 | + |
| Escherichia | coli | B248 | O157:H7 | + |
| Escherichia | coli | B249 | O157:H7 | + |
| Escherichia | coli | B250 | O157:H7 | + |
| Escherichia | coli | B251 | O157:H7 | + |
| Escherichia | coli | B252 | O157:H7 | + |
| Escherichia | coli | B253 | O157:H7 | + |
| Escherichia | coli | B254 | O157:H7 | + |
| Escherichia | coli | B255 | O157:H7 | + |
| Escherichia | coli | B256 | O157:H7 | + |
| Escherichia | coli | B257 | O157:H7 | + |
| Escherichia | coli | B258 | O157:H7 | + |
| Escherichia | coli | B259 | O157:H7 | + |
| Escherichia | coli | B260 | O157:H7 | + |
| Escherichia | coli | B261 | O157:H7 | + |
| Escherichia | coli | B262 | O157:H7 | + |
| Escherichia | coli | B263 | O157:H7 | + |
| Escherichia | coli | B264 | O157:H7 | + |
| Escherichia | coli | B265 | O157:H7 | + |
| Escherichia | coli | B266 | O157:H7 | + |
| Escherichia | coli | B267 | O157:H7 | + |
| Escherichia | coli | B268 | O157:H7 | + |
| Escherichia | coli | B269 | O157:H7 | + |
| Escherichia | coli | B270 | O157:H7 | + |
| Escherichia | coli | B271 | O157:H7 | + |
| Escherichia | coli | B272 | O157:H7 | + |
| Escherichia | coli | B273 | O157: | + |
| Escherichia | coli | B274 | O157:NM | + |
| Escherichia | coli | B281 | O157:NM | + |
| Escherichia | coli | B282 | O157:NM | + |
| Escherichia | coli | B283 | O157:NM | + |
| Escherichia | coli | B284 | O157:NM | + |
| Escherichia | coli | B285 | O157:NM | + |
| Escherichia | coli | B288 | O157:NM | + |
| Escherichia | coli | B289 | O157:NM | + |
| Escherichia | coli | B290 | O157:NM | + |

Note:
the strains E. coli B164 and E. coli B273 to B290 are enterohaemorragic variants of the E. coli O157:H7 strains that are verotoxin-producers. Information obtained from Health Canada.

Example 7

Negative Validation of the Primers and Molecular Beacon #1

In order to test the ability of the primer set #1 and molecular beacon probe #1 to preferentially amplify and detect only E. coli O157:H7, a number of bacteria from species other than E. coli O157:H7 were tested as generally described below.

Samples of genomic DNA from the bacteria presented in Table 7 below were isolated and amplified using forward primer #1 and reverse primer #1 as described in the preceding Examples (4 and 5). When no probe was included in the amplification reaction, any amplicons produced were detected using SYBR® Green (see table 14 for the amplification mixture). Four E. coli not O157:H7 false positive were obtained during the amplification with primers only (i.e. specificity of 98%). Three out of these 4 false positive are not detected when the molecular beacon #1 is added.

Also included in additional rounds of tests was molecular beacon probe # 1. The above results suggest that both the amplification primers and the molecular beacon probe #1 are specific for E. coli O157:H7. One strain out of a total of 453 yielded an amplification product under these conditions. (One E. coli O1:H32 strain gave a positive signal under these conditions i.e. specificity of 99.8%).

TABLE 7

Negative Validation of the molecular beacon probe #1, forward primer #1 and reverse primer #1.

| Genus | Species | ID | Serovar | Result |
|---|---|---|---|---|
| Acinetobacter | calcoaceticus | B01 | | − |
| Acinetobacter | calcoaceticus | B08 | | − |
| Acinetobacter | lwoffi | B02 | | − |
| Aeromonas | hydrophila | B03 | | − |
| Aeromonas | hydrophila | B04 | | − |
| Aeromonas | salmonicida | B02 | | − |
| Aeromonas | salmonicida | B05 | | − |
| Alcaligenes | faecalis | B01 | | − |
| Bacillus | amyloliquefaciens | B01 | | − |
| Bacillus | amyloliquefaciens | B02 | | − |
| Bacillus | cereus | B01 | | − |
| Bacillus | cereus | B06 | | − |
| Bacillus | circulans | B04 | | − |
| Bacillus | circulans | B05 | | − |
| Bacillus | coagulans | B02 | | − |
| Bacillus | coagulans | B03 | | − |

TABLE 7-continued

Negative Validation of the molecular beacon probe #1, forward primer #1 and reverse primer #1.

| Genus | Species | ID | Serovar | Result |
|---|---|---|---|---|
| Bacillus | firmus | B01 | | − |
| Bacillus | Lentus | B01 | | − |
| Bacillus | licheniformis | B01 | | − |
| Bacillus | licheniformis | B02 | | − |
| Bacillus | megaterium | B06 | | − |
| Bacillus | megaterium | B07 | | − |
| Bacillus | mycoides | B01 | | − |
| Bacillus | pumilus | B04 | | − |
| Bacillus | pumilus | B06 | | − |
| Bacillus | sphaericus | B01 | | − |
| Bacillus | stearothermophilus | B03 | | − |
| Bacillus | subtilis | B04 | | − |
| Bacillus | subtilis | B09 | | − |
| Bacillus | thuringiensis | B01 | | − |
| Bacillus | thuringiensis | B03 | | − |
| Bacteroides | fragilis | B01 | | − |
| Bifidobacterium | adolescentis | B01 | | − |
| Bifidobacterium | animalis | B01 | | − |
| Bifidobacterium | bifidum | B01 | | − |
| Bifidobacterium | longum | B01 | | − |
| Bifidobacterium | pseudolongum | B01 | | − |
| Bifidobacterium | sp. | B17 | | − |
| Bifidobacterium | sp. | B25 | | − |
| Bifidobacterium | suis | B01 | | − |
| Bifidobacterium | thermophilus | B01 | | − |
| Bordetella | bronchiseptica | B01 | | − |
| Bordetella | pertussis | B01 | | − |
| Borrelia | burgdorferi | B01 | | − |
| Branhamella | catarrhalis | B01 | | − |
| Brevibacillus | laterosporus | B01 | | − |
| Burkholderia | cepacia | B01 | | − |
| Burkholderia | cepacia | B04 | | − |
| Campylobacter | coli | B01 | | − |
| Campylobacter | jejuni | B01 | | − |
| Campylobacter | jejuni | B02 | | − |
| Campylobacter | lari | B01 | | − |
| Campylobacter | lari | B02 | | − |
| Campylobacter | rectus | B01 | | − |
| Cellilomonea | sp. | B01 | | − |
| Chromobacterium | violaceum | B01 | | − |
| Chryseobacterium | sp. | B01 | | − |
| Chryseomonas | luteola | B02 | | − |
| Citrobacter | amalonaticus | B01 | | − |
| Citrobacter | amalonaticus | B02 | | − |
| Citrobacter | diversus | B01 | | − |
| Citrobacter | freundii | B03 | | − |
| Citrobacter | freundii | B09 | | − |
| Citrobacter | freundii | B10 | | − |
| Citrobacter | Koseri | B03 | | − |
| Citrobacter | werkmanii | B01 | | − |
| Clostridium | botulinum | B01 | | − |
| Clostridium | botulinum | B12 | | − |
| Clostridium | butyricum | B01 | | − |
| Clostridium | difficile | B TABLE 7-continued Negative Validation of the molecular beacon probe #1, forward primer #1 and reverse primer #1.

| Genus | Species | ID | Serovar | Result |
|---|---|---|---|---|
| Escherichia | coli | B01 | | − |
| Escherichia | coli | B12 | | − |
| Escherichia | coli | B13 | O18AC:NM | − |
| Escherichia | coli | B14 | O1:NM | − |
| Escherichia | coli | B15 | O75:H5 | − |
| Escherichia | coli | B16 | O62:H32 | − |
| Escherichia | coli | B17 | O71:H12 | − |
| Escherichia | coli | B18 | O55:NM | − |
| Escherichia | coli | B19 | O50:H4 | − |
| Escherichia | coli | B20 | O44:H18 | − |
| Escherichia | coli | B21 | O45:H23 | − |
| Escherichia | coli | B23 | O28:NM | − |
| Escherichia | coli | B24 | O34:NM | − |
| Escherichia | coli | B25 | O26:NM | − |
| Escherichia | coli | B26 | O24:NM | − |
| Escherichia | coli | B27 | O78:H11 | − |
| Escherichia | coli | B28 | O8:H9 | − |
| Escherichia | coli | B29 | O114:H32 | − |
| Escherichia | coli | B30 | O3:H44 | − |
| Escherichia | coli | B31 | O4:H5 | − |
| Escherichia | coli | B32 | O5:H4 | − |
| Escherichia | coli | B33 | O23:H15 | − |
| Escherichia | coli | B34 | O7:NM | − |
| Escherichia | coli | B35 | O18:H14 | − |
| Escherichia | coli | B36 | O9:H12 | − |
| Escherichia | coli | B37 | O10:NM | − |
| Escherichia | coli | B38 | O12:NM | − |
| Escherichia | coli | B39 | O13:NM | − |
| Escherichia | coli | B40 | O14:NM | − |
| Escherichia | coli | B41 | O78:NM | − |
| Escherichia | coli | B42 | O6:H49 | − |
| Escherichia | coli | B43 | O127:NM | − |
| Escherichia | coli | B44 | | − |
| Escherichia | coli | B45 | | − |
| Escherichia | coli | B46 | O1:H7 | − |
| Escherichia | coli | B47 | O157:H19 | − |
| Escherichia | coli | B48 | O86:NM | − |
| Escherichia | coli | B49 | O86:NM | − |
| Escherichia | coli | B50 | O40:H(NT) | − |
| Escherichia | coli | B51 | O18:H14 | − |
| Escherichia | coli | B52 | O136:NM | − |
| Escherichia | coli | B53 | O77:NM | − |
| Escherichia | coli | B54 | O113:H21 | − |
| Escherichia | coli | B55 | O80:H26 | − |
| Escherichia | coli | B56 | O102:H40 | − |
| Escherichia | coli | B57 | O86:NM | − |
| Escherichia | coli | B58 | | − |
| Escherichia | coli | B59 | O112:H18 | − |
| Escherichia | coli | B60 | O128AC:NM | − |
| Escherichia | coli | B61 | O112AC:NM | − |
| Escherichia | coli | B62 | O128AB:H2 | − |
| Escherichia | coli | B63 | O117:H4 | − |
| Escherichia | coli | B64 | O119:H18 | − |
| Escherichia | coli | B65 | O124:H25 | − |
| Escherichia | coli | B66 | O125AB:H19 | − |
| Escherichia | coli | B67 | O126:H2 | − |
| Escherichia | coli | B68 | O128AB:H8 | − |
| Escherichia | coli | B69 | B | − |
| Escherichia | coli | B77 | O6:H1 | − |
| Escherichia | coli | B78 | | − |
| Escherichia | coli | B79 | | − |
| Escherichia | coli | B80 | | − |
| Escherichia | coli | B98 | O157:H43 | − |
| Escherichia | coli | B99 | O157:H43 | − |
| Escherichia | coli | B100 | O157:H43 | − |
| Escherichia | coli | B101 | O157:NMb | − |
| Escherichia | coli | B102 | O157:NMb | − |
| Escherichia | coli | B103 | O55:H6 | − |
| Escherichia | coli | B104 | O55:H6 | − |
| Escherichia | coli | B105 | O55:H6 | − |
| Escherichia | coli | B106 | O55:H6 | − |
| Escherichia | coli | B107 | O55:H6 | − |
| Escherichia | coli | B108 | O55:H6 | − |
| Escherichia | coli | B109 | O55:NM | − |
| Escherichia | coli | B110 | O55:H6 | − |

TABLE 7-continued

Negative Validation of the molecular beacon probe #1, forward primer #1 and reverse primer #1.

| Genus | Species | ID | Serovar | Result |
|---|---|---|---|---|
| Escherichia | coli | B111 | O55:H6 | − |
| Escherichia | coli | B112 | O55:H6 | − |
| Escherichia | coli | B113 | O55:H5 | − |
| Escherichia | coli | B114 | O55:H7 | − |
| Escherichia | coli | B115 | O55:H7 | − |
| Escherichia | coli | B116 | O55:H7 | − |
| Escherichia | coli | B117 | O55:H7 | − |
| Escherichia | coli | B118 | O111:H21 | − |
| Escherichia | coli | B120 | O111:H12 | − |
| Escherichia | coli | B121 | O111:H12 | − |
| Escherichia | coli | B122 | O111:NM | − |
| Escherichia | coli | B123 | O111A:HNM | − |
| Escherichia | coli | B124 | O111:H8 | − |
| Escherichia | coli | B125 | O111:HNM | − |
| Escherichia | coli | B126 | O111:H11 | − |
| Escherichia | coli | B127 | O111:H8 | − |
| Escherichia | coli | B128 | O26:H11 | − |
| Escherichia | coli | B130 | O111:H12 | − |
| Escherichia | coli | B131 | O26:H11 | − |
| Escherichia | coli | B132 | O26:H11 | − |
| Escherichia | coli | B133 | O26:H11 | − |
| Escherichia | coli | B134 | O26:H11 | − |
| Escherichia | coli | B135 | O26:H11 | − |
| Escherichia | coli | B136 | O26:H11 | − |
| Escherichia | coli | B137 | O26:H11 | − |
| Escherichia | coli | B138 | O128A:H2 | − |
| Escherichia | coli | B139 | O128A:H2 | − |
| Escherichia | coli | B140 | O45:H2 | − |
| Escherichia | coli | B141 | O128:H2 | − |
| Escherichia | coli | B142 | O128:H2 | − |
| Escherichia | coli | B143 | O111:H2 | − |
| Escherichia | coli | B144 | O111:H2 | − |
| Escherichia | coli | B145 | O111:NM | − |
| Escherichia | coli | B146 | O111:H2 | − |
| Escherichia | coli | B147 | O111:HN | − |
| Escherichia | coli | B148 | O128:H7 | − |
| Escherichia | coli | B149 | O128:H7 | − |
| Escherichia | coli | B150 | O128:H7 | − |
| Escherichia | coli | B151 | O128:H7 | − |
| Escherichia | coli | B152 | O128:H47 | − |
| Escherichia | coli | B153 | O128:H21 | − |
| Escherichia | coli | B154 | O128:H21 | − |
| Escherichia | coli | B155 | O128A:H21 | − |
| Escherichia | coli | B156 | O128:HNM | − |
| Escherichia | coli | B157 | O128:H21 | − |
| Escherichia | coli | B158 | O111:H21 | − |
| Escherichia | coli | B159 | O111:H21 | − |
| Escherichia | coli | B160 | O111:H21 | − |
| Escherichia | coli | B161 | O111:H21 | − |
| Escherichia | coli | B162 | O111:H21 | − |
| Escherichia | coli | B165 | O15:NM | − |
| Escherichia | coli | B166 | ON:HN | − |
| Escherichia | coli | B167 | ON:H32 | − |
| Escherichia | coli | B168 | O1:H32 | + |
| Escherichia | coli | B169 | ON:HN | − |
| Escherichia | coli | B170 | O79:NM | − |
| Escherichia | coli | B171 | ON:NM | − |
| Escherichia | coli | B172 | O85:HN | − |
| Escherichia | coli | B174 | ON:NM | − |
| Escherichia | coli | B175 | O6:H10 | − |
| Escherichia | coli | B176 | O6:H10 | − |
| Escherichia | coli | B178 | ON:HN | − |
| Escherichia | coli | B179 | OM:HN | − |
| Escherichia | coli | B180 | O25:NM | − |
| Escherichia | coli | B181 | ON:H10 | − |
| Escherichia | coli | B182 | O106:NM | − |
| Escherichia | coli | B183 | O5:NM | − |
| Escherichia | coli | B184 | O5:HN | − |
| Escherichia | coli | B185 | O89:HN | − |
| Escherichia | coli | B186 | O121:HN | − |
| Escherichia | coli | B187 | ON:HN | − |
| Escherichia | coli | B188 | O86:H43 | − |
| Escherichia | coli | B189 | O15:NM | − |
| Escherichia | coli | B190 | ON:HN | − |
| Escherichia | coli | B191 | O104:H21 | − |

TABLE 7-continued

Negative Validation of the molecular beacon probe #1, forward primer #1 and reverse primer #1.

| Genus | Species | ID | Serovar | Result |
|---|---|---|---|---|
| *Escherichia* | *coli* | B192 | O104:NM | – |
| *Escherichia* | *coli* | B193 | O104:NM | – |
| *Escherichia* | *coli* | B194 | O150:H21 | – |
| *Escherichia* | *coli* | B195 | O113:H21 | – |
| *Escherichia* | *coli* | B196 | O79:H43 | – |
| *Escherichia* | *coli* | B197 | O7:H21 | – |
| *Escherichia* | *coli* | B198 | O7:H21 | – |
| *Escherichia* | *coli* | B199 | O88:NM | – |
| *Escherichia* | *coli* | B200 | O1:NM | – |
| *Escherichia* | *coli* | B201 | O79:H25 | – |
| *Escherichia* | *coli* | B202 | ON:HN | – |
| *Escherichia* | *coli* | B203 | O7:NM | – |
| *Escherichia* | *coli* | B204 | O7:NM | – |
| *Escherichia* | *coli* | B205 | O7:NM | – |
| *Escherichia* | *coli* | B206 | O7:NM | – |
| *Escherichia* | *coli* | B207 | ON:H26 | – |
| *Escherichia* | *coli* | B208 | ON:HN | – |
| *Escherichia* | *coli* | B209 | ON:HN | – |
| *Escherichia* | *coli* | B210 | ON:HN | – |
| *Escherichia* | *coli* | B211 | O1:H6 | – |
| *Escherichia* | *coli* | B212 | OM:H18 | – |
| *Escherichia* | *coli* | B213 | ON:HM | – |
| *Escherichia* | *coli* | B214 | O2:NM | – |
| *Escherichia* | *coli* | B215 | O2:HN | – |
| *Escherichia* | *coli* | B216 | O25:HN | – |
| *Escherichia* | *coli* | B217 | O25:H1 | – |
| *Escherichia* | *coli* | B218 | O4:HN | – |
| *Escherichia* | *coli* | B219 | O25:H1 | – |
| *Escherichia* | *coli* | B220 | O25:H2 | – |
| *Escherichia* | *coli* | B221 | O6:H1 | – |
| *Escherichia* | *coli* | B222 | ON:NM | – |
| *Escherichia* | *coli* | B223 | O112:H8 | – |
| *Escherichia* | *coli* | B224 | O4:H40 | – |
| *Escherichia* | *coli* | B225 | O4:HN | – |
| *Escherichia* | *coli* | B226 | O2:NM | – |
| *Escherichia* | *coli* | B227 | O2:NM | – |
| *Escherichia* | *coli* | B228 | O2:NM | – |
| *Escherichia* | *coli* | B229 | O75:NM | – |
| *Escherichia* | *coli* | B230 | ON:H10 | – |
| *Escherichia* | *coli* | B231 | O4:H40 | – |
| *Escherichia* | *coli* | B232 | O4:H43 | – |
| *Escherichia* | *coli* | B233 | ON:NM | – |
| *Escherichia* | *coli* | B234 | ON:NM | – |
| *Escherichia* | *coli* | B235 | O78:NM | – |
| *Escherichia* | *coli* | B236 | O78:NM | – |
| *Escherichia* | *coli* | B237 | O144:H8 | – |
| *Escherichia* | *coli* | B239 | O10:K5(1):H4 | – |
| *Escherichia* | *coli* | B240 | O119:K69(b14) | – |
| *Escherichia* | *coli* | B241 | O3:K2a,bb(1):H2 | – |
| *Escherichia* | *coli* | B242 | O127:K63(b8) | – |
| *Escherichia* | *coli* | B243 | O112a,112c:K66(b11):nm | – |
| *Escherichia* | *coli* | B244 | | – |
| *Escherichia* | *coli* | B275 | O55:H7 | – |
| *Escherichia* | *coli* | B276 | O55:NM | – |
| *Escherichia* | *coli* | B277 | O55:NM | – |
| *Escherichia* | *coli* | B278 | O55:H7 | – |
| *Escherichia* | *coli* | B279 | O55:H7 | – |
| *Escherichia* | *coli* | B280 | O55:H7 | – |
| *Escherichia* | *coli* | B286 | O157:NMb | – |
| *Escherichia* | *coli* | B287 | O157:NMb | – |
| *Escherichia* | *fergusonii* | B01 | | – |
| *Escherichia* | *hermannii* | B02 | | – |
| *Escherichia* | *hermannii* | B03 | | – |
| *Escherichia* | *vulneris* | B01 | | – |
| *Haemophilus* | *equigenitalis* | B01 | | – |
| *Haemophilus* | *influenzae* | B02 | | – |
| *Haemophilus* | *influenzae* | B04 | | – |
| *Haemophilus* | *paragallinarum* | B01 | | – |
| *Hafnia* | *alvei* | B01 | | – |
| *Hafnia* | *alvei* | B02 | | – |
| *Helicobacter* | *pylori* | B02 | | – |
| *Klebsiella* | *ornithinolytica* | B01 | | – |
| *Klebsiella* | *oxytoca* | B02 | | – |
| *Klebsiella* | *oxytoca* | B06 | | – |
| *Klebsiella* | *oxytoca* | B09 | | – |

TABLE 7-continued

Negative Validation of the molecular beacon probe #1, forward primer #1 and reverse primer #1.

| Genus | Species | ID | Serovar | Result |
|---|---|---|---|---|
| Klebsiella | planticola | B01 | | − |
| Klebsiella | planticola | B02 | | − |
| Klebsiella | pneumoniae | B08 | | − |
| Klebsiella | terrigena | B01 | | − |
| Kocuria | kristinae | B01 | | − |
| Kurthia | zopfii | B01 | | − |
| Kurthia | zopfii | B02 | | − |
| Lactobacillus | acidophilus | B01 | | − |
| Lactobacillus | casei | B01 | | − |
| Lactobacillus | casei | B03 | | − |
| Lactobacillus | delbreuckii | B01 | | − |
| Lactobacillus | delbreuckii | B03 | | − |
| Lactobacillus | helveticus | B01 | | − |
| Lactobacillus | pentosus | B01 | | − |
| Lactobacillus | plantarum | B01 | | − |
| Lactobacillus | plantarum | B03 | | − |
| Lactobacillus | rhamnosus | B02 | | − |
| Lactococcus | raffinolactis | B01 | | − |
| Lactococcus | lactis | B02 | | − |
| Lactococcus | lactis | B09 | | − |
| Listeria | grayi | B01 | | − |
| Listeria | innocua | B02 | | − |
| Listeria | innocua | B07 | | − |
| Listeria | innocua | B10 | | − |
| Listeria | ivanovii | B01 | | − |
| Listeria | ivanovii | B02 | | − |
| Listeria | monocytogenes | B14 | | − |
| Listeria | monocytogenes | B27 | | − |
| Listeria | seeligeri | B01 | | − |
| Listeria | welshimeri | B01 | | − |
| Micrococcus | luteus | B04 | | − |
| Moraxella | | B01 | | − |
| Mycobacterium | smegmatis | B01 | | − |
| Neisseria | gonorrhoeae | B01 | | − |
| Neisseria | lactamica | B01 | | − |
| Neisseria | meningitidis | B01 | | − |
| Neisseria | meningitidis | B02 | | − |
| Neisseria | sica | B02 | | − |
| Nocardia | asteroides | B01 | | − |
| Pediococcus | acidilactici | B01 | | − |
| Pediococcus | acidilactici | B02 | | − |
| Pediococcus | pentosaceus | B01 | | − |
| Proteus | mirabilis | B05 | | − |
| Proteus | mirabilis | B10 | | − |
| Proteus | penneri | B01 | | − |
| Proteus | penneri | B02 | | − |
| Proteus | vulgaris | B02 | | − |
| Proteus | vulgaris | B04 | | − |
| Pseudomonas | aeruginosa | B12 | | − |
| Pseudomonas | aeruginosa | B17 | | − |
| Pseudomonas | mendocina | B01 | | − |
| Pseudomonas | pseudoalcaligenes | B01 | | − |
| Pseudomonas | putida | B04 | | − |
| Pseudomonas | putida | B05 | | − |
| Pseudomonas | stutzeri | B02 | | − |
| Salmonella | agona | B01 | | − |
| Salmonella | arizonae | B01 | | − |
| Salmonella | arizonae | B04 | | − |
| Salmonella | bongori | B01 | | − |
| Salmonella | brandenburg | B01 | | − |
| Salmonella | choleraesuis | B02 | | − |
| Salmonella | choleraesuis | B04 | | − |
| Salmonella | diarizonae | B01 | | − |
| Salmonella | dublin | B02 | | − |
| Salmonella | dublin | B05 | | − |
| Salmonella | enteritidis | B03 | | − |
| Salmonella | enteritidis | B09 | | − |
| Salmonella | heidelberg | B01 | | − |
| Salmonella | heidelberg | B02 | | − |
| Salmonella | houtenae | B01 | | − |
| Salmonella | indica | B01 | | − |
| Salmonella | infantis | B01 | | − |
| Salmonella | infantis | B02 | | − |
| Salmonella | montevideo | B01 | | − |
| Salmonella | montevideo | B02 | | − |

TABLE 7-continued

Negative Validation of the molecular beacon probe #1, forward primer #1 and reverse primer #1.

| Genus | Species | ID | Serovar | Result |
|---|---|---|---|---|
| Salmonella | newport | B02 | | − |
| Salmonella | newport | B04 | | − |
| Salmonella | paratyphi | B03 | | − |
| Salmonella | paratyphi | B06 | | − |
| Salmonella | paratyphi | B11 | | − |
| Salmonella | paratyphi | B13 | | − |
| Salmonella | saintpaul | B04 | | − |
| Salmonella | saintpaul | B05 | | − |
| Salmonella | senftenberg | B01 | | − |
| Salmonella | stanley | B01 | | − |
| Salmonella | thompson | B01 | | − |
| Salmonella | thompson | B02 | | − |
| Salmonella | typhi | B03 | | − |
| Salmonella | typhi | B04 | | − |
| Salmonella | typhimurium | B04 | | − |
| Salmonella | typhimurium | B05 | | − |
| Salmonella | typhisuis | B01 | | − |
| Salmonella | typhisuis | B02 | | − |
| Serratia | liquefaciens | B01 | | − |
| Serratia | liquefaciens | B02 | | − |
| Serratia | marcescens | B04 | | − |
| Serratia | marcescens | B07 | | − |
| Serratia | odorifera | B01 | | − |
| Shigella | boydii | B01 | | − |
| Shigella | dysenteriae | B01 | | − |
| Shigella | dysenteriae | B02 | | − |
| Shigella | flexneri | B11 | | − |
| Shigella | flexneri | B15 | | − |
| Shigella | sonnei | B01 | | − |
| Shigella | sonnei | B04 | | − |
| Staphylococcus | aureus | B06 | | − |
| Staphylococcus | aureus | B09 | | − |
| Staphylococcus | chromogenes | B01 | | − |
| Staphylococcus | epidermidis | B03 | | − |
| Staphylococcus | epidermidis | B04 | | − |
| Staphylococcus | intermedius | B01 | | − |
| Staphylococcus | lentis | B01 | | − |
| Staphylococcus | ludgdunensis | B01 | | − |
| Staphylococcus | schieiferi | B01 | | − |
| Staphylococcus | xylosus | B01 | | − |
| Stenotrophomonas | maltophilia | B02 | | − |
| Streptococcus | agalactiae | B01 | | − |
| Streptococcus | agalactiae | B02 | | − |
| Streptococcus | bovis | B01 | | − |
| Streptococcus | pneumoniae | B01 | | − |
| Streptococcus | pneumoniae | B02 | | − |
| Streptococcus | pyogenes | B02 | | − |
| Streptococcus | pyogenes | B03 | | − |
| Streptococcus | suis | B01 | | − |
| Streptococcus | thermophilus | B02 | | − |
| Vibrio | alginolyticus | B01 | | − |
| Vibrio | cholerae | B07 | | − |
| Vibrio | cholerae | B11 | | − |
| Vibrio | cholerae | B31 | | − |
| Vibrio | fluvialis | B01 | | − |
| Vibrio | hollisae | B01 | | − |
| Vibrio | vulnificus | B01 | | − |
| Xanthomonas | campestris | B01 | | − |
| Yersinia | enterocolitica | B03 | | − |
| Yersinia | enterocolitica | B12 | | − |
| Yersinia | frederiksenii | B01 | | − |
| Yersinia | kritensenii | B01 | | − |

Example 8

Determination of a Unique, Conserved DNA Region in *E. coli* O157:H7, end Gene Sequences (#2)

Figure 4:
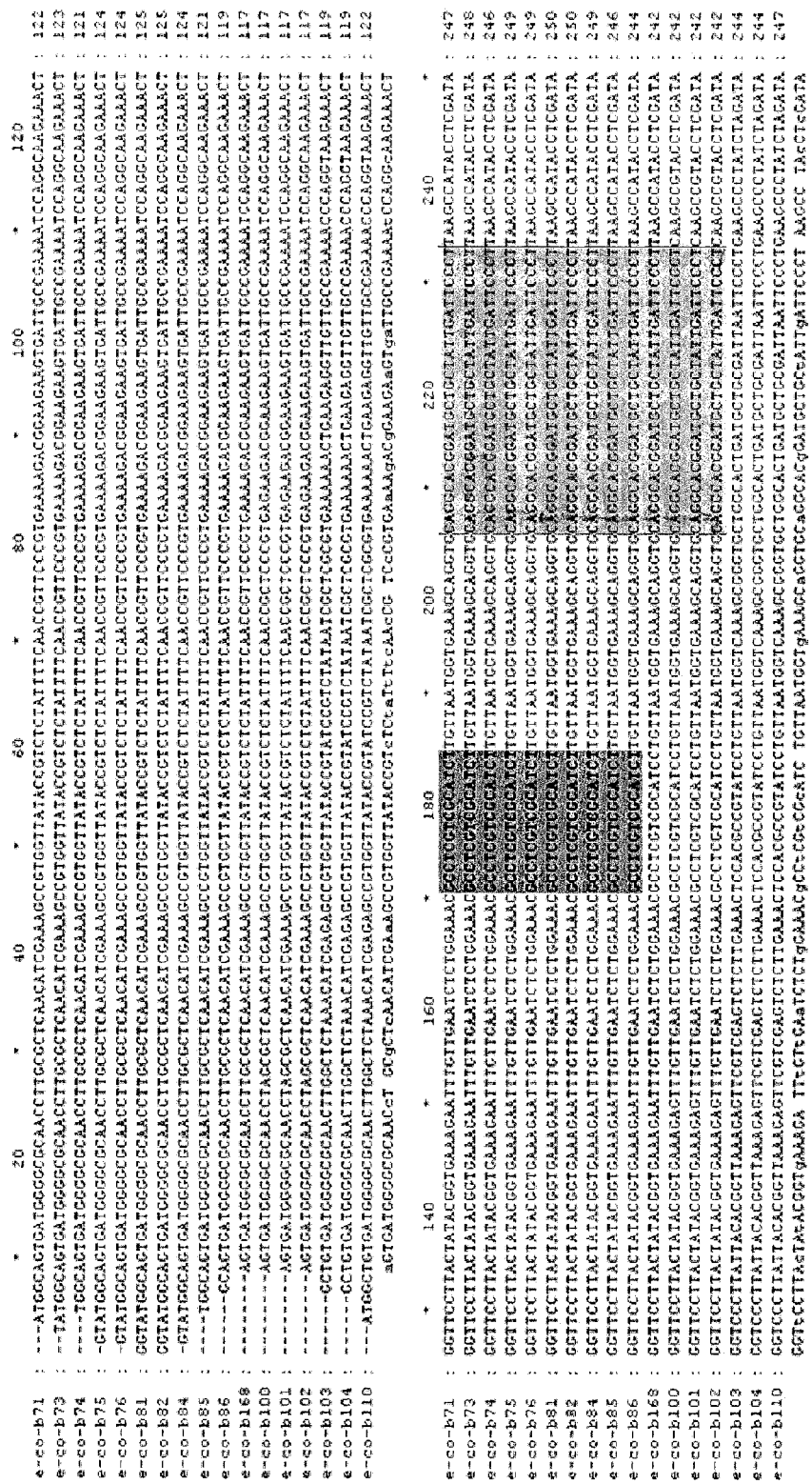
FIG. 4 presents a multiple sequence alignment showing conserved regions of a portion of the gnd gene from E. coli O157:H7 strains [SEQ ID NOs:2-11] and from various E. coli strains not O157:H7 [SEQ ID NOs:12-18] The sequences depicted represent the coding strand of the gene. Shaded blocks highlight the following regions: bases 171 to 184: forward primer #3 [SEQ ID NO:31]; bases 206 to 233: binding site for molecular beacon #2 [SEQ ID NO:34]; bases 365 to 378: reverse primer # 3 [SEQ ID NO:32]

The gnd gene coding regions from 17 different *E. coli* isolates were sequenced and aligned using the multiple alignment program Clustal W™. The resulting alignment was used to identify short DNA regions that were conserved within the *E. coli* O157: H7 group, yet which are excluded from other bacteria. FIG. 4 depicts a sample of such an alignment in which a portion of the gnd gene of 17 different *E. coli* strains have been aligned.

A 208 nucleotide conserved sequence (conserved sequence #2) was identified as described above (SEQ ID NO:29). This unique and conserved element of *E. coli* O157:

H7 gnd-gene sequences was used to design highly specific primers for the PCR amplification of the conserved region of the gnd gene.

Example 9

Generation of PCR Primers for Amplification of the end Conserved Sequence #2

Within the conserved 208 nucleotide sequence identified as described in Example 8, regions that could serve as primer target sequences were identified. These primer target sequences were used to design primers to allow efficient PCR amplification. The primer sequences are shown below:

```
Forward primer #3:
5'- GCCTCGTCGCATCT -3'         [SEQ ID NO: 31]

Reverse primer #3:
5'- TAGTGCGCCCTCCT -3'         [SEQ ID NO: 32]

Forward primer #4:
5'- GGAAACGCCTCGTCGCATCT -3'   [SEQ ID NO: 37]

Reverse primer #4:
5'- TAGTGCGCCCTCCTCACCA -3'    [SEQ ID NO: 38]
```

In the alignment presented in FIG. 4, the positions of forward primer #3 and the reverse primer #3 are represented by shaded boxes. Forward primer #3 starts at position 171 and ends at position 184 of the alignment. Reverse primer #3 represents the reverse complement of the region starting at position 365 and ending at position 378.

Example 10

Generation of Molecular Beacon Probes Specific for the E. coli O157:H7 Conserved Sequence #2

In order to design molecular beacon probes specific for E. coli O157:H7, a region within the conserved sequence described above was identified which not only was highly conserved in all E. coli O157:H7 isolates but was also exclusive to E. coli O157:H7 isolates. This sequence consisted of a 28 nucleotide region that would be suitable for use as a molecular beacon target sequence. The sequence is provided below:

```
5'- CAGGCACGGATGCTGCTATTGATTCCCT -3' [SEQ ID NO: 30]
```

The complement of this sequence [SEQ ID NO:36] is also suitable for use as a molecular beacon target sequence.

A molecular beacon probe having the sequence shown below was synthesized by Integrated DNA Technologies Inc. Molecular Beacon Probe #2:

```
                                            [SEQ ID NO: 33]
5'- ccCAGGCACGGATGCTGCTATTGATTCCCTggg -3'
```

The complement of this sequence (SEQ ID NO:35, shown below) can also be used as a molecular beacon probe for detecting E. coli O157:H7.

```
                                            [SEQ ID NO: 35]
5'- cccAGGGAATCAATAGCAGCATCCGTGCCTGgg-3'
```

The starting material for the synthesis of the molecular beacons was an oligonucleotide that contains a sulfhydryl group at its 5' end and a primary amino group at its 3' end. DABCYL was coupled to the primary amino group utilizing an amine-reactive derivative of DABCYL. The oligonucleotides that were coupled to DABCYL were then purified. The protective trityl moiety was then removed from the 5'-sulfhydryl group and a fluorophore was introduced in its place using an iodoacetamide derivative.

An individual skilled in the art would recognize that a variety of methodologies could be used for synthesis of the molecular beacons. For example, a controlled-pore glass column that introduces a DABCYL moiety at the 3' end of an oligonucleotide has recently become available, which enables the synthesis of a molecular beacon completely on a DNA synthesizer.

Table 8 provides a general overview of the characteristics of molecular beacon probe #2. The beacon sequence shown in Table 8 indicates the stem region in lower case and the loop region in upper case.

TABLE 8

Description of gnd molecular beacon probe #2

Beacon sequence (5'→ 3'):
ccCAGGCACGGATGCTGCTATTGATTCCCTggg

Fluorophore (5'):
FAM

Quencher (3'):
DABCYL

Figure 5:
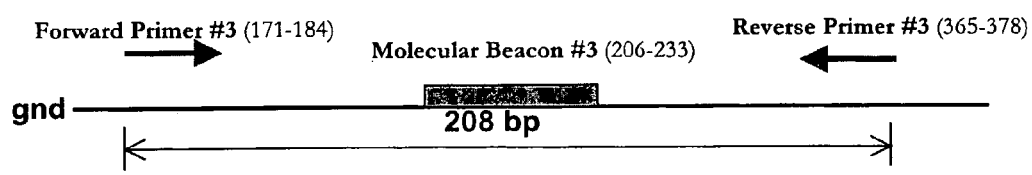
FIG. 5 presents the arrangement of PCR primers and a molecular beacon probe on a gnd conserved sequence #2 in one embodiment of the invention. Numbers in parentheses indicate the positions of the first and last nucleotides of each feature on the PCR product generated with primers SEQ ID NOs:31 & 32

Table 9 provides an overview of the thermodynamics of the folding of molecular beacon probe #2. Calculations were made using MFOLD™ software, or the Oligo Analyzer software package available on Integrated DNA Technologies Inc. web site. FIG. 5 shows the arrangement of PCR primers and the molecular beacon probe in the gnd consensus sequence #2. Numbers in parentheses indicate the positions of the first and last nucleotides of each feature on the PCR product generated with the forward primer #3 and reverse primer #3.

TABLE 9

Thermodynamics of molecular beacon probe #2.

| | |
|---|---|
| Tm loop (thermodynamics algorithm) | 69.8° C. |
| Tm stem (mFOLD calculation) | 60.5° C. |
| $\Delta G_{37}$ (mFOLD calculation) | −3.0 kCal/mol |
| $\Delta H$ (mFOLD calculation) | −42.8 kCal/mol |

A further gnd specific molecular beacon suitable for the detection of E. coli O157:H7 was also prepared as described above. The sequence is shown below (nucleotides in lower case represent the nucleotides that make up the stem of the beacon):

Molecular Beacon Probe #3:

```
5'- cgtCCTTAAGCCATACCTCGATAAggacg-3' [SEQ ID NO: 39]
```

The complement of this sequence (SEQ ID NO:41, see below) can also be used as a molecular beacon probe for the detection of E. coli O157:H7.

```
5'- cgtccTTATCGAGGTATGGCTTAAGGacg-3' [SEQ ID NO: 41]
```

Example 11

Positive Validation of Primer Pair #3 and Molecular Beacon Probe #2

The effectiveness of forward primer #3, reverse primer #3 and molecular beacon probe #2 for amplifying and detecting *E. coli* isolates was demonstrated as described generally below.

Genomic DNA from the species and strains presented in Table 11 below was isolated as described in Example 4. Amplification was conducted as described in Example 5 with the exception that forward primer #3 and reverse primer #3 and the following PCR mix were used.

TABLE 10

PCR mix used for validation.

| Reagent | Final concentration in reconstituted reaction |
|---|---|
| Qiagen PCR buffer, 10X | 1.5X |
| Forward primer #3, 25 μM | 0.5 μM |
| Reverse primer #3, 25 μM | 0.5 μM |
| dNTPs, 10 mM | 0.2 mM |
| MgCl$_2$, 25 mM | 1.75 mM |
| Molecular beacon #2, 10 μM | 0.3 μM |
| HotStarTaq, 5 U/μL | 1 U/25 μL reaction |

Results are presented in Table 11 and indicate that of the 27 strains of *E. coli* O157:H7 tested, 27 gave a positive signal (i.e. sensitivity of 100%).

TABLE 11

Positive validation of gnd molecular beacon #3 and primers.

| Genus | Species | ID | Serovar | Result |
|---|---|---|---|---|
| Escherichia | coli | B71 | O157:H7 | + |
| Escherichia | coli | B73 | O157:H7 | + |
| Escherichia | coli | B74 | O157:H7 | + |
| Escherichia | coli | B75 | O157:H7 | + |
| Escherichia | coli | B76 | O157:H7 | + |
| Escherichia | coli | B81 | O157:H7 | + |
| Escherichia | coli | B82 | O157:H7 | + |
| Escherichia | coli | B83 | O157:H7 | + |
| Escherichia | coli | B84 | O157:H7 | + |
| Escherichia | coli | B85 | O157:H7 | + |
| Escherichia | coli | B86 | O157:H7 | + |
| Escherichia | coli | B87 | O157:H7 | + |
| Escherichia | coli | B88 | O157:H7 | + |
| Escherichia | coli | B89 | O157:H7 | + |
| Escherichia | coli | B90 | O157:H7 | + |
| Escherichia | coli | B91 | O157:H7 | + |
| Escherichia | coli | B92 | O157:H7 | + |
| Escherichia | coli | B93 | O157:H7 | + |
| Escherichia | coli | B94 | O157:H7 | + |
| Escherichia | coli | B95 | O157:H7 | + |
| Escherichia | coli | B96 | O157:H7 | + |
| Escherichia | coli | B97 | O157:H7 | + |
| Escherichia | coli | B163 | O157:H7 | + |
| Escherichia | coli | B164 | O157:Hnm (VT+) | + |
| Escherichia | coli | B245 | O157:H7 | + |
| Escherichia | coli | B246 | O157:H7 | + |
| Escherichia | coli | B247 | O157:H7 | + |

Example 12

Negative Validation of the Primer Pair #3 and Molecular Beacon #3

In order to test the ability of forward primer #3, reverse primer #3 and molecular beacon #3 to preferentially amplify and detect only *E. coli* O157:H7, a number of bacteria other than *E. coli* O157:H7 were tested.

Samples of genomic DNA from the bacteria presented in Table 12 below were isolated and amplified as described in the preceding Example. When no probe was included in the amplification reaction, any amplicons produced were detected using SYBR® Green (see table 14 for the amplification mixture). Two amplification products were observed (i.e. specificity of 99%). One of these false positive is not detected when the molecular beacon probe #3 is added in the amplification reaction.

The Forward primer #4 and the reverse primer #4 were also tested to detect, using SYBR® Green, amplicons of a panel of 202 *E. coli* strains with different serotypes. Only specificity of 44% is achieved with the forward primer #4 and the reverse primer #4.

Also included in additional rounds of tests was molecular beacon #3. A panel of 202 *E. coli* strains was tested and only one *E. coli* O1:H32 was detected as positive. (i.e. specificity of 99.5%).

In Table 12, None of the tested strains provided a positive result. These results suggest that both the amplification primers and the molecular beacon #3 are highly specific for *E. coli*.

TABLE 12

Negative Validation of the gnd Primers and Molecular Beacon #3

| Genus | Species | ID | Serovar | Results |
|---|---|---|---|---|
| Escherichia | coli | B01 | | − |
| Escherichia | coli | B12 | | − |
| Escherichia | coli | B13 | O18AC:NM | − |
| Escherichia | coli | B14 | O1:NM | − |
| Escherichia | coli | B15 | O75:H5 | − |
| Escherichia | coli | B16 | O62:H32 | − |
| Escherichia | coli | B17 | O71:H12 | − |
| Escherichia | coli | B18 | O55:NM | − |
| Escherichia | coli | B19 | O50:H4 | − |
| Escherichia | coli | B20 | O44:H18 | − |
| Escherichia | coli | B21 | O45:H23 | − |
| Escherichia | coli | B23 | O28:NM | − |
| Escherichia | coli | B24 | O34:NM | − |
| Escherichia | coli | B25 | O26:NM | − |
| Escherichia | coli | B26 | O24:NM | − |
| Escherichia | coli | B27 | O78:H11 | − |
| Escherichia | coli | B28 | O8:H9 | − |
| Escherichia | coli | B29 | O114:H32 | − |
| Escherichia | coli | B30 | O3:H44 | − |
| Escherichia | coli | B31 | O4:H5 | − |
| Escherichia | coli | B32 | O5:H4 | − |
| Escherichia | coli | B33 | O23:H15 | − |
| Escherichia | coli | B34 | O7:NM | − |
| Escherichia | coli | B35 | O18:H14 | − |
| Escherichia | coli | B36 | O9:H12 | − |
| Escherichia | coli | B37 | O10:NM | − |
| Escherichia | coli | B38 | O12:NM | − |
| Escherichia | coli | B39 | O13:NM | − |
| Escherichia | coli | B40 | O14:NM | − |
| Escherichia | coli | B41 | O78:NM | − |
| Escherichia | coli | B42 | O6:H49 | − |
| Escherichia | coli | B43 | O127:NM | − |
| Escherichia | coli | B44 | | − |
| Escherichia | coli | B45 | | − |
| Escherichia | coli | B46 | O1:H7 | − |
| Escherichia | coli | B47 | O157:H19 | − |
| Escherichia | coli | B48 | O86:NM | − |
| Escherichia | coli | B49 | O86:NM | − |
| Escherichia | coli | B50 | O40:H(NT) | − |
| Escherichia | coli | B51 | O18:H14 | − |
| Escherichia | coli | B52 | O136:NM | − |
| Escherichia | coli | B53 | O77:NM | − |
| Escherichia | coli | B54 | O113:H21 | − |
| Escherichia | coli | B55 | O80:H26 | − |
| Escherichia | coli | B56 | O102:H40 | − |
| Escherichia | coli | B57 | O86:NM | − |

TABLE 12-continued

Negative Validation of the gnd Primers and Molecular Beacon #3

| Genus | Species | ID | Serovar | Results |
|---|---|---|---|---|
| Escherichia | coli | B58 | | − |
| Escherichia | coli | B59 | O112:H18 | − |
| Escherichia | coli | B60 | O128AC:NM | − |
| Escherichia | coli | B61 | O112AC:NM | − |
| Escherichia | coli | B62 | O128AB:H2 | − |
| Escherichia | coli | B63 | O117:H4 | − |
| Escherichia | coli | B64 | O119:H18 | − |
| Escherichia | coli | B65 | O124:H25 | − |
| Escherichia | coli | B66 | O125AB:H19 | − |
| Escherichia | coli | B67 | O126:H2 | − |
| Escherichia | coli | B68 | O128A8:H8 | − |
| Escherichia | coli | B69 | B | − |
| Escherichia | coli | B77 | O6:H1 | − |
| Escherichia | coli | B78 | | − |
| Escherichia | coli | B79 | | − |
| Escherichia | coli | B80 | | − |
| Escherichia | coli | B98 | O157:H43 | − |
| Escherichia | coli | B99 | O157:H43 | − |
| Escherichia | coli | B100 | O157:H43 | − |
| Escherichia | coli | B101 | O157:Hnm (VT−) | − |
| Escherichia | coli | B102 | O157:Hnm (VT−) | − |
| Escherichia | coli | B103 | O55:H6 | − |
| Escherichia | coli | B104 | O55:H6 | − |
| Escherichia | coli | B105 | O55:H6 | − |
| Escherichia | coli | B106 | O55:H6 | − |
| Escherichia | coli | B107 | O55:H6 | − |
| Escherichia | coli | B108 | O55:H6 | − |
| Escherichia | coli | B109 | O55:NM | − |
| Escherichia | coli | B110 | O55:H6 | − |
| Escherichia | coli | B111 | O55:H6 | − |
| Escherichia | coli | B112 | O55:H6 | − |
| Escherichia | coli | B113 | O55:H5 | − |
| Escherichia | coli | B114 | O55:H7 | − |
| Escherichia | coli | B115 | O55:H7 | − |
| Escherichia | coli | B116 | O55:H7 | − |
| Escherichia | coli | B117 | O55:H7 | − |
| Escherichia | coli | B118 | O111:H21 | − |
| Escherichia | coli | B120 | O111:H12 | − |
| Escherichia | coli | B121 | O111:H12 | − |
| Escherichia | coli | B122 | O111:NM | − |
| Escherichia | coli | B123 | O111A:HNM | − |
| Escherichia | coli | B124 | O111:H8 | − |
| Escherichia | coli | B125 | O111:HNM | − |
| Escherichia | coli | B126 | O111:H11 | − |
| Escherichia | coli | B127 | O111:H8 | − |
| Escherichia | coli | B128 | O26:H11 | − |
| Escherichia | coli | B130 | O111:H12 | − |
| Escherichia | coli | B131 | O26:H11 | − |
| Escherichia | coli | B132 | O26:H11 | − |
| Escherichia | coli | B133 | O26:H11 | − |
| Escherichia | coli | B134 | O26:H11 | − |
| Escherichia | coli | B135 | O26:H11 | − |
| Escherichia | coli | B136 | O26:H11 | − |
| Escherichia | coli | B137 | O26:H11 | − |
| Escherichia | coli | B138 | O128A:H2 | − |
| Escherichia | coli | B139 | O128A:H2 | − |
| Escherichia | coli | B140 | O45:H2 | − |
| Escherichia | coli | B141 | O128:H2 | − |
| Escherichia | coli | B142 | O128:H2 | − |
| Escherichia | coli | B143 | O111:H2 | − |
| Escherichia | coli | B144 | O111:H2 | − |
| Escherichia | coli | B145 | O111:NM | − |
| Escherichia | coli | B146 | O111:H2 | − |
| Escherichia | coli | B147 | O111:HN | − |
| Escherichia | coli | B148 | O128:H7 | − |
| Escherichia | coli | B149 | O128:H7 | − |
| Escherichia | coli | B150 | O128:H7 | − |
| Escherichia | coli | B151 | O128:H7 | − |
| Escherichia | coli | B152 | O128:H47 | − |
| Escherichia | coli | B153 | O128:H21 | − |
| Escherichia | coli | B154 | O128:H21 | − |
| Escherichia | coli | B155 | O128A:H21 | − |
| Escherichia | coli | B156 | O128:HNM | − |
| Escherichia | coli | B157 | O128:H21 | − |
| Escherichia | coli | B158 | O111:H21 | − |
| Escherichia | coli | B159 | O111:H21 | − |
| Escherichia | coli | B160 | O111:H21 | − |
| Escherichia | coli | B161 | O111:H21 | − |
| Escherichia | coli | B162 | O111:H21 | − |
| Escherichia | coli | B165 | O15:NM | − |
| Escherichia | coli | B166 | ON:HN | − |
| Escherichia | coli | B167 | ON:H32 | − |
| Escherichia | coli | B168 | O1:H32 | + |
| Escherichia | coli | B169 | ON:HN | − |
| Escherichia | coli | B170 | O79:NM | − |
| Escherichia | coli | B171 | ON:NM | − |
| Escherichia | coli | B172 | O85:HN | − |
| Escherichia | coli | B174 | ON:NM | − |
| Escherichia | coli | B175 | O6:H10 | − |
| Escherichia | coli | B176 | O6:H10 | − |
| Escherichia | coli | B178 | ON:HN | − |
| Escherichia | coli | B179 | OM:HN | − |
| Escherichia | coli | B180 | O25:NM | − |
| Escherichia | coli | B181 | ON:H10 | − |
| Escherichia | coli | B182 | O106:NM | − |
| Escherichia | coli | B183 | O5:NM | − |
| Escherichia | coli | B184 | O5:HN | − |
| Escherichia | coli | B185 | O89:HN | − |
| Escherichia | coli | B186 | O121:HN | − |
| Escherichia | coli | B187 | ON:HN | − |
| Escherichia | coli | B188 | O86:H43 | − |
| Escherichia | coli | B189 | O15:NM | − |
| Escherichia | coli | B190 | ON:HN | − |
| Escherichia | coli | B191 | O104:H21 | − |
| Escherichia | coli | B192 | O104:NM | − |
| Escherichia | coli | B193 | O104:NM | − |
| Escherichia | coli | B194 | O150:H21 | − |
| Escherichia | coli | B195 | O113:H21 | − |
| Escherichia | coli | B196 | O79:H43 | − |
| Escherichia | coli | B197 | O7:H21 | − |
| Escherichia | coli | B198 | O7:H21 | − |
| Escherichia | coli | B199 | O88:NM | − |
| Escherichia | coli | B200 | O1:NM | − |
| Escherichia | coli | B201 | O79:H25 | − |
| Escherichia | coli | B202 | ON:HN | − |
| Escherichia | coli | B203 | O7:NM | − |
| Escherichia | coli | B204 | O7:NM | − |
| Escherichia | coli | B205 | O7:NM | − |
| Escherichia | coli | B206 | O7:NM | − |
| Escherichia | coli | B207 | ON:H26 | − |
| Escherichia | coli | B208 | ON:HN | − |
| Escherichia | coli | B209 | ON:HN | − |
| Escherichia | coli | B210 | ON:HN | − |
| Escherichia | coli | B211 | O1:H6 | − |
| Escherichia | coli | B212 | OM:H18 | − |
| Escherichia | coli | B213 | ON:HM | − |
| Escherichia | coli | B214 | O2:NM | − |
| Escherichia | coli | B215 | O2:HN | − |
| Escherichia | coli | B216 | O25:HN | − |
| Escherichia | coli | B217 | O25:H1 | − |
| Escherichia | coli | B218 | O4:HN | − |
| Escherichia | coli | B219 | O25:H1 | − |
| Escherichia | coli | B220 | O25:H2 | − |
| Escherichia | coli | B221 | O6:H1 | − |
| Escherichia | coli | B222 | ON:NM | − |
| Escherichia | coli | B223 | O112:H8 | − |
| Escherichia | coli | B224 | O4:H40 | − |
| Escherichia | coli | B225 | O4:HN | − |
| Escherichia | coli | B226 | O2:NM | − |
| Escherichia | coli | B227 | O2:NM | − |
| Escherichia | coli | B228 | O2:NM | − |
| Escherichia | coli | B229 | O75:NM | − |
| Escherichia | coli | B230 | ON:H10 | − |
| Escherichia | coli | B231 | O4:H40 | − |
| Escherichia | coli | B232 | O4:H43 | − |
| Escherichia | coli | B233 | ON:NM | − |
| Escherichia | coli | B234 | ON:NM | − |
| Escherichia | coli | B235 | O78:NM | − |
| Escherichia | coli | B236 | O78:NM | − |
| Escherichia | coli | B237 | O144:H8 | − |
| Escherichia | coli | B239 | O10:K5(1):H4 | − |
| Escherichia | coli | B240 | O119:K69(b14) | − |

TABLE 12-continued

Negative Validation of the gnd Primers and Molecular Beacon #3

| Genus | Species | ID | Serovar | Results |
|---|---|---|---|---|
| Escherichia | coli | B241 | O3:K2a,bb(1):H2 | – |
| Escherichia | coli | B242 | O127:K63(b8) | – |
| Escherichia | coli | B243 | O112a,112c:K66(b11):nm | – |
| Escherichia | coli | B244 | | – |

Example 13

Quantification of gnd Target Sequences in a Test Sample

In order to quantify the amount of target sequence in a sample, DNA was isolated and amplified as described in the preceding Examples (4, 5 and 11). DNA was quantified using a standard curve constructed from serial dilutions of a target DNA solution of known concentration.

Example 14

Comparison of Primers and Molecular Beacon Probes of 2 Conserved Sequences

When a molecular beacon was not included in the reaction, amplicons were detected with SYBR® Green. An example of a suitable reaction mix for use with SYBR® Green is provided in Table 14 (dNTPs and Taq polymerase are included in the Qiagen SyBrGreen Mix).

TABLE 14

SyBrGreen Reaction Mix

| Reagent | Final concentration in reconstituted reaction |
|---|---|
| Qiagen SyBrGreen, 2X | 1.0X |
| Forward primer #1, 25 µM | 0.5 µM |
| Reverse primer #1, 25 µM | 0.5 µM |
| MgCl$_2$, 5 mM | 1.5 mM |
| Fluorescein 1 µM | 0.01 µM |

14.1 Specificity and Sensitivity of Primers

The sensitivity of the primer pair forward primer #1/reverse primer #1 was tested against a panel of 202 *E. coli* strains using the SYBR® Green Reaction Mix shown above. The primer pair amplified 100% of the panel of *E. coli* O157: H7 strains. The primer pair forward primer #2/reverse primer #2 also amplify all *E. coli* O157:H7 strains but gave higher false positive rate (8%)

From the panel of bacterial species other than *E. coli* O157: H7, the forward primer #1/reverse primer #1 pair amplified sequences from 4 strains of *E. coli* non O157:H7 i.e. 98% specificity.

A summary of the sensitivity and specificity of the forward primer #1/reverse primer #1 pair is shown in Table 15.

TABLE 15

Summary for forward primer #1 and reverse primer #1

| Sensitivity | 100.0% |
|---|---|
| Specificity | 98.0% |
| False positives | 2.0% |
| False negatives | 0.0% |
| Efficiency of primer pair | 98.3% |

The sensitivity of the primer pair forward primer #3/reverse primer #3 was tested against a panel of 27 *E. coli* O157:H7 strains using the SYBR® Green Reaction Mix shown above. The primer pair amplified 100% of the panel of *E. coli* O157:H7 strains.

From the panel of 202 bacterial species other than *E. coli* O157:H7, the forward primer #3/reverse primer #3 pair amplified sequences from 2 strains of *E. coli* non O157:H7 i.e. 99% specificity.

A summary of the sensitivity and specificity of the forward primer #3/reverse primer #3 pair is shown in Table 16.

TABLE 16

Summary for forward primer #3 and reverse primer #3

| Sensitivity | 100.0% |
|---|---|
| Specificity | 99.0% |
| False positives | 1.0% |
| False negatives | 0.0% |
| Efficiency of primer pair | 99.1% |

The sensitivity of the primer pair forward primer #4/reverse primer #4 was tested against a panel of 27 *E. coli* O157:H7 strains using the SYBR® Green Reaction Mix shown above. The primer pair amplified 100% of the panel of *E. coli* O157:H7 strains.

From the panel of 202 bacterial species other than *E. coli* O157:H7, the forward primer #4/reverse primer #4 pair amplified sequences from 113 strains of *E. coli* non O157:H7 i.e. 44% specificity.

A summary of the sensitivity and specificity of the forward primer #4/reverse primer #4 pair is shown in Table 17.

TABLE 17

Summary for forward primer #4 and reverse primer #4

| Sensitivity | 100.0% |
|---|---|
| Specificity | 44.0% |
| False positives | 55.90% |
| False negatives | 0.0% |
| Efficiency of primer pair | 44.1% |

14.2 Primer Annealing Temperatures

Annealing temperatures were determined using 500 nM of primers as indicated in table 14 and using a temperature gradient of 45° C. to 65° C. (45° C., 46.4° C., 48.8° C., 52.3° C., 57.5° C., 61.1° C., 63.6° C. and 65° C.). DNA from *E. coli* O157:H7 strain.

forward primer #1 and reverse primer #1 annealed to their target sequence up to 56.4° C.

forward primer #2 and reverse primer #2 annealed to their target sequence up to 65.1° C.

forward primer #3 and reverse primer #3 annealed to their target sequence up to 58.9° C.

forward primer #4 and reverse primer #4 annealed to their target sequence up to 67.5° C.

14.3 Molecular Beacon Efficiencies

Efficiencies were tested for molecular beacon #1, 2 and 3. Efficiencies were tested using saturated pure *E. coli* O157:H7 culture and plating this culture on the appropriate medium to determine the number of colony forming unit (CFU) in the PCR reaction.

For molecular beacon #1: Efficiency 101.5%, detection up to 1.6 CFU/PCR reaction.

For molecular beacon #2: Efficiency 86.3%, detection up to 10 CFU/PCR reaction.

For molecular beacon #3: Efficiency 125.2%, detection up to 10 CFU/PCR reaction.

14.4 Specificity and Sensitivity of Molecular Beacon Probes

A summary of the sensitivity and specificity of molecular beacon #1 and 3 is shown in Table 18 and 19.

TABLE 18

Summary for molecular beacon #1

| | |
|---|---|
| Sensitivity | 100.0% |
| Specificity | 99.8% |
| False positives | 0.2% |
| False negatives | 0.0% |
| Efficiency of beacon | 99.8% |

TABLE 19

Summary for molecular beacon #3

| | |
|---|---|
| Sensitivity | 100.0% |
| Specificity | 99.5% |
| False positives | 0.5% |
| False negatives | 0.0% |
| Efficiency of beacon | 99.6% |

The molecular beacon #1 and 3 detected 100% of the panel of E. coli O157:H7 strains.

The molecular beacon #1 and 3 both detected one false positive strain of E. coli O1:H32.

Example 15

Enrichment Procedure for Test Samples

Samples to be tested can be enriched prior to use in the assay using standard enrichment procedures. The following is representative protocol for food samples.

1) Place 25 g or 25 ml of the sample in a stomacher filter bag with 225 mL of Tryptic Soy Broth (TSB) to make a 1:10 dilution.
2) Homogenize the contents of the bag for 10 sec using a Stomacher instrument (BagMixer).
3) Incubate the stomacher bag at 35° C. for 18-24 hours in a storage rack with a closure clip attached to bag.
4) After incubation, shake to stomacher bag to homogenise the content.
5) Transfer 1 mL of the cell suspension in the bag (taking care not to take samples from the side of the stomacher bag that contains food particles) to a 2 mL sterile tube and proceed with DNA extraction (for example, following the protocol in Example 4).
8) Transfer 1 ml of the cell suspension into a sterile tube and proceed with DNA extraction (for example, following the protocol in Example 4).

The disclosure of all patents, publications, including published patent applications, and database entries referenced in this specification are specifically incorporated by reference in their entirety to the same extent as if each such individual patent, publication, and database entry were specifically and individually indicated to be incorporated by reference.

Although the invention has been described with reference to certain specific embodiments, various modifications thereof will be apparent to those skilled in the art without departing from the spirit and scope of the invention as outlined in the claims appended hereto.

The embodiments of the invention in which an exclusive property or privilege is claimed are defined as follows:

1. An isolated polynucleotide of 50 nucleotides or less in length comprising the sequence as set forth in SEQ ID NO: 20 or the complement thereof for use in combination with a pair of primers capable of specifically amplifying a sequence as set forth in SEQ ID NO: 19 to detect *E. coli* O157:H7 and/or *E. coli* O157:NM which produces verotoxin.

2. The isolated polynucleotide according to claim 1, wherein the polynucleotide is 40 nucleotides or less in length.

3. The isolated polynucleotide according to claim 1, for use as a probe.

4. The isolated polynucleotide according to claim 3, wherein said probe is a molecular beacon probe.

5. The isolated polynucleotide according to claim 4, wherein said molecular beacon probe further comprises a fluorophore, a quencher, or a combination thereof.

6. The isolated polynucleotide according to claim 4, wherein the polynucleotide consists of the sequence as set forth in SEQ ID NO: 23 or 25.

7. The isolated polynucleotide according to claim 1, wherein the polynucleotide comprises the sequence as set forth in SEQ ID NO: 23 or 25.

8. The isolated polynucleotide according to claim 1, wherein the pair of primers comprises a first polynucleotide primer comprising at least 7 consecutive nucleotides of the sequence as set forth in SEQ ID NO: 19 and a second polynucleotide primer comprising at least 7 consecutive nucleotides of a sequence complementary to SEQ ID NO: 19.

9. The isolated polynucleotide according to claim 1, wherein the pair of primers comprises a first polynucleotide primer comprising the sequence as set forth in SEQ ID NO: 21 or 27 and a second polynucleotide primer comprising a sequence complementary to SEQ ID NO: 22 or 28.

10. The isolated polynucleotide according to claim 1, wherein the pair of primers comprises a first polynucleotide primer comprising the sequence as set forth in SEQ ID NO: 21 and a second polynucleotide primer comprising a sequence complementary to SEQ ID NO: 22.

11. A combination of polynucleotides for amplification and detection of nucleic acid sequences from *E. coli* O157:H7 and/or *E. coli* O157: NM which produces verotoxin, said combination comprising:

the isolated polynucleotide according to claim 1;
a first polynucleotide primer comprising at least 7 consecutive nucleotides of the sequence as set forth in any one of SEQ ID NOs: 2-11;
a second polynucleotide primer comprising at least 7 consecutive nucleotides of a sequence complementary to the sequence as set forth in any one of SEQ ID NOs: 2-11;
wherein said first and second polynucleotide primers are capable of amplifying a portion of the gnd gene to which said isolated polynucleotide binds.

12. The combination of polynucleotides according to claim 11, wherein the first polynucleotide primer comprises at least 7 consecutive nucleotides of the sequence as set forth in SEQ ID NO: 43 and the second polynucleotide primer comprises at least 7 consecutive nucleotides of a sequence complementary to SEQ ID NO: 43.

13. The combination of polynucleotides according to claim 11, wherein the first polynucleotide primer comprises at least 7 consecutive nucleotides of the sequence as set forth in SEQ ID NO: 19 and the second polynucleotide primer comprises at least 7 consecutive nucleotides of a sequence complementary to SEQ ID NO: 19.

14. The combination of polynucleotides according to claim 11, wherein the first polynucleotide primer comprises a sequence as set forth in SEQ ID NO: 21 or 27 and the second polynucleotide primer comprises a sequence as set forth in SEQ ID NO: 22 or 28.

15. The combination of polynucleotides according to claim 11, wherein the first polynucleotide primer comprises a sequence as set forth in SEQ ID NO: 21 and the second polynucleotide primer comprises a sequence as set forth in SEQ ID NO: 22.

16. The combination of polynucleotides according to claim 11, wherein said isolated polynucleotide is a molecular beacon probe.

17. The combination of polynucleotides according to claim 16, wherein the isolated polynucleotide is 40 nucleotides or less in length.

18. The combination of polynucleotides according to claim 11, wherein said isolated polynucleotide further comprises a fluorophore, a quencher, or a combination thereof.

19. The combination of polynucleotides according to claim 1, wherein the isolated polynucleotide is 40 nucleotides or less in length.

20. The combination of polynucleotides according to claim 1 or 19, wherein the isolated polynucleotide comprises the sequence as set forth in SEQ ID NO: 20 or the complement thereof.

21. The combination of polynucleotides according to claim 1, wherein the isolated polynucleotide comprises the sequence as set forth in SEQ ID NO: 23 or 25.

22. The combination of polynucleotides according to claim 1, wherein the isolated polynucleotide consists of the sequence as set forth in SEQ ID NO: 23 or 25.

23. A method of detecting *E. coli* O157:H7 and/or *E. coli* O157:NM which produces verotoxin in a sample, said method comprising the steps of:
 (i) contacting a sample suspected of containing, or known to contain, *E. coli* O157:H7 and/or *E. coli* O157:NM which produces verotoxin with a combination of polynucleotide primers capable of amplifying a *E. coli* target sequence within the gnd gene, under conditions that permit amplification of the target nucleotide sequence, said polynucleotide primers comprising:
  (a) a first polynucleotide primer comprising at least 7 consecutive nucleotides of the sequence as set forth in any one of SEQ ID NOs: 2-11;
  (b) a second polynucleotide primer comprising at least 7 consecutive nucleotides of a sequence complementary to any one of SEQ ID NOs: 2-11; and
 (ii) detecting amplified target nucleotide sequence by contacting said amplified target nucleotide sequence with the isolated polynucleotide of claim 1,
 wherein said first and second primers are capable of amplifying a portion of the gnd gene to which said isolated polynucleotide binds, and wherein detection of amplified target nucleotide sequence indicates the presence of *E. coli* O157:H7 and/or *E. coli* O157:NM which produces verotoxin in the sample.

24. The method according to claim 23, wherein the first polynucleotide primer comprises at least 7 consecutive nucleotides of the sequence as set forth in SEQ ID NO: 43 and the second polynucleotide primer comprises at least 7 consecutive nucleotides of a sequence complementary to SEQ ID NO: 43.

25. The method according to claim 23, wherein the first polynucleotide primer comprises at least 7 consecutive nucleotides of the sequence as set forth in SEQ ID NO: 19 and the second polynucleotide primer comprises at least 7 consecutive nucleotides of a sequence complementary to SEQ ID NO: 19.

26. The method according to claim 23, wherein the first polynucleotide primer comprises the sequence as set forth in SEQ ID NO: 21 or 27 and the second polynucleotide primer comprises a sequence complementary to SEQ ID NO: 22 or 28.

27. The method according to claim 23, wherein the first polynucleotide primer comprises the sequence as set forth in SEQ ID NO: 21 and the second polynucleotide primer comprises a sequence complementary to SEQ ID NO: 22.

28. The method according to claim 23, wherein said isolated polynucleotide is a molecular beacon probe.

29. The method according to claim 23, wherein said isolated polynucleotide further comprises a fluorophore, a quencher, or a combination thereof.

30. The method according to claim 23, wherein steps (i) and (ii) are conducted simultaneously.

31. The method according to claim 23, further comprising a step to enrich the microbial content of the sample prior to step (i).

32. The method according to claim 23, wherein the isolated polynucleotide is 40 nucleotides or less in length.

33. The method according to claim 23, wherein the isolated polynucleotide comprises the sequence as set forth in SEQ ID NO: 23 or 25.

34. The method according to claim 23, wherein the isolated polynucleotide consists of the sequence as set forth in SEQ ID NO: 23 or 25.

35. A kit for the detection of *E. coli* O157:H7 and/or verotoxin producing *E. coli* O157:NM in a sample, said kit comprising:
 the isolated polynucleotide of claim 1; a first polynucleotide primer comprising at least 7 consecutive nucleotides of the sequence as set forth in any one of SEQ ID NOs: 2-11; a second polynucleotide primer comprising at least 7 consecutive nucleotides of a sequence complementary to any one of SEQ ID NOs: 2-11.

36. The kit according to claim 35, wherein the first polynucleotide primer comprises at least 7 consecutive nucleotides of the sequence as set forth in SEQ ID NO: 43 and the second polynucleotide primer comprises at least 7 consecutive nucleotides of a sequence complementary to SEQ ID NO: 43.

37. The kit according to claim 35, wherein the first polynucleotide primer comprises at least 7 consecutive nucleotides of the sequence as set forth in SEQ ID NO: 19 and the second polynucleotide primer comprises at least 7 consecutive nucleotides of a sequence complementary to SEQ ID NO: 19.

38. The kit according to claim 35, wherein said first polynucleotide primer comprises a sequence as set forth in SEQ ID NO: 21 or 27 and the second polynucleotide primer comprises a sequence as set forth in SEQ ID NO: 22 or 28.

39. The kit according to claim 35, wherein the first polynucleotide primer comprises a sequence as set forth in SEQ ID NO: 21 and the second polynucleotide primer comprises a sequence as set forth in SEQ ID NO: 22.

40. The kit according to claim 35, wherein said isolated polynucleotide is a molecular beacon probe.

41. The kit according to claim 40, wherein the isolated polynucleotide is 40 nucleotides or less in length.

42. The kit according to claim 35, wherein said isolated polynucleotide further comprises a fluorophore, a quencher, or a combination thereof.

43. The kit according to claim 35, further comprising one or more amplification reagents selected from the group of: buffers, salts, enzymes, enzyme co-factors and nucleotides.

44. The kit according to claim 35, wherein the isolated polynucleotide is 40 nucleotides or less in length.

45. The kit according to claim 35, wherein the isolated polynucleotide comprises the sequence as set forth in SEQ ID NO: 20 or the complement thereof.

46. The kit according to claim 35, wherein the isolated polynucleotide comprises the sequence as set forth in SEQ ID NO: 23 or 25.

47. The kit according to claim 35, wherein the isolated polynucleotide consists of the sequence as set forth in SEQ ID NO: 23 or 25.

* * * * *